US011427852B2

(12) United States Patent
M'Koma

(10) Patent No.: US 11,427,852 B2
(45) Date of Patent: Aug. 30, 2022

(54) METHODS FOR DIAGNOSING AND TREATING INFLAMMATORY BOWEL DISEASE

(71) Applicant: Meharry Medical College, Nashville, TN (US)

(72) Inventor: Amosy M'Koma, Antioch, TN (US)

(*) Notice: Subject to any disclaimer, the term of this patent is extended or adjusted under 35 U.S.C. 154(b) by 22 days.

(21) Appl. No.: 16/571,034

(22) Filed: Sep. 13, 2019

(65) Prior Publication Data
US 2020/0149087 A1 May 14, 2020

Related U.S. Application Data

(63) Continuation of application No. PCT/US2018/024069, filed on Mar. 23, 2018.

(60) Provisional application No. 62/475,506, filed on Mar. 23, 2017.

(51) Int. Cl.
| | |
|---|---|
| *C12Q 1/6837* | (2018.01) |
| *C12Q 1/6876* | (2018.01) |
| *G01N 33/58* | (2006.01) |
| *G01N 33/60* | (2006.01) |
| *G01N 33/68* | (2006.01) |
| *C12Q 1/6883* | (2018.01) |
| *A61K 45/06* | (2006.01) |
| *C12Q 1/37* | (2006.01) |

(52) U.S. Cl.
CPC .............. *C12Q 1/37* (2013.01); *C12Q 1/6837* (2013.01); *C12Q 1/6876* (2013.01); *C12Q 1/6883* (2013.01); *G01N 33/582* (2013.01); *G01N 33/60* (2013.01); *G01N 33/68* (2013.01); *A61K 45/06* (2013.01); *C12Q 2600/158* (2013.01); *G01N 2333/8146* (2013.01); *G01N 2800/065* (2013.01)

(58) Field of Classification Search
CPC .. C12Q 1/37; G01N 33/68; G01N 2333/8146; G01N 2800/065
See application file for complete search history.

(56) References Cited

U.S. PATENT DOCUMENTS

| | | | | |
|---|---|---|---|---|
| 2004/0092515 A1* | 5/2004 | Lundstedt | ................. | A61P 1/04 514/225.2 |
| 2005/0234024 A1* | 10/2005 | Clarke | ................. | A61K 31/165 514/171 |
| 2009/0105281 A1* | 4/2009 | Epstein | ..................... | A61P 3/10 514/262.1 |
| 2013/0316985 A1* | 11/2013 | Deng | ..................... | A61K 31/05 514/150 |
| 2018/0085400 A1* | 3/2018 | Sentman | ............. | C07K 16/2833 |

FOREIGN PATENT DOCUMENTS

| | | |
|---|---|---|
| WO | 2008147900 | 12/2008 |
| WO | 2016149282 | 9/2016 |

OTHER PUBLICATIONS

Williams (Disease of the Colon & Rectum 2016 vol. 59, e92-e93) (Year: 2016).*
Gruber (PLOS One 2013 8:e71661) (Year: 2013).*
Stronati et al. Digestive and Liver Disease 2010 vol. 42: 848-853 (Year: 2010).*
Wehkamp, J., et al., Innate Immunity and Colonic Inflammation, Digestive Diseases and Sciences, vol. 47, No. 6, Jun. 2002, pp. 1349-1355.
Warner, E. and Dieckgraefe, B., Application of Genome-Wide Gene Expression Profiling by High-Density DNA Arrays to the Treatment and Study of Inflammatory Bowel Disease, Inflammatory Bowel Diseases, vol. 8, No. 2, 2002, pp. 140-157.
Marlow, G. et al., Transcriptomics to stuy the effect of a Mediterranean-inspired diet on inflammation in Crohn's disease patiens, Human Genomics, vol. 7, No. 24, 2013.
Gori, P. et al., Defective Paneth Cell—Mediated Host Defense in Pediatric Ileal Crohn's Disease, 2010, The American Journal of Gastroenterology, p. 452-459. vol. 105.
Rath, T. et al., Enhanced expression of MMP-7 and MMP-13 in inflammatory bowel disease: a precancerous potential?, Inflammatory Bowel Diseases, 2006, p. 1025-1035, vol. 12. No. 11.
Fahlgren, A. et al., Increased expression of antimicrobial peptides and lysozyme in colonic epithelial cells of patients with ulcerative colotis, Clinical & Experimental Immunology, 2003, p. 90-101, vol. 131, No. 90-101.
Kirkegaard, T. et al., Expression and localisation of matrix metalloproteinases and their natural inhibitors in fistulae of patients with Crohn's disease, Gut, 2004, p. 701-709, vol. 53, No. 5.
Guagnozzi, D. et al., Natalizumab in the treatment of Crohn's disease, Biologies, 2008, p. 275-284, vol. 2, No. 2.
Loftus, C. et al., Cyclosporin for refractory ulcerative colitis, Gut, 2003, p. 172-173, vol. 52, vol. 2.
Kuhn, F. et al., Surgical Prinicples in the Treatment of Ulcertative Colitis, Viszeralmedizin, 2015, p. 246-250, vol. 31, No. 4.
Written Opinion of the International Searching Authority for PCT/us2018/024069, dated Sep. 24, 2019.
EMD Millipore, Anti-Alpha Defensin-5 (HD5) Antibody, clone 8C8, 2020, available at: http://www.emdmillipore.com/US/en/product/Anti-Alpha-Defensin-5-HD5-Antibody-clone-8C8,MM_NF-MABF31.

* cited by examiner

*Primary Examiner* — Changhwa J Cheu
(74) *Attorney, Agent, or Firm* — Bradley Arant Boult Cummings LLP; Timothy L. Capria; Alexandra C. Lynn

(57) ABSTRACT

Methods and materials are disclosed for testing biomarkers in a subject suffering from inflammatory bowel disease (IBD) are described herein. Such detection can be useful for diagnosing and treating ulcerative colitis (UC) and Crohn's disease (CD), two forms of IBD that are otherwise difficult to distinguish. The method includes measuring the level of one or more of several biomarkers, including HD5 or MMP-7, which are expressed differentially in patents with UC and CD. A treatment may be based on the determination of whether the subject has ulcerative colitis or Crohn's disease.

17 Claims, 15 Drawing Sheets

Specification includes a Sequence Listing.

Diagnostic Uncertainty and Inaccuracy in IBD

IHC Detection of HD5

Control

DV

Moderate UC

Moderate CC $p < 0.0001$

```
MRTIAILAAILLVALQAQAESLQERADEATTQKQSGEDNQDLAISFAGNG
LSALRTSGSQARATCYCRTGRCATRESLSGVCEISGRLYRLCCR
         10        20        30        40        50
MRTIAILAAILLVALQAQAESLQERADEATTQKQSGEDNQDLAISFAGNG
LSALRTSGSQARATCYCRTGRCATRESLSGVCEISGRLYRLCC
         60        70        80        90
```

Red = Signal Peptide, Blue = Pro-protein, Yellow = Mature Protein (56-94)

Molecule Processing

| Feature key | Position(s) | Length | Description | Graphical View | Feature Identifier |
|---|---|---|---|---|---|
| Signal peptide[j] | 1 - 19 | 19 | | | |
| Peptide[i] | 20 - 94 | 75 | Defensin-5 | | PRO_0000006787 |
| Peptide[i] | 23 - 94 | 72 | HD5(23-94) | | PRO_0000417387 |
| Peptide[i] | 29 - 94 | 66 | HD5(29-94) | | PRO_0000417388 |
| Peptide[i] | 56 - 94 | 39 | HD5(56-94) | | PRO_0000417389 |
| Peptide[i] | 63 - 94 | 32 | HD5(63-94) | | PRO_0000417390 |

```
HD5 1   MRTIAILAAILLVALQAQAESLQERADE-ATTQKQSGEDNQDLAISFAGNGLSALRTSGS   59
        MRT+AILAAILLVALQAQAE LQ RADE A    +Q   D  ++ +S A +    A + GS
HD3 1   MRTLAILAAILLVALQAQAEPLQARADEVAAAPEQIAADIPEVVVSLAWDESLAPKHPGS   60

HD5 60  QARATCYCRTGRCATRESLSGVCEISGRLYRLCC   93
        +    CYCR  C  E   G C   GRL+  CC
HD3 61  RKNMDCYCRIPACIAGERRYGTCIYQGRLWAFCC   94

HD5 1   MRTIAILAAILLVALQAQAESLQERADE-ATTQKQSGEDNQDLAISFAGNGLSALRTSGS   59
        MRT+AILAAILLVALQAQAE LQ RADE A    +Q   D  ++ +S A +    A + GS
HD1 1   MRTLAILAAILLVALQAQAEPLQARADEVAAAPEQIAADIPEVVVSLAWDESLAPKHPGS   60

HD5 60  QARATCYCRTGRCATRESLSGVCEISGRLYRLCC   93
        +    CYCR  C  E   G C   GRL+  CC
HD1 61  RKNMACYCRIPACIAGERRYGTCIYQGRLWAFCC   94

HD5 1   MRTIAILAAILLVALQAQAESLQERAD------EATTQKQSGEDNQDLAISFAGNGLSA   53
        MRT+ IL A+LLVALQA+AE LQ   D      EA  Q+Q G ++QD A+SFA +  S+
HD6 1   MRTLTILTAVLLVALQAKAEPLQAEDDPLQAKAYEADAQEQRGANDQDFAVSFAEDASSS   60

HD  54  LRTSGSQARATCYCRTGRCATRESLSGVCEISGRLYRLCC   93
        LR GS      TC+CR  C + E   G C + G  +R CC
HD6 61  LRALGSTRAFTCHCRRS-CYSTEYSYGTCTVMGINHRFCC   99
```

FIG. 7

Crohn's Disease : Colon
Normal Ileum

Table 3

| Patient Group | Sigmoid | Cecum | Ascending | Transverse | Descending | Pancolitis |
|---|---|---|---|---|---|---|
| Diverticulitis | 4 | 2 | -- | 1 | 3 | -- |
| Mild UC | 1 | 2 | 4 | 1 | 6 | 1 |
| Moderate UC | 3 | 1 | 1 | 2 | 5 | 1 |
| Severe UC | 1 | -- | 3 | 4 | 3 | 4 |
| Mild CC | -- | 2 | 6 | 2 | 4 | -- |
| Moderate CC | -- | 1 | 5 | 5 | 4 | -- |
| Severe CC | 2 | -- | 6 | 4 | 3 | -- |

FIG. 14

Table 4

| Patient Sample ID | Attending Pathologist Diagnosis Year 200-2007 | Attending Physician Diagnosis Year 200-2007 | Patient Outcomes Year 2014 - New Diagnosis | Mean Area Fraction of DEFA5 (%) Count by NEARAS |
|---|---|---|---|---|
| 12-07-A1588 | IC | UC | UC | 20 |
| 12-10-A051A | IC | IC | (CC) | 80 |
| ED56738T-003 2nd Opinion | IC<br>IC | UC<br>UC | UC | 10 |
| ED59253T-003 2nd Opinion | IC<br>IC | UC<br>UC | UC | 20 |
| M1122098A2 | IC | IC | (UC) | 20 |
| M1122098A2 | IC | UC | UC | 10 |
| M3124384A1 | IC | CC | UC | 10 |
| M3124405A2 2nd Opinion | IC<br>IC | CC<br>UC | CC | 70 |
| D-24672 | IC | UC | CC | 70 |
| D-4632 | IC | UC | UC | 20 |
| D-3163 | IC | CC | CC | 90 |
| D-26455 | IC | IC | (CC) | 80 |
| D-26452 | IC | CC | CC | 80 |
| D-325 | IC | UC | UC | 10 |
| D-2462 | IC | CC | CC | 100 |
| A-24057 | IC | UC | UC | 20 |
| A-24066 | IC | CC | CC | 100 |
| A-24042 | IC | IC | (UC) | 20 |
| 56738T | IC | IC | (CC) | 100 |
| MAD12-625 | IC | IC | (UC) | 10 |
| M1151537AA | IC | UC | UC | 20 |

FIG. 15

METHODS FOR DIAGNOSING AND TREATING INFLAMMATORY BOWEL DISEASE

CROSS-REFERENCE TO RELATED APPLICATIONS

This application is a continuation of, and cites the priority of, PCT/US2018/024069 filed March 2018, which is currently pending, and cites the priority of U.S. Patent Application No. 62/475,506 (filed on 23 Mar. 2017). All of the foregoing application are incorporated by reference herein in their entireties.

STATEMENT REGARDING FEDERALLY SPONSORED RESEARCH OR DEVELOPMENT

This invention was made with government support under grant numbers R21DK095186; U54CA091408-09S1; U54CA091408-0952; U54RR026140; U54MD007593; UL1RR024975; UL1TR000445; G12MD007586; U54CA163069; R24 DA036420; and S10RR0254970 awarded by the National Institute of Health. The government has certain rights in the invention.

In this context "government" refers to the government of the United States of America.

BACKGROUND OF THE DISCLOSURE

Inflammatory bowel disease ("IBD") is the chronic relapsing inflammation of all, or part of, the digestive tract. There are two types of IBD, ulcerative colitis ("UC") and Crohn's disease ("CD"). Crohn's disease involving only colon is termed as Crohn's colitis ("CC"). When nondefinitive evaluations have been established for criteria for either UC or CC are labeled as "indeterminate colitis (IC)". UC results in inflammation and ulceration of the mucosal and, to a lesser degree, the submucosal linings of the colon and rectum. CC differs from UC in that it may result in inflammation deeper within all the four colonic layers (transmural inflammation and skip lesions). Furthermore, CC may also affect other organs through fistulation.

UC and CD affect an estimated 2 million people in the US alone with associated annual health care costs of over $6.8 billion. While UC and CD are both types of IBDs, differences between patients having UC or CD has major implications. Currently, clinicians use inexact combined classification for patients having IBD, which include clinical, endoscopy, radiological, and histopathology in an effort to diagnose CD and UC. Nonetheless, differentiating patients having UC or CD among patients suffering from IBD remains challenging, so much so that cases of patients having IBD that are difficult classify as UC or CD are classified as having indeterminate colitis ("IC"). A significant subgroup of IBD patients are misdiagnosed or have a correct diagnosis delayed despite use of a state-of-the-art classification system applying clinical, endoscopic, radiologic and histologic tools. Indeed, it is estimated that 30% of patients suffering from IBD cannot currently be accurately diagnosed as CD or UC.

In addition, 15% of colonic IDB cases that undergo ileal pouch anal anastomosis surgery, as they are diagnosed with UC, will subsequently have their original diagnosis changed to CD based on their postoperative follow-up visits, clinical and histopathology changes, and development of de novo CD in the ileal pouch. Ileal pouch anal anastomosis, a treatment normally suitable for UC but not CD, restores gastrointestinal continuity after surgical removal of the colon and rectum, and involves the creation of a pouch of small intestine to recreate the removed rectum.

Implications of distinguishing cases of UC and CD include choice of medical treatment, timing of surgery, prognosis, whether to offer the patient an ileal pouch anal anastomosis, and lifestyle expectations. For these reasons, there is a need for improving the diagnosis, and subsequent treatment, of subjects having IBD.

SUMMARY

It has been discovered that Paneth cells secreted DEFA5 also known as HD5 serve as biomarkers for determining whether a patient suffering from IBD has UC or CD.

In a first aspect, a method of measuring DEFA5 (HD5) in a patient suffering from or at risk of IBD is disclosed, said method comprising: obtaining a sample from the patient; and measuring at least one of the expression of DEFA5 (HD5) and the concentration of DEFA5 (HD5) in the sample.

In a second aspect, a method of treating a patient suffering from or at risk of IBD is disclosed, said method comprising: obtaining a sample from the patient; measuring at least one of the expression of DEFA5 (HD5) and the concentration of DEFA5 (HD5) in the sample; and performing an intervention on the patient to treat one of Crohn's disease and ulcerative colitis.

In a third aspect, a method of measuring MMP-7 in a patient suffering from or at risk of IBD is disclosed, said method comprising: obtaining a sample from the patient; and measuring at least one of the expression of MMP-7 and the concentration of MMP-7 in the sample.

In a fourth aspect, a method of treating a patient suffering from or at risk of IBD is disclosed, said method comprising: obtaining a sample from the patient; measuring at least one of the expression of MMP-7 and the concentration of MMP-7 in the sample; and performing an intervention on the patient to treat one of Crohn's disease and ulcerative colitis.

In a fifth aspect, a method of measuring biomarkers in a patient suffering from or at risk of IBD is disclosed, said method comprising: obtaining a sample from the patient; measuring at least one of the expression of DEFA5 (HD5) and the concentration of DEFA5 (HD5) in the sample; and measuring at least one of the expression of MMP-7 and the concentration of MMP-7 in the sample.

In a sixth aspect, a method of treating a patient suffering from or at risk of IBD is disclosed, said method comprising: obtaining a sample from the patient; measuring at least one of the expression of DEFA5 (HD5) and the concentration of DEFA5 (HD5) in the sample; measuring at least one of the expression of MMP-7 and the concentration of MMP-7 in the sample; and performing an intervention on the patient to treat one of Crohn's disease and ulcerative colitis.

In a seventh aspect, a kit for measuring DEFA5 (HD5) and MMP-7 in a sample is disclosed, the kit comprising: a first assay for measuring at least one of the expression of human DEFA5 (HD5) and the concentration of human DEFA5 (HD5) in a sample; and a second assay for measuring at least one of the expression of human MMP-7 and the concentration of human MMP-7 in a sample.

In an eighth aspect, a method of measuring a biomarker in a patient suffering from or at risk of inflammatory bowel disease (IBD) is disclosed, said method comprising: obtaining a sample from the patient; and measuring a level of the biomarker in the same, the level of the biomarker selected from the group consisting of: the expression of the biomarker, the activity of the biomarker, and the concentration of the biomarker; wherein said biomarker is selected from Table 1.

The above methods may include diagnosing the patient as suffering from CD if the level of DEFA5 (HD5) concentration or DEFA5 (HD5) expression is greater than a given threshold level, diagnosing the patient as suffering from UC if the level of DEFA5 (HD5) concentration or DEFA5 (HD5) expression is below a threshold level, or both.

The above methods may include diagnosing the patient as suffering from CD if the level of MMP-7 concentration or MMP-7 expression is less than a given threshold level, diagnosing the patient as suffering from UC if the level of MMP-7 concentration or MMP-7 expression is above a threshold level, or both.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present concepts in a simplified form as a prelude to the more detailed description that is presented later.

BRIEF DESCRIPTION OF THE DRAWINGS

FIG. 7 shows the sequence details of canonical human HD5 protein.

FIG. 14 is a condensed list of the samples included in all experiments and the colon locations from which the samples were taken.

FIG. 15 shows an assessment of levels of HD5 in surgical pathology colectomy samples via IHC in patients described in FIG. 1A.

DETAILED DESCRIPTION

Definitions

Figure 1A:
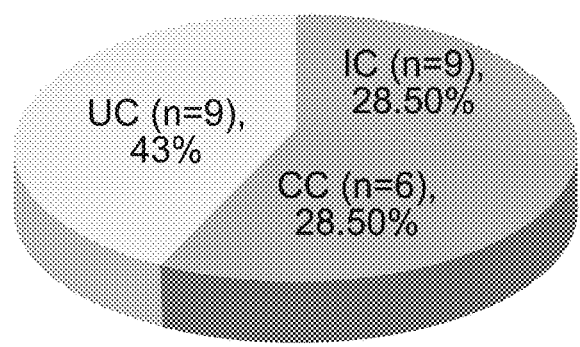
FIGS. 1A and 1B illustrate a comparison of new diagnoses according to an embodiment of an assay method of the present invention with previous attending physical diagnoses.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense, unless expressly so defined herein. Well-known functions or constructions may not be described in detail for brevity or clarity.

The terminology used herein is for the purpose of describing particular embodiments only and is not intended to be limiting. As used herein, the singular forms "a", "an", and "the" are intended to include the plural forms as well, unless the context clearly indicates otherwise.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. This term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical, exemplary degrees of error or variation are within 20%, preferably within 10%, and more preferably within 5% of a given value or range of values. For biological systems, the term "about" refers to an acceptable standard deviation of error, preferably not more than 2-fold of a given value. Numerical quantities in this detailed description are approximate unless stated otherwise, meaning that the term "about" or "approximately" can be inferred when not expressly stated.

The terms "individual", "subject", or "patient" as used herein refer to any animal, including mammals, such as mice, rats, other rodents, rabbits, dogs, cats, swine, cattle, sheep, horses, primates, and humans. The terms may specify male or female or both, or exclude male or female.

The terms "treatment", "treat", and "treating", as used herein, refer to a course of action (such as administering a compound or pharmaceutical composition) initiated after the onset of a clinical manifestation of a disease state or condition so as to eliminate or reduce such clinical manifestation of the disease state or condition. Such treating need not be absolute to be useful.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

Methods of Treatment and Diagnosis

An assay method of diagnosing UC and CD in a subject, such as a human, suffering from IBD is described. The method measures DEFA5 (HD5) in tissue taken from a subject having IBD. DEFA5 (HD5) is a small, microbicidal innate immune system protein belonging to the alpha defensing family of mammalian defensing peptides. DEFA5 (HD5) is expressed in various tissues and particularly on mucosal surfaces. DEFA5 (HD5) is encoded by the gene DEFA5. DEFA5 (HD)5 is involved in host defense mechanisms, and is highly expressed in secretory granules of Paneth cells of the small intestine (ileum). Like most secreted proteins, HD5 is synthesized as prepro-HD5 (1-94) that undergoes proteolytic processing first, to the inactive pro-HD5s (20-94), HD5 (23-94) and HD5 (29-94). HD5 (23-94) and HD5 (29-94) are found within tissues, while HD5 (20-94) is the predominant intracellular form. The pro-HD5s are then processed to two active or mature forms. HD5 (56-94) and HD5 (63-94) with HD5 (63-94) being the most abundant form. These mature forms of HD5 are cysteine-rich host defense peptides which exert a broad-spectrum antimicrobial activity and contribute to innate immunity in the human gut. As used herein, HD5 may refer to exclusively mature forms or inactive forms of HD5.

Matrix metalloproteinase-7 (MMP-7, encoded by the MMP7 gene) is responsible for cleaving and activating HD5. It is believed that there may be a dysfunction in the activation pathway of HD5 in patients suffering from moderate and severe CD, and thus, an excess amount of inactive form HD5 is a potential mechanism for inflammation in patients suffering from CD. This excessive amount of inactive form HD5 may cause increased damage to the epithelial lining and potentially even a dysregulation in the levels and make-up of gut flora. The canonical structure of human MMP-7 is a 54 residue polypeptide (see Uniprot accession number A5GZ72).

The sample can be taken from any suitable source for measuring HD5 concentration, HD5 expression levels, MMP-7 expression, or MMP-7 concentration, such as the tissue samples from the large intestine or rectum. In this disclosure the term "expression of HD5" should be interpreted to mean the expression of the DEFA5 gene; "levels of HD5" should be interpreted to mean the concentration of HD5; "expression of MMP-7" should be interpreted to mean the expression of the MMP7 gene; "levels of MMP-7" should be interpreted to mean the concentration of matrix metalloproteinase-7.

The sample may be taken from a subject who is suffering from or at risk of IBD. The subject may display one or more symptoms characteristic of IBD, such as severe diarrhea, abdominal pain, fatigue, and weight loss. In some embodiments of the method, the subject displays more than one of said symptoms. In further embodiments the subject displays 2, 3, or 4 of said symptoms.

It has been discovered that the genes encoding HD5 and MMP-7 are differentially expressed in subjects having UC and CD; and further, that the concentration of HD5 is significantly higher in tissues of CD patients than in UC patients. Used in this way, HD5 and MMP-7 concentrations, and HD5 expression and MMP-7 expression, can be utilized and measured as biomarkers for distinguishing UC and CD in patients having IBD. This can in turn be used to more effectively treat the subject. For example, as ileal pouch anal anastomosis is clinically much more successfully in patients having UC than in patients suffering from CD, patients identified as having levels of HD5 or MMP-7 levels indicative of UC, or not having CD, may be treated with ileal pouch anal anastomosis. Indeed, as HD5 is produced by Paneth cells only, one would not typically expect to find Paneth cells that secret HD5 in the colon. The inventors have discovered Paneth cells (secreting HD5) are abundantly found in subjects having UC. On the other hand, patients identified as having levels of HD5 or MMP-7 and HD5 or MMP-7 expression indicative of CD may be treated with any suitable treatment for CD. In an embodiment, a diagnosing step, such as diagnosing a subject with UC or CD, is optional.

The methods may include a step of comparing the level of the biomarker in question to a benchmark value. The benchmark value may be a measure of central tendency based on levels observed in one or more populations of subjects that are established to be unafflicted by either of UC or CD. For example, the benchmark value may be a mean level of the gene expression or protein concentration observed in samples from a population of subjects who are unafflicted by UC, unafflicted by CD, or both. The population may be defined by one or more of the patient's geography, age, ethnicity, sex, and medical history. The benchmark value may take into account a measure of variation combined with a measure of central tendency. For example, the benchmark value may be a mean level of the gene expression or protein concentration observed in a given tumor population, plus or minus a margin of error. The benchmark may be based on raw measurements (such as fragments of mRNA or cDNA per kb gene length per million reads) or normalized measurements (such as % of normal expression, or expression compared to a constitutively expressed or widely expressed gene with generally consistent expression, such as β-actin).

The benchmark may also be established by analysis of a control sample that is measured alongside the sample from the subject. Examples of suitable control samples are: a sample from a subject unafflicted with UC, a sample from a subject unafflicted with CD, a sample from a subject afflicted with UC (although unafflicted with CD), a sample from a subject afflicted with CD (although unafflicted with UC), a sample from a subject afflicted with diverticulitis (although unafflicted with either of UC or CD), and a sample from a subject unafflicted from IBD.

In an embodiment, an assay method of differentially diagnosing UC and CD in a patient suffering from IBD includes measuring the level of HD5 or MMP-7 or HD5 or MMP-7 expression present in a sample obtained from the patient. The level of HD5 or MMP-7 concentration or expression in the tissue may be measured by any suitable peptide analysis. For example, the measuring step may include one or more of enzyme-linked immunosorbent assay (ELISA), cation-ion exchange, NMR analysis, genome-wide transcriptome analysis, and mass spectrometry. The method may include comparing the concentration or expression of the biomarker in the sample to the benchmark, and making a diagnosis if the concentration or expression of the biomarker in the sample is significantly less than or significantly greater than the benchmark value. For the example, the method may comprise comparing the concentration or expression of HD5 in the sample to the benchmark, and making a diagnosis of CD if the concentration or expression of HD5 in the sample is significantly greater than the benchmark value. As another example, the method may comprise comparing the concentration or expression of HD5 in the sample to the benchmark, and making a diagnosis of UC if the concentration or expression of HD5 in the sample is not significantly greater than the benchmark value. As another example, the method may comprise comparing the concentration or expression of MMP-7 in the sample to the benchmark, and making a diagnosis of UC if the concentration or expression of MMP-7 in the sample is significantly greater than the benchmark value. As another example, the method may comprise comparing the concentration or expression of MMP-7 in the sample to the benchmark, and making a diagnosis of CD if the concentration or expression of MMP-7 in the sample is not significantly greater than the benchmark value. In a further example, the method comprises measuring the concentration or expression of both MMP-7 and HD5, and making a diagnosis of either: CD if the concentration or expression of MMP-7 in the sample is not significantly greater than the benchmark value and the concentration or expression of HD5 is significantly greater than the benchmark value; or UC if the concentration or expression of MMP-7 in the sample is significantly greater than the benchmark value and the concentration or expression of HD5 is not significantly greater than the benchmark value.

The difference in expression or concentration may be considered significant based on any of a variety of known statistical tests for significance. These are generally based on a collection of measurements made from a sampled population, and are affected by both the population size and the sampling size. Such statistical tests are well known in the art and are not further elaborated upon in this disclosure; outside references can be relied upon to enable those skilled in the art to determine statistical significance, such as Rosener's *Fundamentals of Biostatistics,* 8th ed. (2015), Cengage Learning, Boston, Mass.

The method may include diagnosing the patient as having UC if HD5 or HD5 expression is at any level that is indicative of a patient not having CD, such as less than 5× normal levels of HD5 (i.e., levels of HD5 typical of a subject unafflicted with CD), less than about 5×-30× normal levels of HD5 or HD5 expression, less than about 31× normal levels, or less than about 118× normal levels. In a further embodiment, the patient is diagnosed as having UC if HD5 expression is at a level of less than $10^6$, $10^7$, $1.9\times10^7$, $6\times10^5$, or $3\times10^6$ HD5 mRNA transcript per 10 ng RNA. In some embodiments of the method the patient may be diagnosed as having CD if the level of HD5 expression is at any level indicative of a patient having CD, such as at least $3\times10^6$, $10^7$, $1.9\times10^7$, $7\times10^7$, $10^8$, $1.2\times10^8$, or from about to $3\times10^6$ to $1.2\times10^8$ HD5 mRNA Transcript per 10 ng RNA. The diagnosing may diagnose the patient as having CD if the patient has a MMP-7 concentration or MMP-7 expression level indicative of a patient having CD, such as up to a threshold limit that is 10× a benchmark value of MMP-7 concentration or MMP-7 expression. In further embodiments, the diagnosis may be CD using a threshold limit of up to 5×, and up to 1× a benchmark value. As used herein, a "normal level" of HD5 or HD5 expression means a level of HD5 or HD5 expression in the digestive tract tissue from a subject not having CD or UC, or a subject suffering from IBD and specifically UC. Normal HD5 expression may refer to from $1\times10^5$ to $9\times10^5$ HD5 mRNA Transcript per 10 ng RNA, or about $6\times10^5$ HD5 mRNA Transcript per 10 ng RNA. As used herein, a "normal level" of MMP-7 or MMP-7 expression means a level of MMP-7 or MMP-7 expression in the digestive tract tissue from a subject not having CD or UC, or a subject suffering from IBD, specifically CD.

In another embodiment, an assay method for differentially diagnosing UC and CD in a patient suffering from, or at risk of, IBD includes measuring the level of MMP-7 or MMP-7 expression present in a sample obtained from the patient. The level of MMP-7 or MMP-7 expression in the tissue may be measured by any suitable peptide analysis. In an embodiment, the method of diagnosing may be performed ex vivo.

In one embodiment, the assay methods involve determining the status of a subject with respect to the activity and/or expression of HD-5 or MMP-7 or the activity and/or expression of a polypeptide regulated by HD-5 or MMP-7. In one embodiment, such methods comprise determining the level of expression or activity of HD-5 or MMP-7 or a polypeptide regulated by HD-5 or MMP-7 in a sample from the subject. The method may further comprise collecting the sample from the subject. As used herein, a biological sample which is subjected to testing is a sample derived from a subject and includes, but is not limited to, any biological material, such as a bodily fluid. Examples of bodily fluids include, but are not limited to, whole blood, serum, saliva, tissue infiltrate, pleural effusions, lung lavage fluid, bronchoalveolar lavage fluid, and the like. The biological fluid may be a cell culture medium or supernatant of cultured cells. For example, the sample can be a blood sample or a serum sample. As another example the sample may be tissue or fluids from the subject's digestive tract. Some embodiments of the method involve a sample of intestinal tissue. In specific embodiments, the biological sample is collected from the colon of a subject (such as colonic tissue) or the ileum of a subject (such as ileal tissue).

Some embodiments of the method comprise measuring the concentration of the biomarker protein by selectively staining or dying the sample form the subject and measuring the signal from the stain. The stain or dye may comprise an antibody or an antibody fragment to recognize the protein. The stain or dye may also comprise a reporter, such a colorimetric group, a radionuclide, a stable isotope, a fluorophore, a chromophore, an enzyme, a magnetic particle, and a quantum dot. The concentration of the protein can then be measured by observing the signal from the reporter, such as by microscopy, colorimetry, radiometry, fluoroscopy, magnetotaxis, or any combination of the foregoing. In a specific embodiment of the method, the concentration of HD5 or MMP-7 is measured by immunostaining the sample with an immunostain that recognizes the biomarker and counting the number of stained cells by microscopy. This approach has the advantage of relative simplicity, and only requires the types of equipment that are already present in typical clinical laboratories. In specific examples in which the biomarker is HD5, a diagnosis can be made based on a threshold number of cells that stain positive, such as 10%, 20%, and 30%. If the number of HD5 stained cells is significantly above the threshold value, than a diagnosis of CD can be made; whereas if the number of HD5 stained cells is significantly below the threshold value, than a diagnosis of UC can be made.

Those subjects in which HD-5 or MMP-7 activity and/or expression differs (increased or decreased) from a control or benchmark value or the activity of a polypeptide regulated by HD-5 or MMP-7 differs as compared to a control or benchmark value are determined to be suffering from or at risk for a disease states and conditions associated with or characterized by increased or decreased HD-5 or MMP-7 activity.

Assay techniques that can be used to determine levels of expression or activity in a sample are known. Such assay methods include, but are not limited to, radioimmunoassays, reverse transcriptase PCR (RT-PCR) assays, immunohistochemistry assays, in situ hybridization assays, competitive-binding assays, Western Blot analyses, ELISA assays and proteomic approaches, two-dimensional gel electrophoresis (2D electrophoresis) and non-gel based approaches such as mass spectrometry or protein interaction profiling. Assays also include, but are not limited to, competitive and non-competitive assay systems using techniques such as radioimmunoassays, enzyme immunoassays (EIA), enzyme linked immunosorbent assay (ELISA), sandwich immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays. For examples of immunoassay methods, see U.S. Pat. Nos. 4,845,026 and 5,006,459.

In an ELISA assay, an antibody is prepared, if not readily available from a commercial source, specific to an antigen, such as, for example, HD-5 or MMP-7 or a polypeptide regulated by HD-5 or MMP-7. In addition, a reporter antibody generally is prepared. The reporter antibody is attached to a detectable reagent such as a radioactive, fluorescent, or enzymatic reagent, for example horseradish peroxidase enzyme or alkaline phosphatase. In one embodiment of the ELISA, to carry out the ELISA, antibody specific to the antigen is incubated on a solid support that binds the antibody. Any free protein binding sites on the dish are then covered by incubating with a non-specific protein. Next, the sample to be analyzed is incubated with the solid support, during which time the antigen binds to the specific antibody. Unbound sample is washed out with a buffer. A reporter antibody specifically directed to the antigen and linked to a detectable reagent is introduced resulting in binding of the reporter antibody to any antibody bound to the antigen. Unattached reporter antibody is then washed out. Reagents for detecting the presence of the reporter antibody are then added. The detectable reagent is then determined in order to determine the amount of antigen present. In an alternate embodiment, the antigen is incubated with the solid support, followed by incubation with one or more antibodies, wherein at least one of the antibodies comprises a detectable reagent. Quantitative results may be obtained by reference to a standard curve.

Optionally, a genetic sample from the biological sample can be obtained. The genetic sample comprises a nucleic acid, preferably RNA and/or DNA. For example, in determining the expression of genes mRNA can be obtained from the biological sample, and the mRNA may be reverse transcribed into cDNA for further analysis. Alternatively, the mRNA itself is used in determining the expression of genes. A genetic sample may be obtained from the biological sample using any techniques known in the art (Ausubel et al. Current Protocols in Molecular Biology (John Wiley & Sons, Inc., New York, 1999); Molecular Cloning: A Laboratory Manual, 2nd Ed., ed. by Sambrook, Fritsch, and Maniatis (Cold Spring Harbor Laboratory Press: 1989); Nucleic Acid Hybridization (B. D. Hames & S. J. Higgins eds. 1984) each of the foregoing being incorporated herein by reference). The nucleic acid may be purified from whole cells using DNA or RNA purification techniques. The genetic sample may also be amplified using PCR or in vivo techniques requiring subcloning. The genetic sample can be obtained by isolating mRNA from the cells of the biological sample and reverse transcribing the RNA into DNA in order to create cDNA (Khan et al. Biochem. Biophys. Acta 1423: 17 28, 1999).

Once a genetic sample has been obtained, it can be analyzed. The analysis may be performed using any techniques known in the art including, but not limited to, sequencing, PCR, RT-PCR, quantitative PCR, restriction fragment length polymorphism, hybridization techniques, Northern blot, microarray technology, and similar techniques. In determining the expression level of a gene or genes in a genetic sample, the level of expression may be normalized by comparison to the expression of another gene such as a well-known, well characterized gene or a housekeeping gene (for example, actin). For example, reverse-transcriptase PCR (RT-PCR) can be used to detect the presence of a specific mRNA population in a complex mixture of thousands of other mRNA species. Hybridization to clones or oligonucleotides arrayed on a solid support (e.g., gridding) can be used to both detect the expression of and quantitate the level of expression of that gene. In this approach, a cDNA encoding an antigen is fixed to a substrate. The substrate may be of any suitable type including but not limited to glass, nitrocellulose, nylon, or plastic. At least a portion of the DNA encoding the antigen is attached to the substrate and then incubated with the analyte, which may be RNA or a complementary DNA (cDNA) copy of the RNA, isolated from the sample of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantifying the yield, and then using that material to generate a standard curve.

The method may include diagnosing the patient as having UC if MMP-7 concentration or MMP-7 expression is at any level indicative of a patient having UC, such as from 2×-100×, 10×, 2×-50×, 5×-15×, or about 10× normal MMP-7 concentration or MMP-7 expression levels. In some embodiments of the method, the patient may be diagnosed as having CD if the MMP-7 concentration or MMP-7 expression is at any level indicative of a patient having CD, such as less than 1×-10× or 2×-5× normal levels of MMP-7 or MMP-7 expression.

A method of treating IBD in a patient suffering from IBD may include: (a) measuring the level of HD5 or HD5 expression present in a sample obtained from the patient, said measuring step optionally comprising one of cation-ion exchange, NMR analysis, genome-wide transcriptome analysis, and mass spectrometry, whereby a level of HD5 or HD5 expression is obtained; (b) if the level of HD5 or HD5 expression is at a level indicative of a patient not having CD, treating the IBD in the patient with a suitable medical treatment for UC; if the level of HD5 or HD5 expression is at a level indicative of a patient having CD, treating the IBD in the patient with a suitable medical treatment for CD. In another embodiment, levels of MMP-7 or MMP-7 expression are measured rather than levels of HD5 to determine whether to treat UC or CD.

Suitable medical treatments for UC include ileal pouch anal anastomosis or the administration of pharmaceutical agents or salts thereof. Suitable pharmaceutical agents may be one or more of: an iron supplement; an oral 5-aminosalicylate, such as mesalamine, balsalazide and olsalazine; an anti-inflammatory; a corticosteroid; an immunosuppressant such as azathioprine, mercaptopurine, methotrexate, and cyclosporine; an anti-TNF-alpha antibody such as infliximab, adalimumab, and golimumab; an anti-α4-integrin antibody such as vedolizumab; and an antibacterial antibiotic, such as ciprofloxacin and metronidazole. Surgeries that are sometimes used to treat UC include a proctocolectomy, and an ileal pouch anal anastomosis. Note that ileal pouch anal anastomosis are recognized as relatively ineffective when used to treat CD, in contrast to UC. It should also be noted that cyclosporine and golimumab, while currently approved for the treatment of UC in the United States, are not currently approved for the treatment of CD. Some embodiments of the method involve performing an intervention that is effective to treat UC, but either ineffective to treat CD or not yet approved by regulatory authorities for the treatment of CD.

Suitable medical treatments for CD include the administration of pharmaceutical agents or salts thereof. Suitable pharmaceutical agents include: an oral 5-aminosalicylate, such as mesalamine; a vitamin supplement, such as a vitamin B-12 supplement and a vitamin D supplement; a mineral supplement, such as a calcium supplement; an anti-inflammatory; a corticosteroid such as prednisone and budesonide; an immunosuppressant such as azathioprine, tacrolimus, methotrexate, and mercaptopurine; an anti-TNF-α antibody, such as infliximab, adalimumab, and certolizumab pegol; an anti-α-4-integrin antibody, such as natalizumab and vedolizumab; an anti-interleukin antibody, such as ustekinumab; and an antibacterial antibiotic, such as metronidazole, and ciprofloxacin. Although certolizumab pegol, methotrexate, and natalizumab are approved in the US for the treatment of CD, they are not currently approved for the treatment of UC. Surgical approaches are sometimes used to treat severe cases of CD. Such surgeries include ostomy, colostomy, ileostomy, bowel resection, colectomy, proctocolectomy, and strictureplasty. In some embodiments of the method, the subject is treated using a diet that is advantageous for the management of CD, but not necessarily advantageous in the management of UC. One such diet is a low fat diet. Some embodiments of the method involve performing an intervention that is effective to treat CD, but either ineffective to treat UC or not yet approved by regulatory authorities for the treatment of UC.

In an embodiment, the level of HD5 or HD5 expression may be elevated above normal levels in patients who are likely to be diagnosed UC but, at the time the HD5 or HD5 expression level is measured, diagnosed as having IC. These patients may be treated with any suitable medical treatments for UC.

A kit is provided for measuring HD5 in a subject. The kit may include a detectable antibody that is capable of binding with HD5. The antibody may be capable of binding with HD5 yet not bind with other defensins, such as HD4 and HD5. The antibody may be a purified HD5-specific monoclonal or polyclonal antibody, such as the HDAC5 Antibody from GenWay Biotech, Inc. FIG. 7 shows the amino acid sequence of HD5, including a schematic showing HD5 antibody epitopes to distinguish pro-HD5 from mature HD5. FIG. 7 also shows the alignment of the primary sequence of HD5 with that of HD1 showing the differences between the two polypeptides. The methods herein can involve detecting any protein having the consensus sequence of HD5 such as to account for natural variation of HD5 in humans having different HD5 sequences.

A kit is provided for measuring HD5 and MMP-7 in a subject. The kit may find use in several of the methods provided above, as well as others. The kit may be, for example, used for the diagnosis of inflammatory bowel disease. The kit comprises an assay for measuring at least one of HD5 concentration and HD5 expression; and an assay for measuring at least one of MMP-7 concentration and MMP-7 expression.

FIG. 12 illustrates a histological staining of colon tissue in a subject having CC. FIG. 12B illustrates a histological staining of colon tissue in a subject having UC. FIG. 12C illustrates a histological staining of colon tissue in a subject having Diverticulitis. FIG. 12D illustrates a histological staining of colon tissue in a subject having a normal colon.

Working Example 1

Abstract

Inability to distinguish Crohn's colitis from ulcerative colitis leads to the diagnosis of indeterminate colitis. This greatly effects medical and surgical care of the patient because treatments for the two diseases vary. Approximately 30 percent of inflammatory bowel disease patients cannot be accurately diagnosed, increasing their risk of inappropriate treatment. We sought to determine whether transcriptomic patterns could be used to develop diagnostic biomarker(s) to delineate inflammatory bowel disease more accurately. Four patients groups were assessed via whole-transcriptome microarray, qPCR, Western blot, and immunohistochemistry for differential expression of Human α-Defensin-5. In addition, immunohistochemistry for Paneth cells and Lysozyme, a Paneth cell marker, was also performed. Aberrant expression of Human α-Defensin-5 levels using transcript, Western blot, and immunohistochemistry staining levels was significantly upregulated in Crohn's colitis, p<0.0001. Among patients with indeterminate colitis, Human α-Defensin-5 is a reliable differentiator with a positive predictive value of 96 percent. We also observed abundant ectopic crypt Paneth cells in all colectomy tissue samples of Crohn's colitis patients. In a retrospective study, we show that Human α-Defensin-5 could be used in indeterminate colitis patients to determine if they have either ulcerative colitis (low levels of Human α-Defensin-5) or Crohn's colitis (high levels of Human α-Defensin-5). Twenty of 67 patients (30 percent) who underwent restorative proctocolectomy for definitive ulcerative colitis were clinically changed to de novo Crohn's disease. These patients were profiled by Human α-Defensin-5 immunohistochemistry. All patients tested strongly positive. In addition, we observed by both hematoxylin and eosin and Lysozyme staining, a large number of ectopic Paneth cells in the colonic crypt of Crohn's colitis patient samples. Our experiments are the first to show that Human α-Defensin-5 is a potential candidate biomarker to molecularly differentiate Crohn's colitis from ulcerative colitis, to our knowledge. These data give us both a potential diagnostic marker in Human α-Defensin-5 and insight to develop future mechanistic studies to better understand crypt biology in Crohn's colitis.

Methods

Clinical Samples and Ethical Consideration

Figure 13:
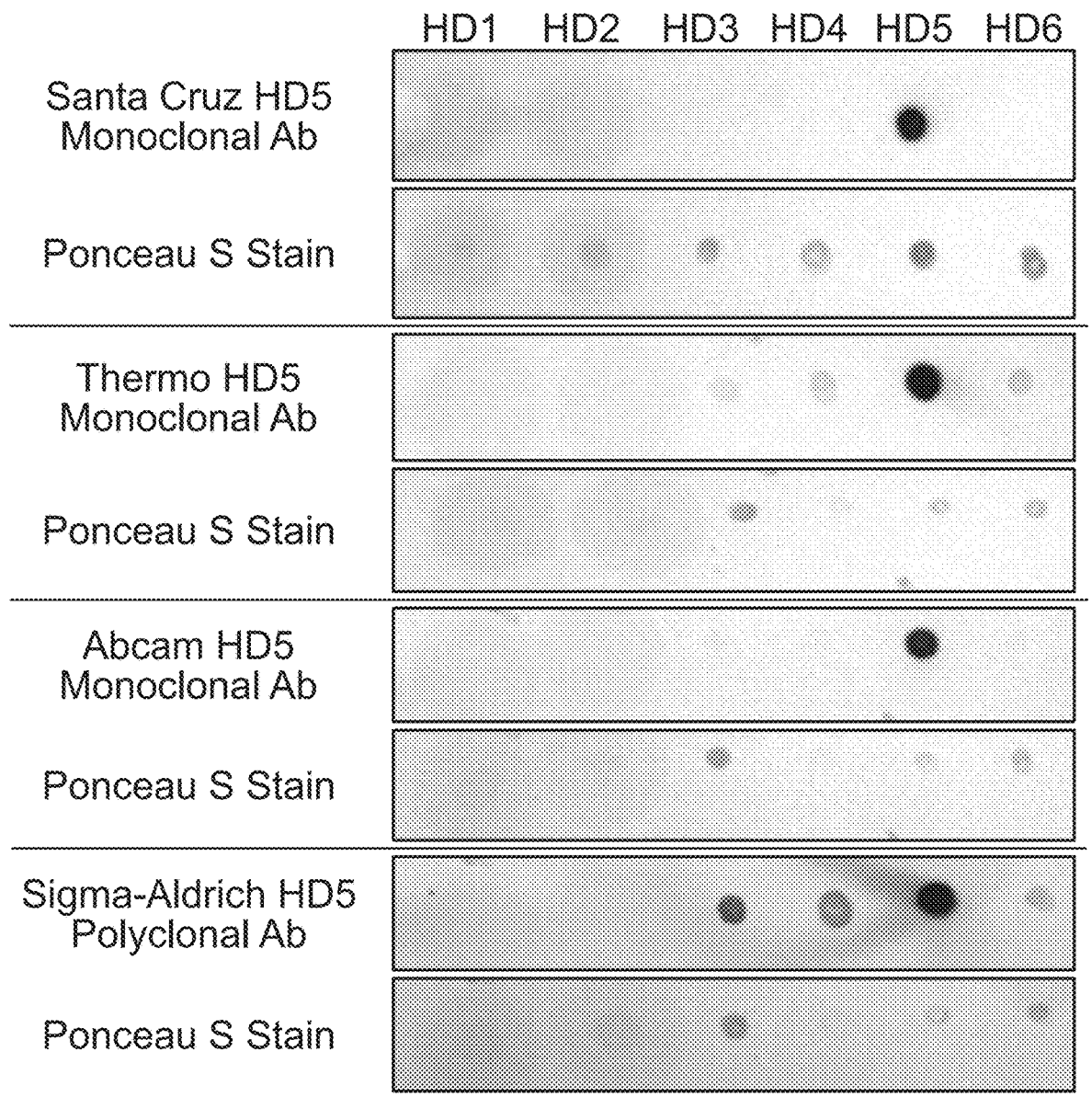
FIG. 13 illustrates the results of an antibody specificity assay. Dot blots were performed on recombinant HD1-6 with various commercial antibodies to determine specificity to HD5. Ponceau S Stain is used as a loading control. We found that the antibody from Santa Cruz was the most specific for DEFA5 (HD5) of those tested.

In order to carryout tissue profiling of differentially expressed proteins/genes in IBD, we first sought ethical approval from the Meharry Medical College (IRB file #: 100916AM206) and Vanderbilt University Medical Center (IRB file # s: 080898 and 100581) Institutional Review Boards [20]. Informed consent was provided, and patient participation in the study was voluntary. Patient samples comprised of surgical pathology colectomy tissues from adults with definitive UC and CC phenotypes as well as those diagnosed with IC at Vanderbilt University Medical Center (VUMC) between 2000 and 2007. The full thickness surgical samples of colectomy tissue were analyzed by pathology teams at MMC and VUMC, Schools of Medicine following established protocol criteria for IBD subtypes. For each selected sample, medical records data on patient demographics, preoperative variables prior to and after time of ileal pouch-anal anastomosis surgery, surveillance endoscopic and clinical findings, and medical and surgical treatment history were reviewed retrospectively. Samples included in all experiments were taken from various parts of the colon; all inflamed tissue unless otherwise indicated. A condensed list of samples and colon locations are included in Table 3, as shown in FIG. 13.

Diagnostic Criteria for Inflammatory Bowel Disease

Pathology teams at MMC and VUMC Schools of Medicine used the following protocol criteria for the final surgical pathology reporting.

For ulcerative colitis. Characteristic pattern of involvement of colon, worse distally in untreated patients; lack of perianal or fistulizing disease; no granulomas, except in association with ruptured/injured crypts; no transmural lymphoid aggregates or other transmural inflammation; no involvement of terminal ileum, except mild "backwash ileitis" in cases with severe cecal involvement and no pyloric metaplasia in terminal ileum.

For Crohn's disease. Involvement of other sites in the gastrointestinal tract (skip lesions, segmental disease); perianal or fistulizing disease; granulomas, not in association with ruptured/injured crypts and terminal ileum involvement.

For indeterminate colitis. Distribution favors UC, but focal transmural inflammation, or inflammation in ileum more than expected in backwash ileitis and no fistulizing disease.

Vanderbilt Patient Medical Records Database

The availability of a detailed IBD patient database registry at Vanderbilt University Medical Center (VUMC) made chart review and follow-up surveillance possible. Medical records data on patient demographics, preoperative variables prior to and after IPAA surgery, surveillance of endoscopic and clinical findings, and medical and surgical treatment history were retrieved retrospectively.

Indeterminate Colitis Clinical Retrospective Study

A retrospective investigation was conducted to identify a cohort of patients diagnosed with IC and registered in the IBD Center at VUMC. Twenty-one patients, initially classified as IC at the time of diagnosis between years 2000-2007, were identified and reevaluated for disease course in 2014, after a mean surveillance follow-up of 8.7±3.7 (range, 4-14) years, in order to identify the rates of diagnosis resolution to UC or CC. Diagnosis for each patient was determined based on standard clinical and pathologic features as previously described [21, 22].

Three gastrointestinal pathologists blinded to clinical diagnosis reconciled and confirmed colitis diagnosis for each patient and represented a consensus among treating physicians. Patients who clinically did not changed and maintained the IC diagnosis were tested via IHC and Nikon Element Advanced Research Analysis Software (NEARAS) for HD5 levels to determine if HD5 could be used to identify CC from UC.

Restorative Proctocolectomy Operated Patients' Retrospective Study

One hundred twenty patients with definitive UC underwent RPC surgery between Apr. 18, 2001 and Jun. 18, 2008. Of the 120 patients, 67 had their diagnosis re-evaluated after a mean follow up of 9.4 (range, 6-13) years of functionally acceptable pouches. Compiled medical records allowed us to re-evaluate a progressive course of UC patients following RPC. Clinical information needed for each of these patients was available in the IBD medical records registry database at VUMC. The aim was to reevaluate patients who underwent RPC operation for definitive UC and had a change in diagnosis to de novo Crohn's ileitis. Patients who had a change in diagnosis should reconcile the molecular biometric test that delineates IC into CC; again using NEARAS for HD5 levels.

cDNA Microarray

We performed a whole-transcriptome microarray with RNA extracted and pooled from human full thickness colon samples from UC and CC patients (n=5/group) (Affymetrix, Santa Clara, Calif.).

NanoString nCounter Human Inflammation Kit Gene Expression

RNA from UC and CCI tissue (and diverticulitis tissue used as a control) was processed by NanoString (NanoString Technologies Inc., Seattle, Wash.) to determine gene expression level according to the manufacturer protocol [23].

Real-Time RT-PCR

Real-Time RT-PCR was used to measure transcript levels of HD5. RNA was extracted from three human colon biopsy samples each from moderate UC and CC, and diverticulitis (DV) as a non-IBD control (RNeasy Miniprep Kit, Qiagen, CA). cDNA was generated using iScript cDNA synthesis kit (Bio-Rad, Hercules, Calif.). Pre-designed TaqMan probes (Thermo Fisher Scientific, Waltham, Mass.) were purchased for HD5 and GAPHD control, and all samples were run in triplicate using a CFX96 qPCR thermocycler (Bio-Rad). Data were analyzed per the ΔΔCt method of analysis.

Western Blot and Immunohistochemistry

Western blot was used to assess any differences in HD5 protein levels. Protein was extracted from a minimum of 10 colon biopsy samples each from mild, moderate, and severe UC; mild, moderate, and severe CC; and non-IBD DV control. Whole cell lysates were extracted from full-thickness colon samples using T-PER (Thermo Fisher Scientific) per manufacturer's protocol. Bradford Assays (Bio-Rad) were run to determine protein concentration, and protein was loaded onto a 4-20% SDS-PAGE tris/glycine gel (Bio-Rad). Proteins were transferred to PVDF (Bio-Rad), and Western blots for HD5 and β-actin loading control were performed with primary and secondary antibodies (Santa Cruz, Dallas, Tex.) per manufacturer's protocol. Blots were visualized with Opti-4CN colorimetric detection kit (Bio-Rad) and imaged with ChemiDoc XRS+imaging system (Bio-Rad). Band intensities were measured and data analysis performed with Image Lab Software (Bio-Rad).

Five colon tissue protein extracts and staining of HD5 per disease by immunohistochemistry (IHC) was done as previously described. 24 Quantification of HD5 staining was analyzed manually by microscopy and automatically quantified using Nikon's Eclipse Ti microscope with built-in NEARAS [24, 25].

NEARAS Technology for Quantification of Immunohistochemistry Staining

NEARAS (Melville, N.Y.) was used to calculate the number of cells with HD5 staining in IHC tissue. A mean intensity threshold of 20 to 255 intensity units was established to eliminate a false-positive signal from background staining. A circularity parameter of 0.5 to 1 and equivalent diameter of 5-15 micrometer was used to select for cells. All threshold parameters were used in each image to count the number of HD5-positive cells in tissue samples.

Statistical Analysis

The Vanderbilt University Microarray Core Laboratory performed statistical analyses for the microarray. Transcriptome level fold changes and the significance of those changes were calculated using one way ANOVA with Bonferroni's correction for multiple comparisons. Significantly changed transcripts were defined as having >2.0 fold expression change from controls and a Benjamini-Hochberg (BH) false discovery rate corrected ANOVA p-value <0.05. All other statistical analyses were performed using GraphPad Prism v6 software [26]. qRT-PCR and IHC HD5 counts were examined by applying an unpaired two-tailed Student's t-test with the Welch correction, respectively. Western blots were analyzed by ANOVA followed by Fisher's test for multiple comparisons. Chi square tests were utilized for determining relatedness of HD5 levels to CC. For all statistical analyses, p<0.05 indicated a statistical significance.

Dual Staining of Human α-Defensin-5 and Lysozyme

DoubleStain IHC was performed on a Lab Vision autostainer 360 (Thermo fisher) using Abcam's M&R on human tissue (DAB & AP/Red) staining kit (ab210059, Abcam Biotechnology, Cambridge, UK). The manufacture's recommended conditions were used with the following modifications. The mouse anti-α-defensin 5 (sc-53997, Santa Cruz Biotechnology, Inc, Dallas, Tex.) and rabbit anti-lysozyme (ab-2408) were used at a 1:50 dilution in OP Quanto antibody Diluent (Thermo Fisher, Waltham, Wash.). Prior to addition of antibody for 45 minutes, tissues were incubated for 10 min with Utravision hydrogen peroxide block (Thermo Fisher) followed by a 5 min incubation with Ultravisoion Quanto protein block. A single incubation with Permanent Red was used for ileum tissue, whereas two consecutive 10 min permanent Red incubations were performed for colonic tissue. Following hematoxylin counter staining, tissue was exposed to Richard-Allen Scientific Blueing Reagent (Thermo Fisher).

Antigen retrieval was performed in 1 mM EDTA pH 8.4, 0.05% Tween 20 for 20 minutes at 98° C. (60° C. preheat/ 70° C. cool down) using the Labvision PT Module (Thermo Scioentific). Image color deconvolution was performed with Fiji ImageJ 1.51f (http://imagej.nih.gov/ij) using the Fast Red, Fast Blue and DAB built in stain vector plugin.

Results

Nearly 30% of Indeterminate Colitis Patients Cannot be Delineated into UC or CC

A retrospective investigation was conducted to identify a cohort of patients diagnosed with IC to determine if they could be properly delineated into UC or CC over time. We followed 21 patients who were diagnosed with IC between the years 2000-2007 and reevaluated in 2014. A mean surveillance follow-up period was 8.7±3.7 (range, 4-14) years. Fifteen of the 21 (71.4%) had their original diagnosis changed; 9 to UC (43%) and 6 to CC (28.5%). Six (28.5%) patients remained clinically inconclusive and retained their diagnosis of IC (FIG. 1A). These data were collected in the absence of any type of biomarker.

Figure 1B:
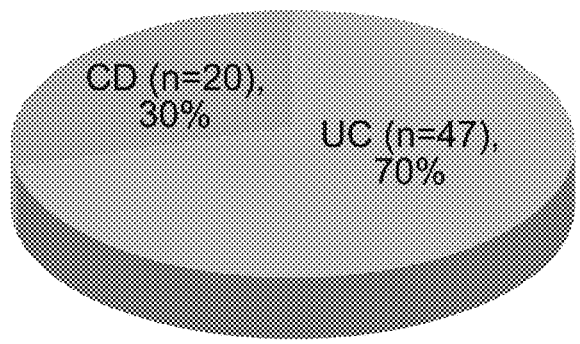

Thirty Percent of Restorative Proctocolectomy Operated Crohn's Colitis Patients were Misdiagnosed as Ulcerative Colitis A retrospective investigation was conducted to identify a cohort of patients that underwent RPC and IPAA surgery for a definitive UC diagnosis to determine if they had been misdiagnosed. We identified 67 such patients. A mean surveillance follow-up period was 9.4 (range, 6-13) years. A change in diagnosis to de novo Crohn's disease of the ileal pouch was clinically observed in 20 (30%) patients (FIG. 1B). In the other 47 (70%) cases, the initial diagnosis of UC remained clinically unchanged. These data were collected in the absence of any type of biomarker. Because of these results, we sought to determine if there are potential genes that may be used to better differentiate between UC and CC at first clinical biopsy and prior to any surgical intervention.

There is Differential Expression of Human α-Defensin-5 in Inflammatory Bowel Disease We initially performed whole-transcriptome microarray with RNA extracted and pooled from human full thickness colon samples from UC and CC patients (n=5) using the Affymetrix gene expression array according to the manufacturer's instructions (Affymetrix, Santa Clara, Calif.) Tissues from diverticulitis (DV) were used as control. This analysis showed a total of 484 genes that were up or down-regulated (~2-fold) between the two diseases. Among the upregulated genes were α-defensin-5, other antimicrobial peptides, and mucins (Table 1). HD5 was increased the most: 31-fold in CC vs. UC (in a previous study HD5 increase by 118-fold in CC versus UC—data not shown). A full list of the microarray results can be found in Table 1.

To replicate these data in a different platform, an independent analysis by PCR array (NanoString Technologies Inc. Seattle, Wash.) was carried out on 5 different human full thickness colon samples from UC and CC patients. Although the NanoString array only specifically targeted inflammatory genes, the only gene to show up in both the microarray and the PCR array was HD5. The NanoString array determined that HD5 was increased 118-fold in CC vs. UC in these human samples, compared to 31-fold in the previous samples analyzed by microarray (Table 2).

Figure 2A:
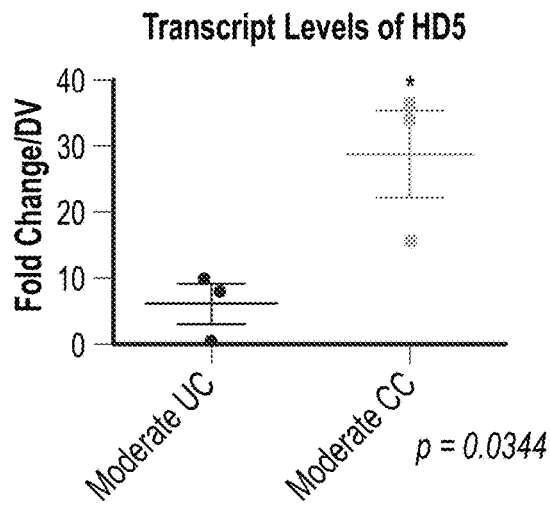
FIGS. 2A-H show differential expression and concentration of DEFA5 (HD5) in CC and UC subjects. 2A is a bar graph showing transcription levels of DEFA5 (HD5) in subjects suffering from moderate UC as compared to moderate CC. 2B is a western blot analysis of DEFA5 (HD5) levels in diverticulitis, UC, and CC subjects. 2C is a scatter plot graph quantifying the western blot DEFA5 (HD5) levels. 2D-G is histological staining of DEFA5 (HD5) tissue samples from control, diverticulitis, UC, and CC subjects, respectively. 2H is a bar graph showing quantified DEFA5 (HD5) staining counts of UC and CC subjects as compared to the control.
Figure 2B:
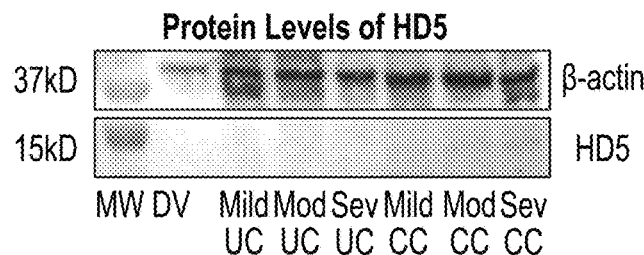
Figure 2C:
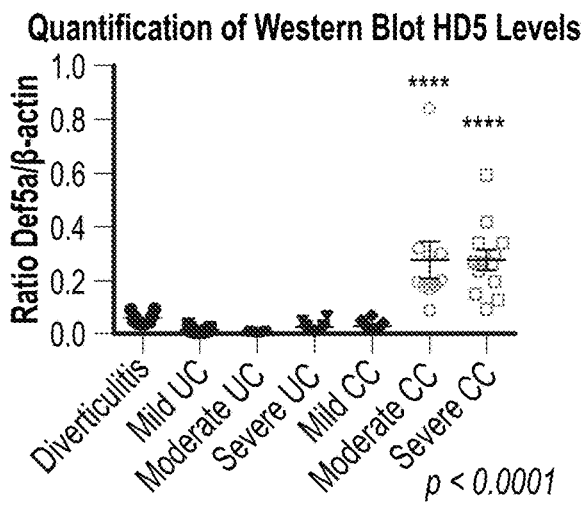
Figure 2D:
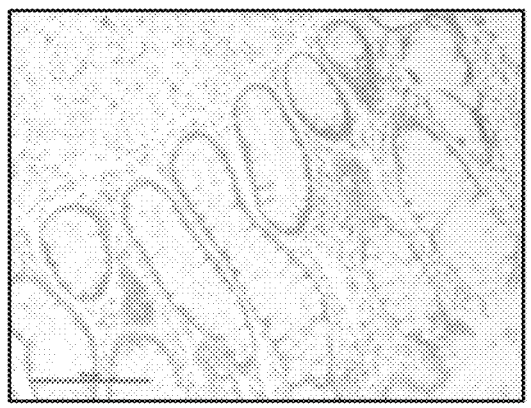
Figure 2E:
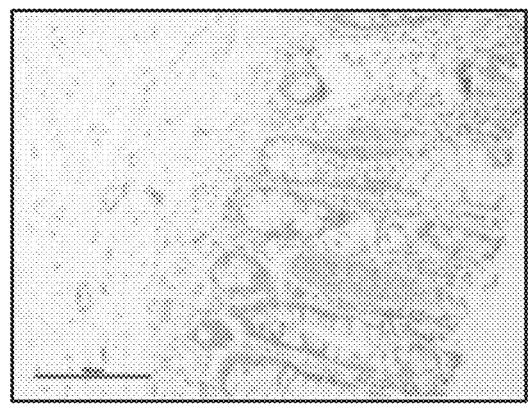
Figure 2F:
Figure 2G:
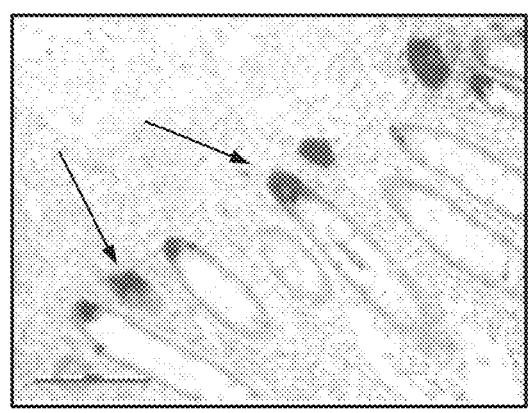
Figure 2H:
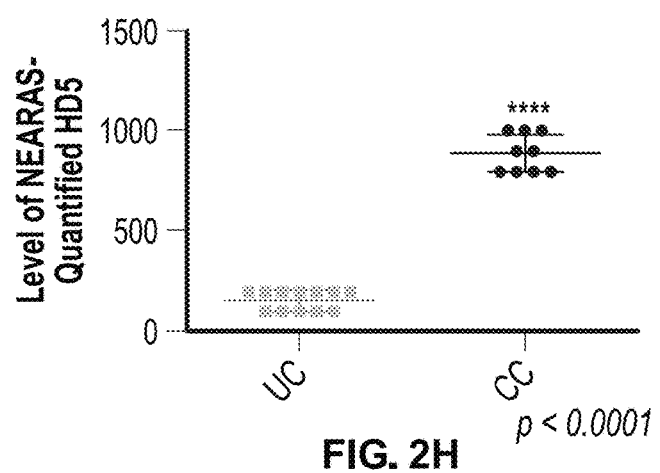

To further validate these data, we assessed the expression of HD5 by semi-quantitative RT-PCR using RNA extracted from moderate CC and moderate UC tissues (n=3). This analysis also showed a significant increase in transcript levels of HD5 in CC compared to UC (FIG. 2A, SEM, p<0.05). Several commercially available HD5 antibodies have been developed. Due to the sequence homology of the alpha defensin class of proteins, we tested a set of antibodies to assess specificity to HD5. We performed dot blots using commercially available antibodies against recombinant HD1-6. We determined that the monoclonal antibody from Santa Cruz Biotechnology, Inc. (Santa Cruz, Calif.) showed the highest level of specificity for HD5, and was therefore used in subsequent assays (FIG. 13). Next, we assessed the expression of HD5 by Western blotting (n=10 for each disease state). Samples were run individually on western blots, with a combination of disease states on each blot, and we show an example of an individual sample per disease state in a representative blot (FIG. 2B). When we take each individual sample into consideration across all western blots, protein densitometry analysis also shows significantly higher levels of HD5 in moderate and severe CC compared to all other disease states (FIG. 2C, p<0.0001). Finally, we examined the expression of HD5 in moderate disease activity of IBD and control tissues by IHC using FFPE sections. This analysis revealed that HD5 levels are indeed increased in CC (FIG. 2G) when compared to DV, and UC and normal (NL) control tissue (FIGS. 2D, 2E and 2F). Quantification of the HD5 IHC staining spot counts by NEARAS revealed a 5.6-fold increase of HD5 in CC vs. UC (FIG. 2H, p<0.0001). We believe the IHC data explains the weak western blot banding patterns. Because the western blots were run with full-thickness samples, there is a low overall abundance of HD5 in the tissue; the IHC shows that it is much localized in the base of individual colonic crypts. Because of this, further analysis is done using IHC instead of western blots.

Table 1 shows a list of targets from an affymetrix cDNA microarray. A total of 484 genes were highlighted in the microarray as potential markers for distinguishing UC from CC. The gene showing the largest fold change between the two diseases was Human Defensin 5 (HD5).

Table 2 shows a full list of targets from NanoString Human Inflammation PCR array. 16 inflammatory genes were changed in this subset of samples. HD5 was the only gene to appear in both the microarray and the NanoString PCR array.

TABLE 2

| Gene Symbol | NanoString p-value (CC vs UC) | NanoString Fold Change (CC vs UC) | Microarray Fold Change (CC vs UC) |
| --- | --- | --- | --- |
| DEFA5 | 0.00182525 | 118.145 | 31.0374 |
| RBP2 | 0.282548 | 6.8909 | — |
| CD53 | 0.417119 | −1.32516 | — |
| SAA2 | 0.575901 | −1.36908 | — |
| SNORD13P2 | 0.0839705 | −1.42879 | — |
| SMAD4 | 0.00233383 | −1.49572 | — |
| SNORD28 | 0.00995582 | −1.58122 | — |
| ALOX5AP | 0.153036 | −1.61452 | — |
| SCARNA8 | 0.132287 | −1.63997 | — |
| SNORD13 | 0.00409278 | −1.87394 | — |
| UNQ2550 | 0.0386757 | −1.97314 | — |
| CLEC4D | 0.168864 | −2.03025 | — |
| STAP1 | 0.211401 | −2.03524 | — |
| CYP4F3LP | 0.0584598 | −2.37697 | — |
| SAA1 | 0.0988763 | −2.42023 | — |
| IL6 | 0.167391 | −4.90534 | — |

Human α-Defensin-5 Levels are Aberrant in Indeterminate Colitis and Restorative Proctocolectomy Operated Patients In order to determine if HD5 could be used to assess whether IC patients could be delineated into a diagnosis of either UC or CC, we assessed levels of HD5 in surgical pathology colectomy samples via IHC in patients described in FIG. 1A. In each instance of a final diagnosis of CC, HD5 high NEARAS counts were in agreement with that diagnosis. We also found that when the 6 patients with unchanged IC diagnoses were analyzed via HD5 IHC NEARAS profile tests, 3 showed high HD5 count and agreed with the final diagnosis of CC, and 3 showed low HD5 count and were in agreement with the final diagnosis of UC (Table 4, as shown in FIG. 13). Table 4 shows that IHC staining for HD5 agrees with final diagnostic outcome in a sample of IC patients even when there was no agreement with the attending physician.

Figure 8A:
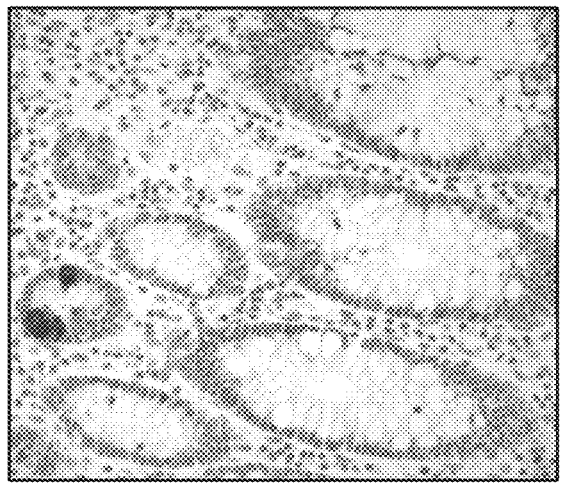
FIGS. 8A-D illustrate that it is possible to use DEFA5 (HD5) to determine patient candidacy for IPAA. 8A=Representative results from a RPC-operated patient that did not change the diagnosis after surgery and was molecularly tested using DEFA5 (HD5) IHC. 8B=Representative results from a UC RPC and IPAA operated patients that did change the diagnosis from UC to de novo Crohn's was molecularly tested using DEFA5 (HD5) IHC. C. NL-Ileum, control. 8D=Quantification of NEARAS DEFA5 (HD5) IHC staining spot counts for UC RPC and IPAA-operated patients who did not have their original diagnosis changed versus those who did change from UC to de novo Crohn's. (Ctrl 1 Destaining control, UC=Ulcerative Colitis, CC=Crohn's Colitis, DV=Diverticulitis, DVL=Diverticulosis).
Figure 8B:
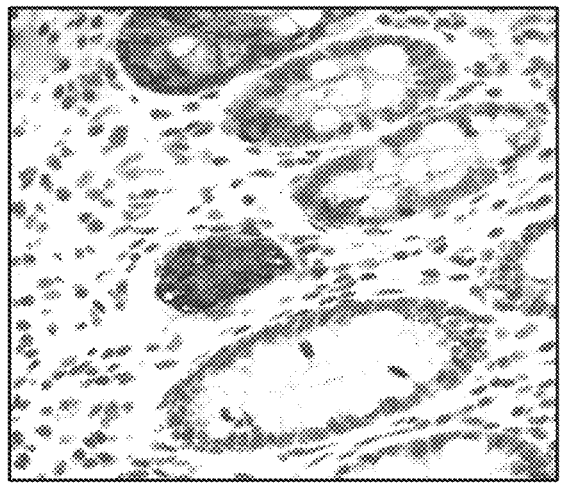

Further, RPC and IPAA-operated patients described in FIG. 1B who had a clinical change in diagnosis to de novo Crohn's (n=20) and those whose diagnoses did not change (n=47) were also analyzed molecularly for HD5 levels via NEARAS IHC counts. The patients whose diagnosis remained unchanged showed only trace levels of HD5 (FIG. 8A). Patients whose diagnoses clinically changed from UC to de novo Crohn's showed prominent HD5 staining (FIG. 8B).

Figure 8C:
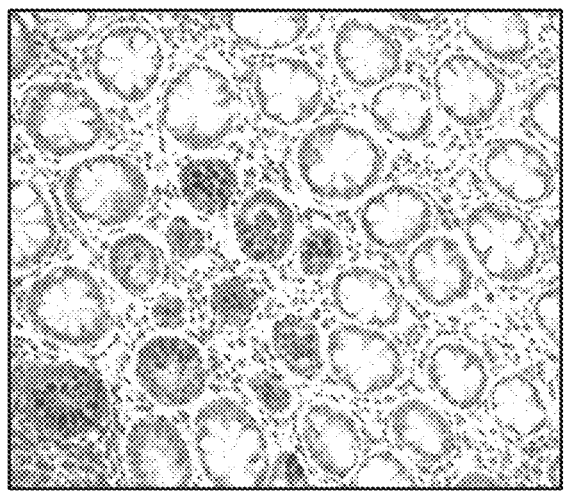
Figure 8D:
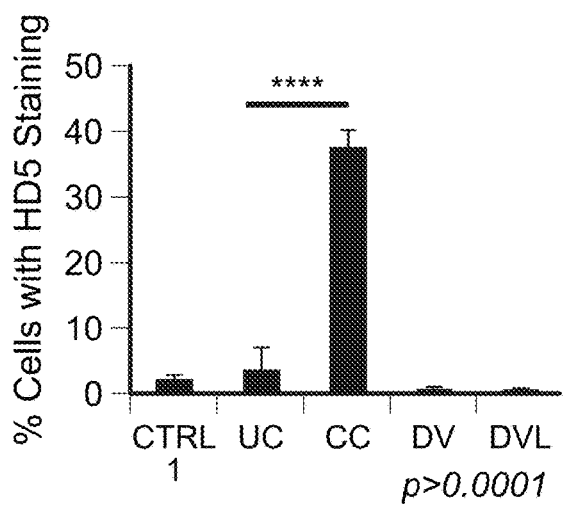

These images can be compared to normal ileum control (FIG. 8C). Differential quantification of HD5 levels by NEARAS counts for UC RPC and IPAA-operated patients who did not have their original diagnoses changed vs. those with de novo Crohn's (FIG. 8A vs. 3B) were statistically significant (p<0.0001) (FIG. 8D). In addition, statistical analysis to determine positive predictive values (PPVs) of HD5 in patient tissue are 95.8% for CC and only 76.9% for UC. Chi squared analysis shows significant relatedness between high levels of HD5 and a diagnosis of CC (p<0.0001). These data indicate that HD5 could be developed into a diagnostic tool to better distinguish CC from UC.

Figure 9A:
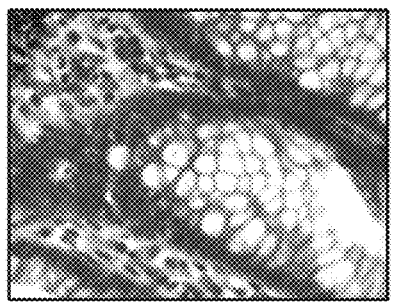
FIGS. 9A-I illustrate H&E staining on parallel sections the typical morphological appearance of Paneth cell (PCs) including the presence of dense apical eosinophilic granules. Upper panel: 9A, Diverticulitis (DV, no PCs), 9B, Diverticulosis (DVL, no PCs), 9C, Normal (NL-Colon, Control, no PCs). Middle panel: 9D, UC (found prodromal PC in one patient, arrow). 9E, CC, demonstrate abundance of PCs allover colonic basal crypts (arrows). 9F, Normal (NL-Ileum, Control), with abundance of PCs. Lower panel: IHC detection of Paneth cell markers α-defensin 5 (DEFA5) and lysozyme (LYZ) in the colon. 9G, NL-Colon, 9H, CC, and 9I, NL-Ileum, Control.
Figure 9B:
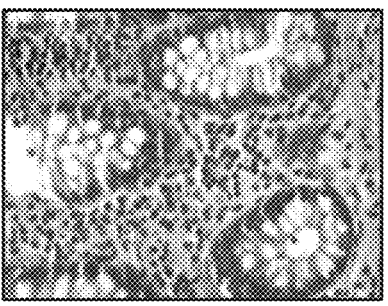
Figure 9C:
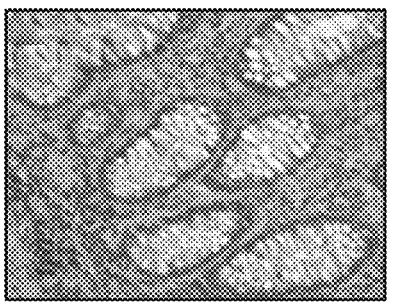
Figure 9D:
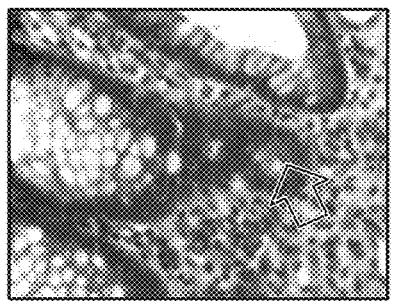
Figure 9E:
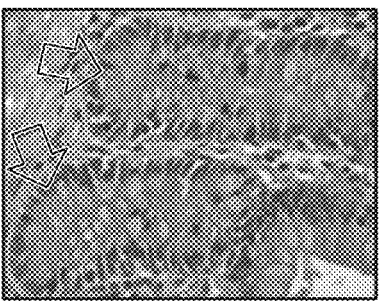
Figure 9F:
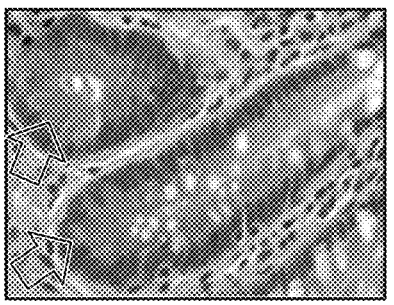
Figure 9G:
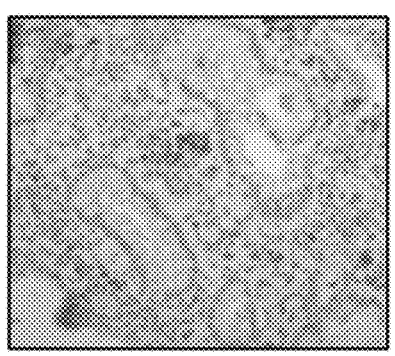
Figure 9H:
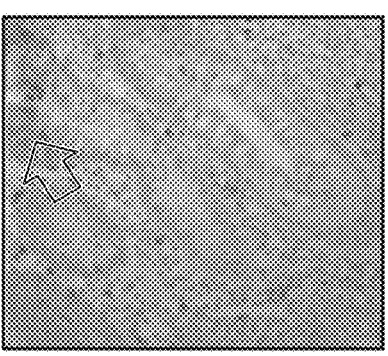
Figure 9I:
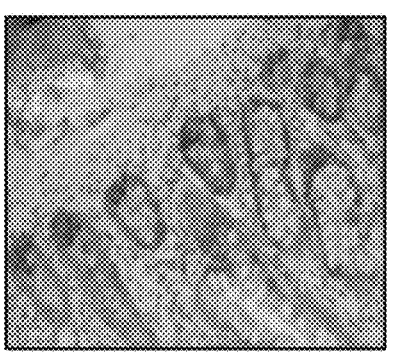
Figure 10A:
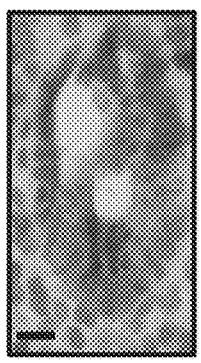
FIGS. 10A-J illustrate a double stain of PCs, lyzosomes and DEFA5 (HD5). Double staining analyses from de novo Crohn's (10A and 10D), and normal ileum/control (10G) are presented. Image deconvolutions are displayed vertically to evaluate lysozyme-specific permanent red (10B, 10E and 10H) and HD5α-specific DAB (FIGS. 10C, 10F, and 10I). The normal colon image (FIG. 10J), which lacks PCs, was not further processed.
Figure 10D:
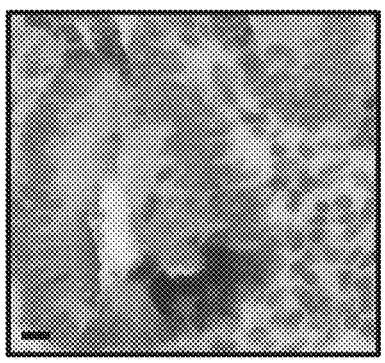
Figure 10G:
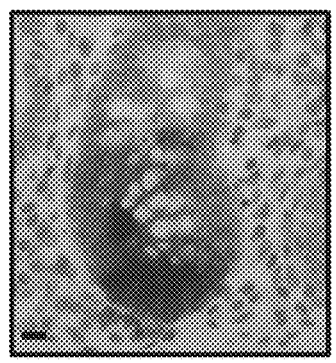
Figure 10B:
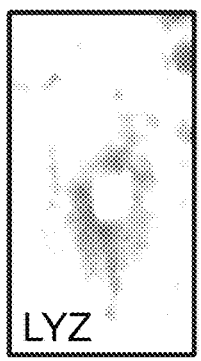
Figure 10E:
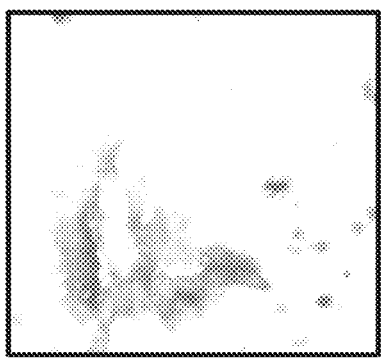
Figure 10H:
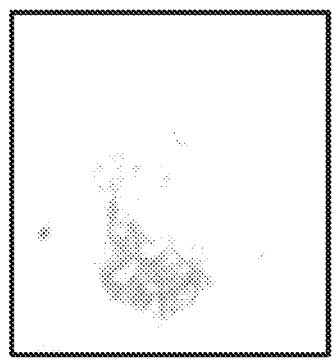
Figure 10C:
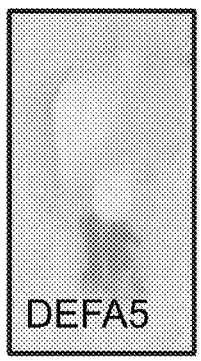
Figure 10F:
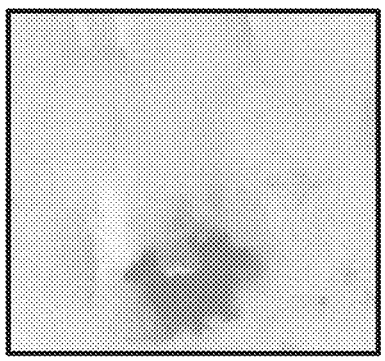
Figure 10I:
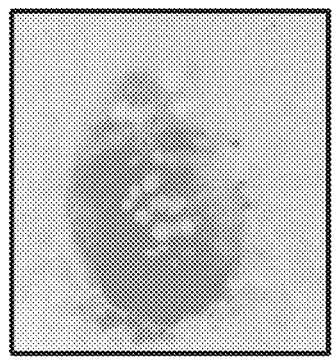
Figure 10J:
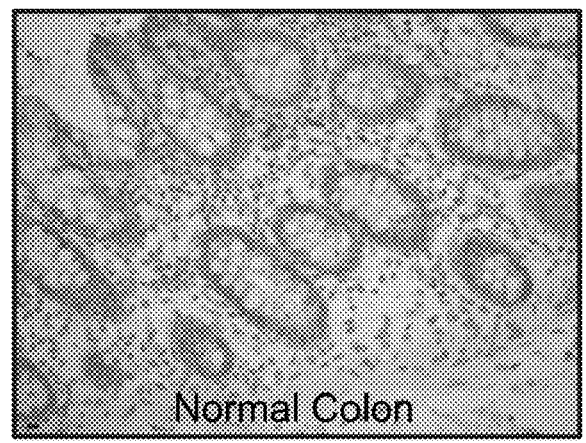
Figure 11A:
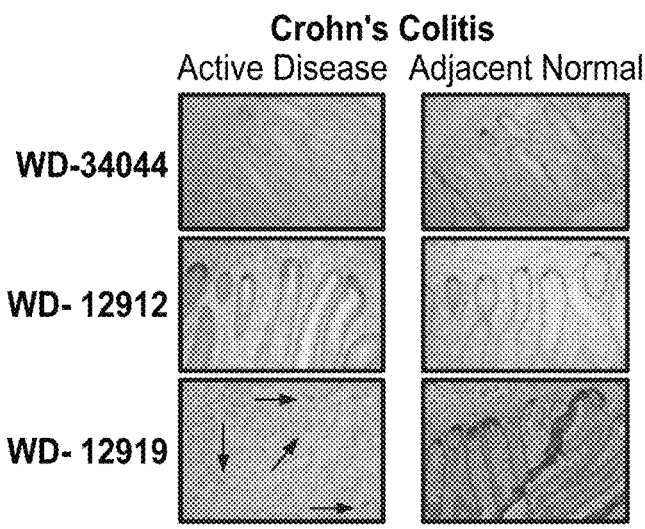
FIGS. 11A-D illustrate an assessment of DEFA5 (HD5) and Paneth cells in inflamed and normal, adjacent tissue. DEFA5 (HD)5 staining of CC inflamed and normal, adjacent tissue shows expression of DEFA5 (HD5) in all patient samples examined (FIG. 11A), compared to inflamed and adjacent, normal tissue of UC patients (FIG. 11B). H&E stains for Paneth Cells (FIGS. 11C and 11D), were negative for PCs in all tissues.
Figure 11B:
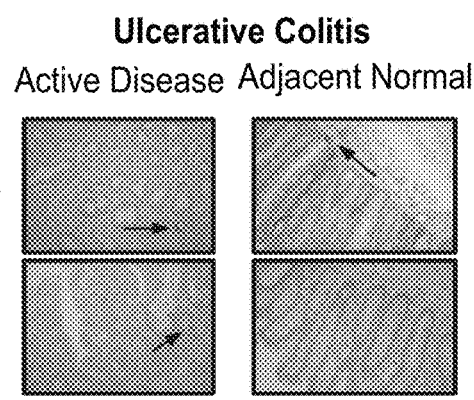
Figure 11C:
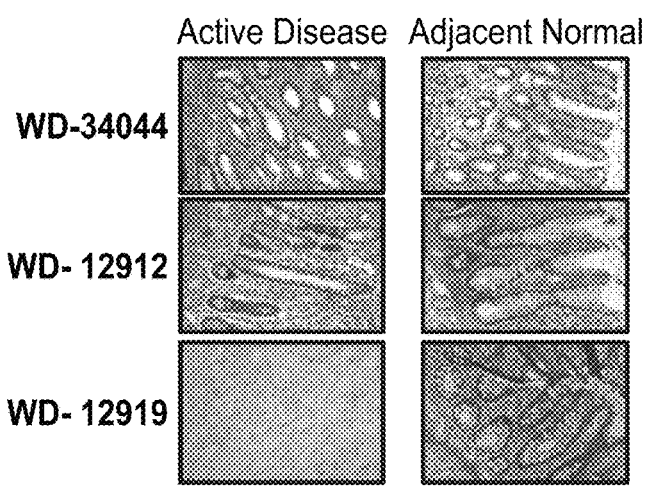
Figure 11D:
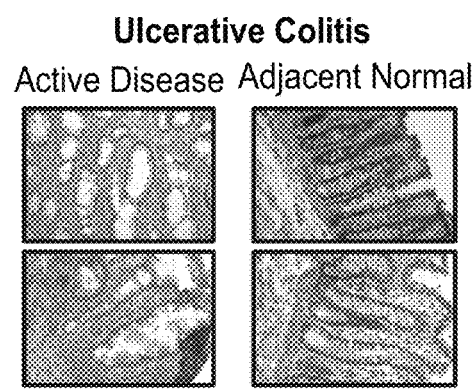
Figure 12A:
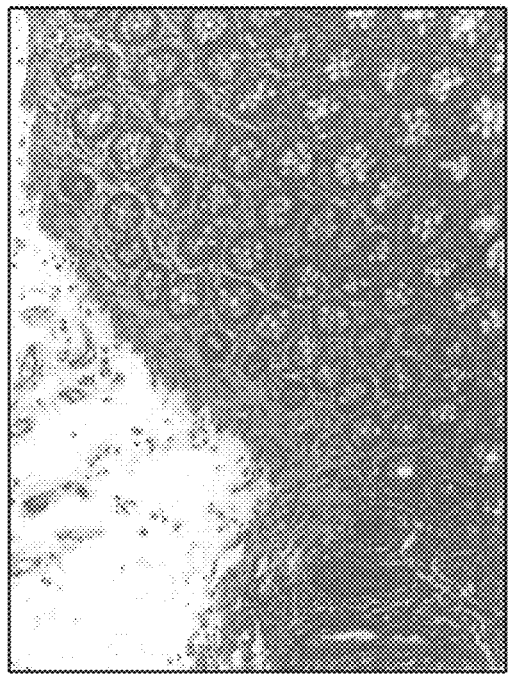
FIGS. 12A-D show histological staining of colon tissue in various subjects. 12A=CC, 12B=UC, 12C=diverticulitis, 12D=normal colon.
Figure 12B:
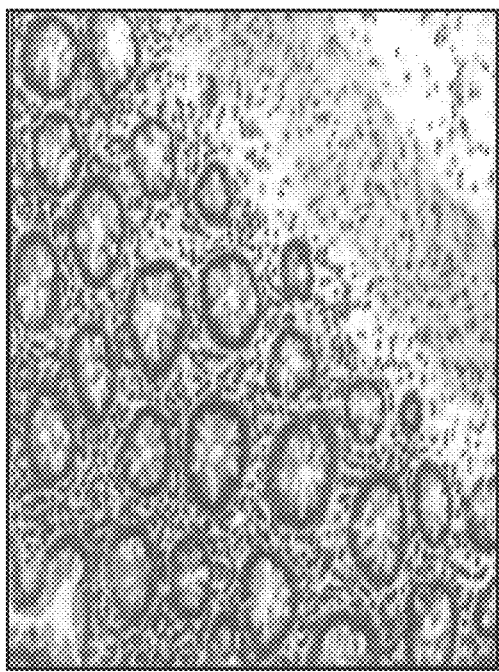
Figure 12C:
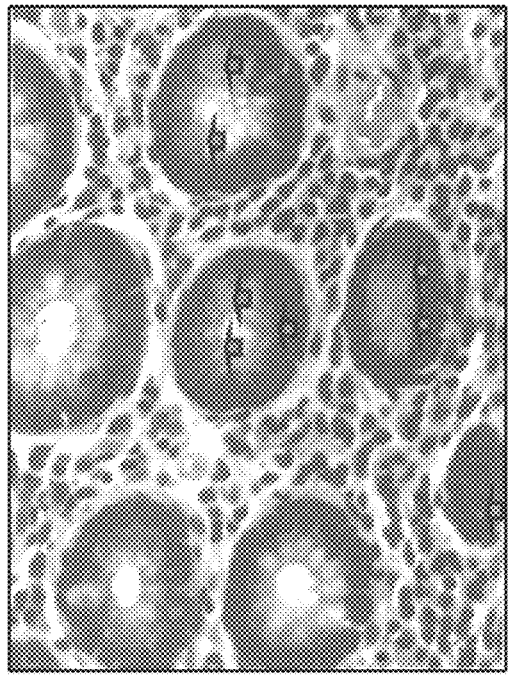
Figure 12D:
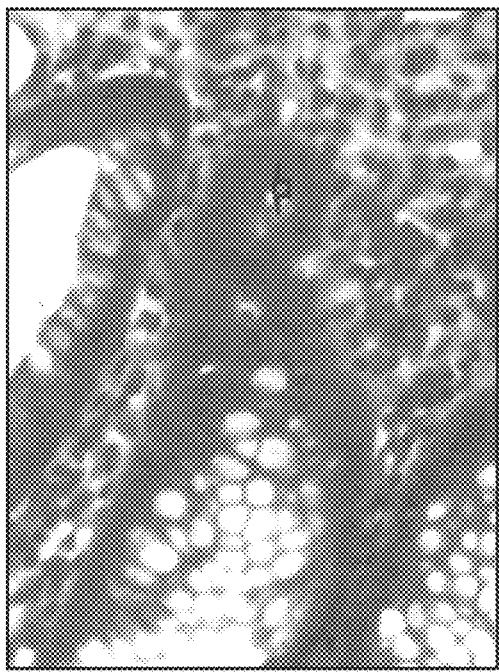

Aberrantly Regulated Human α-Defensin-5 in Crohn's Colitis Patients May be Caused by Ectopic Colonic Crypt Paneth Cells HD5 is a Paneth cell product; therefore, we wanted to determine if Paneth cells were present in the colon crypt of Crohn's colitis patients. All 20 UC RPC operated patients with de novo Crohn's showed pools of ectopic crypt PCs in the colectomy samples, as demonstrated by H&E representative photomicrography (FIG. 9E). This was validated by IHC labeling of PCs using lysozyme by microscopy, which confirmed the abundant presence of PCs in CC colonic crypts (FIG. 9H, arrow). To validate whether the pool of HD5 expressed in CC and in de novo Crohn's colectomy samples was indeed coming from colonic epithelial crypt PCs, we used immunohistochemically detection of PC markers α-Defensin 5 (DEFA5) and lysozyme (LYZ) and double staining IHC to colocalize PCs and HD5 on colectomy samples. Lysozyme alone detects PCs. We demonstrate the presence of abundant crypt PCs in CC colectomy patients (FIG. 9H) compared to all other colonic conditions analyzed (UC, DV, DVL and NL). Further, double staining analyses from de novo Crohn's (FIGS. 10A and 5D), normal colon (FIG. 10J) and normal-ileum/control (FIG. 10G) are presented. Image deconvolutions are displayed vertically to evaluate lysozyme-specific permanent red (FIGS. 10B, 5E and 5H) and HD5-specific DAB (FIGS. 10C, 5F and 5I). The normal colon image (FIG. 10J), which lacks PCs, was not further processed. The results reconcile and represent a consensus among treating physicians.

Human α-Defensin-5 (DEFA5) is a Better Candidate Biomarker than Paneth Cells for Crohn's Colitis.

Figure 6A:
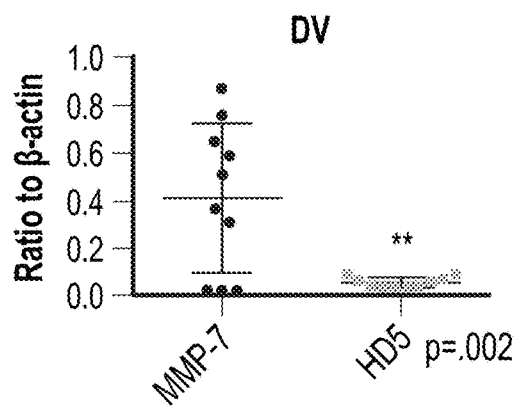
FIGS. 6A-G show a series of plot graphs quantifying and comparing western blot DEFA5 (HD5) and MMP-7 levels in control, diverticulitis, UC, and CC subjects. 6A=diverticulitis, 6B=mild UC, 6C=moderate UC, 6D=severe UC, 6E=mild CC, 6F=moderate CC, and 6G=severe CC.
Figure 6B:
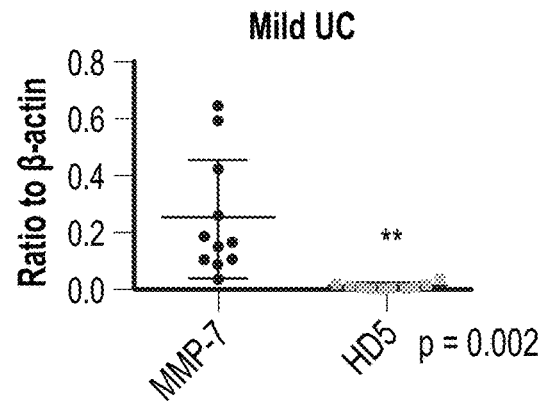
Figure 6C:
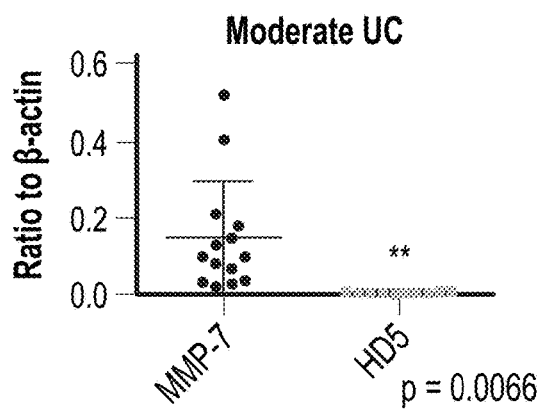
Figure 6D:
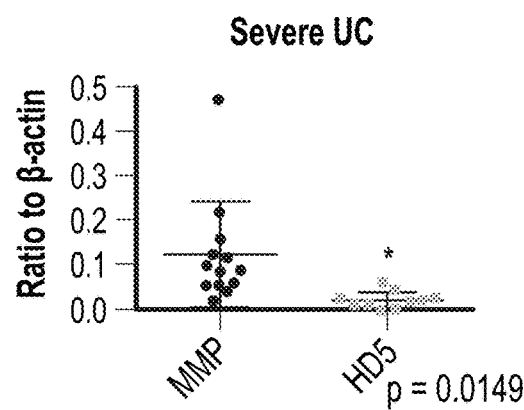
Figure 6E:
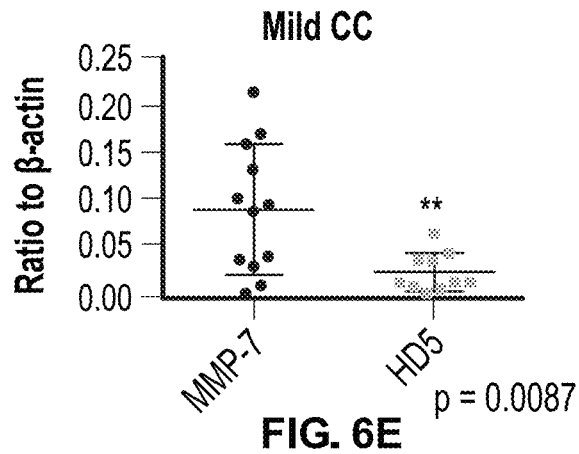
Figure 6F:
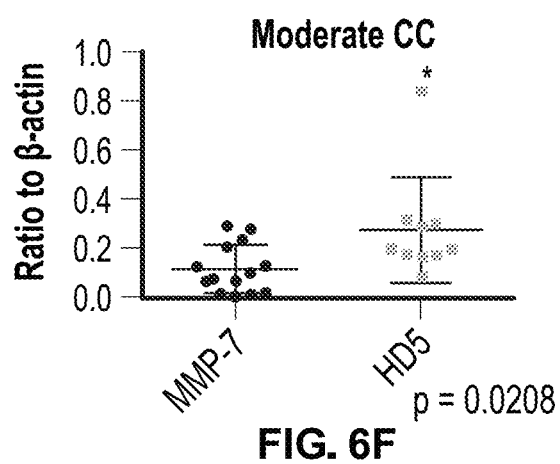
Figure 6G:
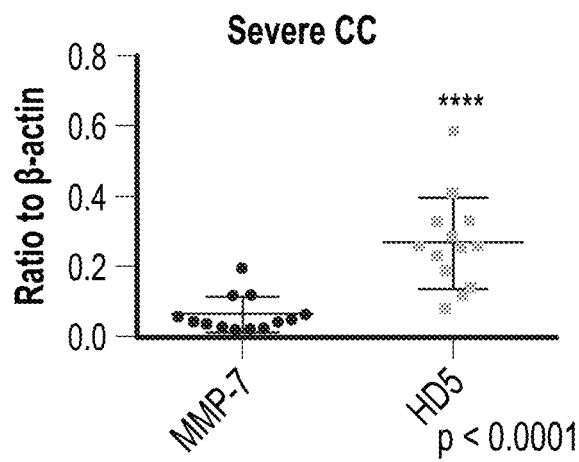

Finally, we sought to determine if HD5 and Paneth cells were both upregulated in the normal, adjacent tissue of CC patients compared to UC patients (FIG. 11). Immunohistochemistry for HD5 shows positive staining in the base of the crypts in both inflamed and normal, adjacent tissue of CC patient samples (FIG. 11A). We were even able to see some positive HD5 staining when the crypt structure is abolished due to excessive inflammation and tissue damage (FIG. 11A, patient WD-12919, arrows). Unsurprisingly, in UC tissue, we saw either very low levels of HD5 or no expression at all (FIG. 11B). We were very surprised, however, to find that we could not see any Paneth cells in either the inflamed or normal adjacent tissues of any of the CC or UC patients surveyed (CC, n=3; UC, n=2) (FIGS. 11C and 6D). These results are surprising, considering our earlier experiments surveying Paneth cells in a larger number of patients (FIG. 9). Because we can detect HD5 in the normal, adjacent tissue more readily than visualize Paneth cells, we believe that HD5 will serve as a better candidate biomarker than Paneth cells for CC.

Studies of MMP-7

Semi-quantitative real-time PCR (qPCR) was used to measure transcript levels of MMP-7. To do this, RNA was extracted from three human colon biopsy samples per condition; three each from moderate UC and CC, and from DV biopsy samples as a non-IBD control using the Qiagen RNeasy Miniprep Kit, (Valencia, Calif.). cDNA was generated using the iScript cDNA synthesis kit (Bio-Rad, Hercules, Calif.), then used in the qPCR reactions using pre-designed TaqMan probes for MMP-7, and GAPHD control, and universal PCR master mix (Thermo Fisher Scientific, Waltham, Mass.). The reactions were run in triplicate using a CFX96 real-time PCR thermocycler (Bio-Rad). Data were analyzed according to the $\Delta\Delta Ct$ method.

To assess any differences in the expression of HD5 and MMP-7 at the protein level, colon surgical resections (n=10) were used from mild, moderate, and severe UC; mild, moderate, and severe CC; and non-IBD DV control. Whole tissue protein extracts were prepared from full-thickness colon samples (n=10) using T-PER protein extraction kit according to manufacturer's protocol (Thermo Fisher Scientific). Bradford Assays (Bio-Rad) were used to determine protein concentration, and equal amounts of protein were separated in 4-20% SDS-PAGE tris/glycine gel (sodium dodecyl sulphate-polyacrylamide gel electrophoresis) (Bio-Rad), then transferred to PVDF (polyvinylidene difluoride) membranes (Bio-Rad). The membranes were probed with antibodies against HD5, MMP-7, and β-actin loading control according to manufacturer's protocol. Blots were visualized with Opti-4CN colorimetric detection kit (Bio-Rad) and imaged with ChemiDoc XRS+imaging system (Bio-Rad). Band intensities were measured and data analysis performed with Image Lab Software (Bio-Rad).

Figure 3:
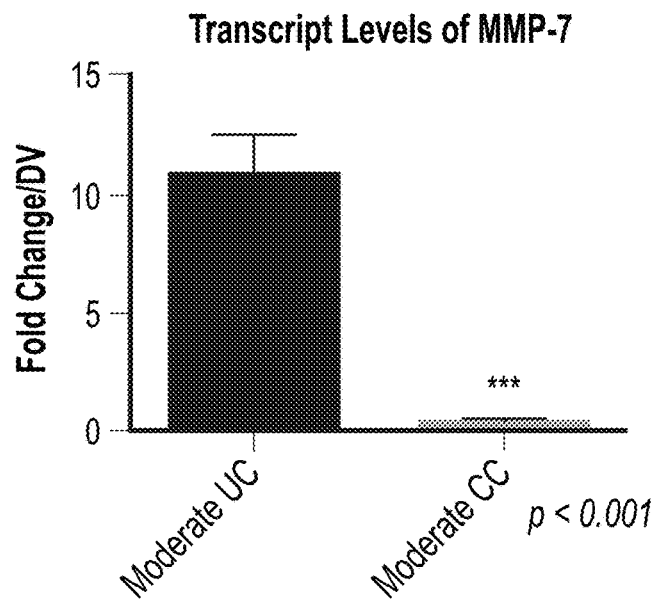
FIG. 3 is a bar graph showing differentially expressed MMP-7 in UC subjects as compared to CC subjects.
Figure 4:
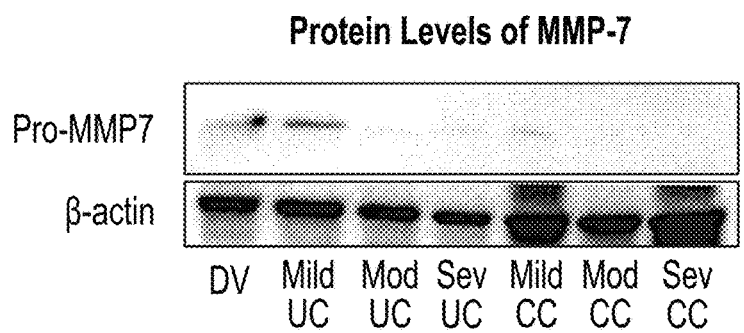
FIG. 4 is a western blot analysis of MMP-7 levels in diverticulitis, UC, and CC subjects.
Figure 5:
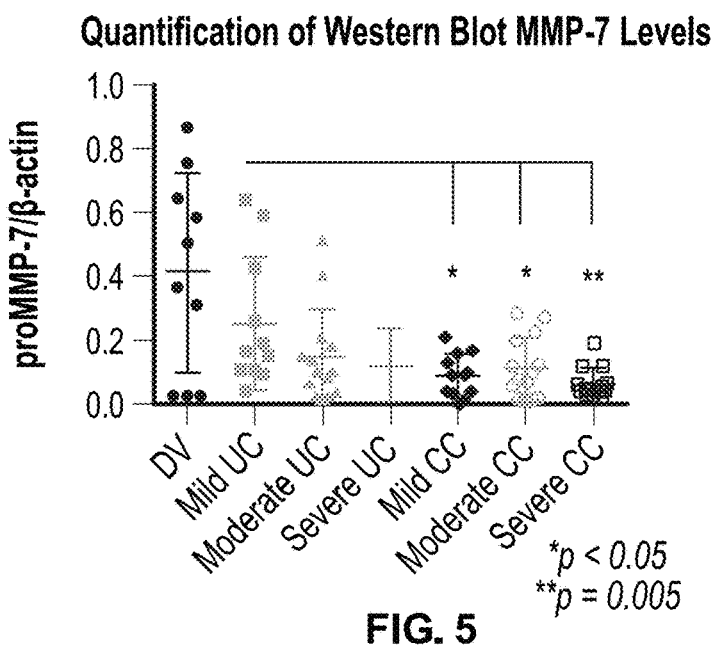
FIG. 5 is a plot graph quantifying the western blot MMP-7 levels of FIG. 4.

FIG. 3 is a bar graph of a qRT-PCR result showing a decrease in MMP-7 levels in moderate CC compared to moderate UC, the inverse of HD5 levels (p<0.001). Western blot data for all disease states (n≥10) shows a decrease in MMP-7 levels in CC compared to UC, significant when moderate and severe CC is compared to mild UC. FIG. 4 is a representative western blot of MMP-7 in subjects having IBD. Expression of HD5 in IBD tissues was examined by IHC using FFPE thin sections. MMP-7 levels (top) appear to decrease progressing from left to right. β-actin loading control is shown on bottom. FIG. 5 is a graphical representation of MMP-7 levels shown in FIG. 3. Band intensities were measured and normalized to β-actin loading control. Moderate and severe CC are statistically significant when compared to mild UC (p<0.05 and p<0.005, respectively). FIGS. 8A-G are graphical representations showing MMP-7 and HD5 levels are inversely expressed in IBD. Patient samples were matched and levels of HD5 and MMP-7 were compared. In all disease states, MMP-7 and HD5 levels are inversely expressed, and all differences are statistically significant. As MMP-7 levels decrease, HD5 levels increase.

Discussion

Colectomy surgical pathology samples of patients with unambiguous CC and UC undergoing colectomy in connection with RPC and IPAA were analyzed [6, 7]. We those protein profiles which had the necessary (i) specificity; (ii) sensitivity; (iii) discriminatory; and (iv) predictive capacity to determine the heterogeneity of IBD [6, 7] were identified and compared. It was possible to molecularly delineate UC and CC with molecular signatures of HD5 using IHC and quantified by NEARAS. Alpha-Defensins HD5 and HD6 are PC products and their altered expression has been linked to IBD pathogenesis.

It was not expected that one could not visualize PCs in these tissues even though one could detect HD5 in the same tissue (FIG. 2H), especially compared to earlier experiments showing high levels of PCs in all CC patients surveyed (FIG. 2C). Whether the PCs are essential for stem cell maintenance in vivo remains debatable [27].

To date, there is no diagnostic gold standard tool for IBD. Differentiating UC and CC among patients with IC has remained painstaking and is a major challenge in endoscopic medicine and colorectal surgery [1, 12, 28, 29]. Clinicians use an inexact classification system of clinical, endoscopy, radiologic, and histopathology findings in order to diagnose CC and UC [21, 30, 31]. Even with a combination of these diagnostic modalities, up to 15% of IBD patients are labeled as IC when no definitive evaluations can be made [13, 30, 32]. In addition, CC is mistakenly diagnosed and RPC and IPAA-operated as definitive UC in another 15% of IBD patients because of overlap in the clinical, endoscopic, radiological and histologic findings [12, 33-36]. Further, most IC patients who undergo RPC and IPAA surgery for presumed UC are subsequently found to develop a recurrent de novo Crohn's disease in the ileal pouch [1, 12, 33]. This is a serious consequence that may hinder the restoration of intestinal continuity and its intractable nature leads to pouch failure, often requiring pouch diversion or excision with a permanent terminal-ileostomy, resulting in negative psycho-sociological implications and poorer quality of life [1, 29, 31, 36-41]. Curative treatment for UC is often surgical [42].

Success of RPC and IPAA surgery is largely dependent on careful patient selection combined with meticulous surgical technique and diagnostic accuracy [9-11, 13]. Available clinical presentations and experience suggest that it is difficult to identify patients with CC who are likely to have a successful outcome after RPC and IPAA surgery [10, 13, 34, 43]. However, in highly selected patients with CC, RPC and IPAA has been indicated [44-47]. Thus, RPC operation may be considered and should remain a careful option for certain subgroup of patients with CC, but an acceptable care option for patients with UC and for those IC patients predicted to develop UC [9, 42].

These studies of HD5 as a candidate biomarker for CC suggest it could be a diagnostic signature to efficiently distinguish CC from UC. Newly published data shows that patients with small bowel Crohn's disease (Crohn's ileitis) are characterized with a deficiency of HD5, as shown by a reduced expression and secretion of the Paneth cell HD5, a fundamental feature of Crohn's ileitis [48-51]. Based on this study, in CC, the reverse is true. It was found that Paneth cell HD5 is a predominantly expressed antimicrobial peptide. This indicates that definitive CC and Crohn's ileitis may have distinct etiologies and mechanisms. In these studies, all IC patient samples have been reconciled into UC and CC using molecular biomarker, HD5, and verified the reconciliation by patient outcomes (FIGS. 1 and 13 (Table 4)).

Accurately distinguishing CC from UC is of utmost importance when determining the candidacy of a patient for RPC [1, 42]. Early diagnostic accuracy of IBD will lead to timely appropriate medical options. This study confirms that HD5 can differentiate CC and UC and reclassify IC into CC. In addition to distinguishing the colitides, HD5 could objectively be used to evaluate biophysiological processes and therapeutic outcomes and potentially play a pivotal role in IBD clinics as an attractive, non-invasive avenue [52, 53].

Thus, this working example shows that tissue samples taken from patients suffering from CD have levels of HD5 significantly higher than the HD5 levels in samples from patients suffering from UC. Additionally, this working example shows that samples taken from patients suffering from CD have levels of MMP-7 significantly lower than the MMP-7 levels in samples of patients suffering from UC.

REFERENCES

The following references were cited in the above working example. Such citation is not to be construed as an admission that any reference meets the legal definition of "prior art" in any country, nor as an admission that any reference is relevant to the patentability of anything claimed. Any such reference shall be incorporated herein by reference only to the extent it is necessary for a person of ordinary skill in the art to make and use anything claimed.

1. Jackson K L, Stocchi L, Duraes L, Rencuzogullari A, Bennett A E, Remzi F H. Long-Term Outcomes in Indeterminate Colitis Patients Undergoing Ileal Pouch-Anal Anastomosis: Function, Quality of Life, and Complications. J Gastrointest Surg 2017; 21:56-61. https://doi.org/10.1007/s11605-016-3306-9 PMID: 27832426
2. Carvalho R S, Abadom V, Dilworth H P, Thompson R, Oliva-Hemker M, Cuffari C. Indeterminate colitis: a significant subgroup of pediatric IBD. Inflamm Bowel Dis 2006; 12:258-62. https://doi.org/10.1097/01.MIB.0000215093.62245. b9 PMID: 16633047
3. Cantoro L, Di Sabatino A, Papi C, Margagnoni G, Ardizzone S, Giuffrida P, et al. The time course of diagnostic delay in inflammatory bowel disease over the last sixty years: an Italian multicenter study. J Crohn's Colitis 2017 Mar. 18 [Epub ahead of print].
4. Clark C, Turner J. Diagnostic Modalities for Inflammatory Bowel Disease: Serologic Markers and Endoscopy. Surg Clin North Am 2015; 95:1123-41. https://doi.org/10.1016/j.suc.2015.07.008 PMID: 26596918
5. Odze R D. A contemporary and critical appraisal of 'indeterminate colitis'. Mod Pathol 2015; 28 Suppl 1:S30-46.
6. M'Koma A E, Seeley E H, Washington M K, Schwartz D A, Muldoon R L, Herline A J, et al. Proteomic profiling of mucosal and submucosal colonic tissues yields protein signatures that differentiate the inflammatory colitides. Inflamm Bowel Dis 2011; 17:875-83. https://doi.org/10.1002/ibd.21442 PMID: 20806340
7. Seeley E H, Washington M K, Caprioli R M, M'Koma A E. Proteomic patterns of colonic mucosal tissues delineate Crohn's colitis and ulcerative colitis. Proteomics Clin Appl 2013; 7:541-9. https://doi.org/10.1002/prca.201200107 PMID: 23382084
8. M'Koma A E, Blum D L, Norris J L, Koyama T, Billheimer D, Motley S, et al. Detection of pre-neoplastic and neoplastic prostate disease by MALDI profiling of urine. Biochem Biophys Res Commun 2007; 353:829-34. https://doi.org/10.1016/j.bbrc.2006.12.111 PMID: 17194448
9. M'Koma A E, Wise P E, Muldoon R L, Schwartz D A, Washington M K, Herline A J. Evolution of the restorative proctocolectomy and its effects on gastrointestinal hormones. Int J Colorectal Dis 2007; 22:1143-63. https://doi.org/10.1007/s00384-007-0331-x PMID: 17576578
10. Shen B, Remzi F H, Brzezinski A, Lopez R, Bennett A E, Lavery I C, et al. Risk factors for pouch failure in patients with different phenotypes of Crohn's disease of the pouch. Inflamm Bowel Dis 2008; 14:942-8. https://doi.org/10.1002/ibd.20409 PMID: 18300279
11. Shen B, Remzi F H, Lavery I C, Lashner B A, Fazio V W. A proposed classification of ileal pouch disorders and associated complications after restorative proctocolectomy. Clin Gastroenterol Hepatol 2008; 6:145-58. https://doi.org/10.1016/j.cgh.2007.11.006 PMID: 18237865
12. Zaghiyan K, Kaminski J P, Barmparas G, Fleshner P. De novo Crohn's Disease after Ileal Pouch-Anal Anastomosis for Ulcerative Colitis and Inflammatory Bowel Disease Unclassified: Long-Term Follow-Up of a Prospective Inflammatory Bowel Disease Registry. Am Surg 2016; 82:977-81. PMID: 27779987
13. Shen B. Crohn's disease of the ileal pouch: reality, diagnosis, and management. Inflamm Bowel Dis 2009; 15:284-94. https://doi.org/10.1002/ibd.20661 PMID: 18816633
14. Lee H S, Choe J, Lee H J, Hwang S W, Park S H, Yang D H, et al. Change in the diagnosis of inflammatory bowel disease: a hospital-based cohort study from Korea. Intest Res 2016; 14:258-63. https://doi.org/10.5217/ir.2016.14.3.258 PMID: 27433148
15. Nakamura K, Sakuragi N, Takakuwa A, Ayabe T. Paneth cell alpha-defensins and enteric microbiota in health and disease. Biosci Microbiota Food Health 2016; 35:57-67. https://doi.org/10.12938/bmfh. 2015-019 PMID: 27200259
16. Durand A, Donahue B, Peignon G, Letourneur F, Cagnard N, Slomianny C, et al. Functional intestinal stem cells after Paneth cell ablation induced by the loss of transcription factor Math1 (Atoh1). Proc Natl Acad Sci USA 2012; 109:8965-70. https://doi.org/10.1073/pnas.1201652109 PMID: 22586121
17. Li X, LeBlanc J, Elashoff D, McHardy I, Tong M, Roth B, et al. Microgeographic Proteomic Networks of the Human Colonic Mucosa and Their Association With Inflammatory Bowel Disease. Cell Mol Gastroenterol Hepatol 2016; 2:567-83. https://doi.org/10.1016/j.jcmgh.2016.05.003 PMID: 28174738
18. VanDussen K L, Liu T C, Li D, Towfic F, Modiano N, Winter R, et al. Genetic variants synthesize to produce paneth cell phenotypes that define subtypes of Crohn's disease. Gastroenterology 2014; 146:200-9. https://doi.org/10.1053/j.gastro.2013.09.048 PMID: 24076061
19. Lawrance I C, Fiocchi C, Chakravarti S. Ulcerative colitis and Crohn's disease: distinctive gene expression profiles and novel susceptibility candidate genes. Hum Mol Genet 2001; 10:445-56. PMID: 11181568
20. Puri K S, Suresh K R, Gogtay N J, Thatte U M. Declaration of Helsinki, 2008: implications for stakeholders in research. J Postgrad Med 2009; 55:131-4. https://doi.org/10.4103/0022-3859.52846 PMID: 19550060
21. Targan S R, Karp L C. Inflammatory bowel disease diagnosis, evaluation and classification: state-of-the art approach. Curr Opin Gastroenterol 2007; 23:390-4. https://doi.org/10.1097/MOG. 0b013e3281722271 PMID: 17545774
22. James S D, Wise P E, Zuluaga-Toro T, Schwartz D A, Washington M K, Shi C. Identification of pathologic features associated with "ulcerative colitis-like" Crohn's disease. World J Gastroenterol 2014; 20:13139-45. https://doi.org/10.3748/wjg.v20.i36.13139 PMID: 25278708
23. Jong V L, Novianti P W, Roes K C, Eijkemans M J. Selecting a classification function for class prediction with gene expression data. Bioinformatics 2016; 32:1814-22. https://doi.org/10.1093/bioinformatics/btw034 PMID: 26873933
24. Myers J N, Schaffer M W, Korolkova O Y, Williams A D, Gangula P R, M'Koma A E. Implications of the Colonic Deposition of Free Hemoglobin-alpha Chain: A Previously Unknown Tissue By-product in Inflammatory Bowel Disease. Inflamm Bowel Dis 2014; 20:1530-47. https://doi.org/10.1097/MIB. 0000000000000144 PMID: 25078150
25. Gmyr V, Bonner C, Lukowiak B, Pawlowski V, Dellaleau N, Belaich S, et al. Automated digital image analysis of islet cell mass using Nikon's inverted eclipse Ti microscope and software to improve engraftment may help to advance the therapeutic efficacy and accessibility of islet transplantation across centers. Cell Transplant 2015; 24:1-9. https://doi.org/10.3727/096368913X667493 PMID: 23683575
26. Tulay P, Naja R P, Cascales-Roman O, Doshi A, Serhal P, SenGupta S B. Investigation of microRNA expression and DNA repair gene transcripts in human oocytes and blastocysts. J Assist Reprod Genet 2015; 32:1757-64. https://doi.org/10.1007/s10815-015-0585-0 PMID: 26438643
27. Farin H F, Karthaus W R, Kujala P, Rakhshandehroo M, Schwank G, Vries R G, et al. Paneth cell extrusion and release of antimicrobial products is directly controlled by immune cell-derived IFN-gamma. J Exp Med 2014; 211: 1393-405. https://doi.org/10.1084/jem.20130753 PMID: 24980747
28. Ballard B R, M'Koma A E. Gastrointestinal endoscopy biopsy derived proteomic patterns predict indeterminate colitis into ulcerative colitis and Crohn's colitis. World J Gastrointest Endos 2015; 7:670-4.
29. Zaharie R, Tantau A, Zaharie F, Tantau M, Gheorghe L, Gheorghe C, et al. Diagnostic Delay in Romanian Patients with Inflammatory Bowel Disease: Risk Factors and Impact on the Disease Course and Need for Surgery. J Crohn's Colitis 2016; 10:306-14.
30. M'Koma A E. Diagnosis of inflammatory bowel disease: Potential role of molecular biometrics. World J Gastrointest Surg 2014; 6:208-19. https://doi.org/10.4240/wjgs.v6.i11.208 PMID: 25429322
31. Matsui T. [Diagnosis of inflammatory bowel diseases. 1. Diagnosis, disease type and severity classification]. Nihon Naika Gakkai Zasshi 2009; 98:31-6. PMID: 19334353
32. Feakins R M. Ulcerative colitis or Crohn's disease? Pitfalls and problems. Histopathology 2014; 64:317-35. https://doi.org/10.1111/his.12263 PMID: 24266813
33. Gu J, Stocchi L, Kiran R P, Shen B, Remzi F H. Do clinical characteristics of de novo pouch Crohn's disease after restorative proctocolectomy affect ileal pouch retention? Dis Colon Rectum 2014; 57:76-82. https://doi.org/10.1097/01.dcr.0000437691.52109.f2 PMID: 24316949
34. Wagner-Bartak N A, Levine M S, Rubesin S E, Laufer I, Rombeau J L, Lichtenstein G R. Crohn's disease in the ileal pouch after total colectomy for ulcerative colitis: findings on pouch enemas in six patients. AJR Am J Roentgenol 2005; 184:1843-7. https://doi.org/10.2214/ajr.184.6.01841843 PMID: 15908540
35. Price A B. Overlap in the spectrum of non-specific inflammatory bowel disease—'colitis indeterminate'. J Clin Pathol 1978; 31:567-77. PMID: 670413
36. Langner C, Aust D, Ensari A, Villanacci V, Becheanu G, Miehlke S, et al. Histology of microscopic colitis-review with a practical approach for pathologists. Histopathology 2015; 66:613-26. https://doi.org/10.1111/his.12592 PMID: 25381724
37. Langner C, Magro F, Driessen A, Ensari A, Mantzaris G J, Villanacci V, et al. The histopathological approach to inflammatory bowel disease: a practice guide. Virchows Arch 2014; 464:511-27. https://doi.org/10.1007/s00428-014-1543-4 PMID: 24487791
38. Abdelaal K, Jaffray B. Variables associated with loss of ileoanal pouches constructed in childhood. J Pediatr Surg 2017; 52:281-5. https://doi.org/10.1016/j.jpedsurg.2016.11.017 PMID: 27890312
39. Robbins L, Zaghiyan K, Melmed G, et al. Outcomes with Anti-Tumour Necrosis Factor-Alpha Therapy and Serology in Patients with Denovo Crohn's Disease After Ileal Pouch Anal Anastomosis. J Crohn's Colitis 2017; 11:77-83.
40. Das P, Smith J J, Tekkis P P, Heriot A G, Antropoli M, John Nicholls R. Quality of life after indefinite diversion/pouch excision in ileal pouch failure patients. Colorectal Dis 2007; 9:718-24. https://doi.org/10.1111/j.1463-1318.2007.01216.x PMID: 17764535
41. Lepisto A, Luukkonen P, Jarvinen H J. Cumulative failure rate of ileal pouch-anal anastomosis and quality of life after failure. Dis Colon Rectum 2002; 45:1289-94. https://doi.org/10.1097/01.DCR. 0000027032.95753.11 PMID: 12394424
42. Magro F, Gionchetti P, Eliakim R, Ardizzone S, Armuzzi A, Barreiro-de Acosta M, et al. Third European Evidence-Based Consensus on Diagnosis and Management of Ulcerative Colitis. Part 1: Definitions, diagnosis, extra-intestinal manifestations, pregnancy, cancer surveillance, surgery, and ileo-anal pouch disorders. J Crohn's Colitis 2017; 11:649-670
43. Keighley M R. The final diagnosis in pouch patients for presumed ulcerative colitis may change to Crohn's disease: patients should be warned of the consequences. Acta Chir Lugosl 2000; 47:27-31. PMID: 11432239
44. Turina M, Remzi F H. The J-pouch for patients with Crohn's disease and indeterminate colitis: (when) is it an option? J Gastrointest Surg 2014; 18:1343-4. https://doi.org/10.1007/s11605-014-2498-0 PMID: 24777433
45. Le Q, Melmed G, Dubinsky M, McGovern D, Vasiliauskas E A, Murrell Z, et al. Surgical outcome of ileal pouch-anal anastomosis when used intentionally for well-defined Crohn's disease. Inflamm Bowel Dis 2013; 19:30-6. https://doi.org/10.1002/ibd.22955 PMID: 22467562
46. Li Y, Wu B, Shen B. Diagnosis and differential diagnosis of Crohn's disease of the ileal pouch. Curr Gastroenterol Rep 2012; 14:406-13. https://doi.org/10.1007/s11894-012-0282-4 PMID: 22855236
47. Shen B, Patel S, Lian L. Natural history of Crohn's disease in patients who underwent intentional restorative proctocolectomy with ileal pouch-anal anastomosis. Aliment Pharmacol Ther 2010; 31:745-53. https://doi.org/10.1111/j.1365-2036.2009.04227.x PMID: 20047579
48. Courth L F, Ostaff M J, Mailander-Sanchez D, Malek N P, Stange E F, Wehkamp J. Crohn's disease-derived monocytes fail to induce Paneth cell defensins. Proc Natl Acad Sci USA 2015; 112:14000-5. https://doi.org/10.1073/pnas.1510084112 PMID: 26512113
49. Tan G, Zeng B, Zhi F C. Regulation of human enteric alpha-defensins by NOD2 in the Paneth cell lineage. Eur J Cell Biol 2015; 94:60-6. https://doi.org/10.1016/j.ejcb.2014.10.007 PMID: 25433720
50. Wang C, Shen M, Gohain N, Tolbert W D, Chen F, Zhang N, et al. Design of a potent antibiotic peptide based on the active region of human defensin 5. J Med Chem 2015; 58:3083-93. https://doi.org/10.1021/jm501824a PMID: 25782105
51. Hayashi R, Tsuchiya K, Fukushima K, Horita N, Hibiya S, Kitagaki K, et al. Reduced Human alpha-defensin 6 in Noninflamed Jejunal Tissue of Patients with Crohn's Disease. Inflamm Bowel Dis 2016; 22:1119-28. https://doi.org/10.1097/MIB.0000000000000707 PMID: 26891258
52. Wagner J A, Williams S A, Webster C J. Biomarkers and surrogate end points for fit-for-purpose development and regulatory evaluation of new drugs. Clin Pharmacol Ther 2007; 81:104-7. https://doi.org/10.1038/sj.clpt.6100017 PMID: 17186007
53. Vermeire S, Van Assche G, Rutgeerts P. Laboratory markers in IBD: useful, magic, or unnecessary toys? Gut 2006; 55:426-31. https://doi.org/10.1136/gut.2005.069476 PMID: 16474109.

EXEMPLARY EMBODIMENTS

In addition to anything described above or currently claimed, it is specifically contemplated that any of the following embodiments may be claimed:

Emb. 1

A method of measuring HD5 in a patient suffering from or at risk of inflammatory bowel disease (IBD), said method comprising: obtaining a sample from the patient; and measuring at least one of the expression of HD5 and the concentration of HD5 in the sample.

Emb. 2

A method of treating a patient suffering from or at risk of inflammatory bowel disease (IBD), said method comprising: performing the method of measuring HD5 in the patient according to embodiment 1; and performing an intervention on the patient to treat Crohn's disease.

Emb. 3

Any one of the methods of embodiments 1-2, comprising: comparing the expression of HD5 or the concentration of HD5 in the sample to a benchmark value that is typical of a subject not suffering from Crohn's disease; and diagnosing Crohn's disease if the expression of HD5 or the concentration of HD5 in the sample significantly exceeds the benchmark value.

Emb. 4

Any one of the methods of embodiments 1-3, wherein the expression of HD5 or the concentration of HD5 in the sample exceeds a benchmark value that is typical of a subject not suffering from Crohn's disease.

Emb. 5

Any one of the methods of embodiments 1-4, wherein the expression of HD5 is measured to be significantly greater in the sample than in a control sample from a subject not suffering from Crohn's disease.

Emb. 6

Any one of the methods of embodiments 1-5, wherein the expression of HD5 is measured to be at least about 31 times greater in the sample than in a control sample from a subject not suffering from Crohn's disease.

Emb. 7

Any one of the methods of embodiments 1-6, wherein the expression of HD5 is measured to be at least about 118 times greater in the sample than in a control sample from a subject not suffering from Crohn's disease.

Emb. 8

Any one of the methods of embodiments 1-7, wherein the expression of HD5 is measured to be greater than about 106 HD5 mRNA transcripts per 10 ng RNA.

Emb. 9

Any one of the methods of embodiments 1-8, wherein the expression of HD5 is measured to be greater than 107 HD5 mRNA transcripts per 10 ng RNA.

Emb. 10

Any one of the methods of embodiments 1-9, wherein the expression of HD5 is measured to be greater than $1.9 \times 107$ HD5 mRNA transcripts per 10 ng RNA.

Emb. 11

Any one of the methods of embodiments 1-10, wherein the expression of HD5 is measured to be greater than $7 \times 107$ HD5 mRNA transcripts per 10 ng RNA.

Emb. 12

Any one of the methods of embodiments 1-11, wherein the expression of HD5 is measured by qRT-PCR, wherein the method comprises measuring the expression of HD5 mRNA in a control sample from a subject not suffering from Crohn's disease, and wherein the expression of HD5 mRNA in the sample is significantly greater than the expression of HD5 mRNA in the control sample.

Emb. 13

Any one of the methods of embodiments 1-12, wherein the sample is intestinal tissue, and comprising measuring the concentration of HD5 by: immunostaining the sample with an anti-HD5 immunostaining agent; and measuring the percentage of cells in the sample that stain positive; wherein the percentage of cells in the sample that stain positive is at least 10%.

Emb. 14

Any one of the methods of embodiments 1-13, wherein the sample is intestinal tissue, and comprising measuring the concentration of HD5 by: immunostaining the sample with an anti-HD5 immunostaining agent; and measuring the percentage of cells in the sample that stain positive; wherein the percentage of cells in the sample that stain positive is at least 20%.

Emb. 15

Any one of the methods of embodiments 1-14, wherein the sample is intestinal tissue, and comprising measuring the concentration of HD5 by: immunostaining the sample with an anti-HD5 immunostaining agent; and measuring the percentage of cells in the sample that stain positive; wherein the percentage of cells in the sample that stain positive is at least about 30%.

Emb. 16

Any one of the methods of embodiments 1-15, wherein the intervention is not effective to treat ulcerative colitis.

Emb. 17

Any one of the methods of embodiments 1-16, wherein the intervention is a surgery.

Emb. 18

Any one of the methods of embodiments 1-17, wherein the intervention is a surgery selected from the group consisting of: ostomy, colostomy, ileostomy, bowel resection, colectomy, proctocolectomy, and strictureplasty.

Emb. 19

Any one of the methods of embodiments 1-18, wherein the intervention is administration of a drug.

Emb. 20

Any one of the methods of embodiments 1-19, wherein the intervention is administration of a drug, to the exclusion of a surgery.

Emb. 21

Any one of the methods of embodiments 1-20, wherein the intervention is administration of a drug selected from the group consisting of: a vitamin supplement, vitamin B12, vitamin D, a mineral supplement, calcium, an anti-inflammatory, a corticosteroid, a 5-aminosalicylate, an immunosuppressant, azathioprine, mercaptopurine, an anti-TNF-alpha antibody, infliximab, adalimumab, certolizumab pegol, methotrexate, an anti-α4-integrin antibody, natalizumab, vedolizumab, an anti-interleukin antibody, ustekinumab, an antibacterial antibiotic, ciprofloxacin, and metronidazole.

Emb. 22

Any one of the methods of embodiments 1-21, wherein the intervention is administration of a drug selected from the group consisting of: certolizumab pegol, methotrexate, and natalizumab.

Emb. 23

Any one of the methods of embodiments 1-22, wherein the intervention is placement of the subject on a low fat diet.

Emb. 24

A method of treating a patient suffering from or at risk of inflammatory bowel disease (IBD), said method comprising: performing the method of measuring HD5 in the patient according to embodiment 1; and; and performing an intervention on the patient to treat ulcerative colitis.

Emb. 25

The method of embodiment 24, comprising: comparing the expression of HD5 or the concentration of HD5 in the sample to a benchmark value that is typical of a subject not suffering from Crohn's disease; and diagnosing ulcerative colitis if the expression of HD5 or the concentration of HD5 in the sample does not significantly exceed the benchmark value.

Emb. 26

The method of any one of embodiments 24-25, wherein the expression of HD5 or the concentration of HD5 in the sample is below a benchmark value that is typical of a subject suffering from Crohn's disease.

Emb. 27

The method of any one of embodiments 24-25, wherein the expression or concentration of HD5 in the sample is measured to be significantly less than in a control sample from a subject suffering from Crohn's disease.

Emb. 28

The method of any one of embodiments 24-27, wherein the expression of HD5 is measured in the sample is no more than about $1/31$ of expression of HD5 measured in a control sample from a subject not suffering from Crohn's disease.

Emb. 29

The method of any one of embodiments 24-28, wherein the expression of HD5 is measured in the sample is no more than about $1/118$ of expression of HD5 measured in a control sample from a subject not suffering from Crohn's disease.

Emb. 30

The method of any one of embodiments 24-29, wherein the expression of HD5 is measured to be less than 106 HD5 mRNA transcripts per 10 ng RNA.

Emb. 31

The method of any one of embodiments 24-30, wherein the expression of HD5 is measured to be less than 107 HD5 mRNA transcripts per 10 ng RNA.

Emb. 32

The method of any one of embodiments 24-31, wherein the expression of HD5 is measured to be less than $1.9 \times 10^7$ HD5 mRNA transcripts per 10 ng RNA.

Emb. 33

The method of any one of embodiments 24-32, wherein the expression of HD5 is measured to be less than $6 \times 10^5$ HD5 mRNA transcripts per 10 ng RNA.

Emb. 34

The method of any one of embodiments 24-33, wherein the expression of HD5 is measured by qRT-PCR, wherein the method comprises measuring the expression of HD5 in a control sample from a subject suffering from Crohn's disease, and wherein the expression of HD5 mRNA in the sample is significantly less than the expression of HD5 in the control sample.

Emb. 35

The method of any one of embodiments 24-34, wherein the sample is intestinal tissue, and comprising measuring the concentration of HD5 by: immunostaining the sample with an anti-HD5 immunostaining agent; and measuring the percentage of cells in the sample that stain positive; wherein the percentage of cells in the sample that stain positive is less than 10%.

Emb. 36

The method of any one of embodiments 24-35, wherein the sample is intestinal tissue, and comprising measuring the concentration of HD5 by: immunostaining the sample with an anti-HD5 immunostaining agent; and measuring the percentage of cells in the sample that stain positive; wherein the percentage of cells in the sample that stain positive is less than 20%.

Emb. 37

The method of any one of embodiments 24-36, wherein the sample is intestinal tissue, and comprising measuring the concentration of HD5 by: immunostaining the sample with an anti-HD5 immunostaining agent; and measuring the percentage of cells in the sample that stain positive; wherein the percentage of cells in the sample that stain positive is less than about 30%.

Emb. 38

The method of any one of embodiments 24-37, wherein the intervention is not effective to treat Crohn's disease.

Emb. 39

The method of any one of embodiments 24-38, wherein the intervention is a surgery.

Emb. 40

The method of any one of embodiments 24-39, wherein the intervention is a surgery combined with the administration of a drug.

Emb. 41

The method of any one of embodiments 24-40, wherein the intervention is a surgery selected from the group consisting of: a proctocolectomy, and an ileal pouch anal anastomosis.

Emb. 42

The method of any one of embodiments 24-41, wherein the intervention is administration of a drug selected from the group consisting of: an iron supplement, an anti-inflammatory, a corticosteroid, a 5-aminosalicylate, an immunosuppressant, azathioprine, mercaptopurine, cyclosporine, an anti-TNF-alpha antibody, infliximab, adalimumab, golimumab, methotrexate, an anti-α4-integrin antibody, vedolizumab, an antibacterial antibiotic, ciprofloxacin, and metronidazole.

Emb. 43

The method of any one of embodiments 24-42, wherein the intervention is administration of a drug selected from the group consisting of: cyclosporine, and golimumab.

Emb. 44

The method of any one of embodiments 1-43, wherein the expression of HD5 is measured.

Emb. 45

The method of any one of embodiments 1-44, wherein the concentration of HD5 is measured.

Emb. 46

The method of any one of embodiments 1-45, wherein the sample is intestinal tissue.

Emb. 47

The method of any one of embodiments 1-46, wherein the sample is from the subject's large intestine.

Emb. 48

The method of any one of embodiments 1-47, wherein the sample is colonic tissue.

Emb. 49

The method of any one of embodiments 1-48, wherein the sample is ileal tissue.

Emb. 50

The method of any one of embodiments 1-49, wherein the expression of HD5 or the concentration of HD5 is measured in the sample ex vivo.

Emb. 51

The method of any one of embodiments 1-50, wherein HD5 expression is measured by a technique selected from the group consisting of: whole transcriptome analysis, whole-transcriptome microarray, Northern blot, DNA microarray, PCR, sequencing PCR, RT-PCR, quantitative PCR, restriction fragment length polymorphism, in situ hybridization assay, and a competitive-binding assay.

Emb. 52

The method of any one of embodiments 1-51, wherein HD5 concentration is measured by a technique selected from the group consisting of: Western blot, ELISA, two-dimensional gel electrophoresis, mass spectrometry, protein interaction profiling, a competitive binding assay, a non-competitive binding assay, a radioimmunoassay, an enzyme immunoassays, an enzyme linked immunosorbent assay (ELISA), a sandwich immunoassay, a precipitation reaction, a gel diffusion reaction, an immunodiffusion assay, an agglutination assay, a complement-fixation assay, an immunoradiometric assay, a fluorescent immunoassay, a protein A immunoassay, NMR analysis, and an immunoelectrophoresis assay.

Emb. 53

The method of any one of embodiments 1-52, wherein the patient is suffering from IBD.

Emb. 54

The method of any one of embodiments 1-53, wherein the patient displays a symptom selected from the group consisting of: severe diarrhea, abdominal pain, fatigue, and weight loss.

Emb. 55

The method of any one of embodiments 1-54, wherein the patient displays severe diarrhea, abdominal pain, fatigue, and weight loss.

Emb. 56

The method of any one of embodiments 1-55, wherein the expression of HD5 is measured.

Emb. 57

The method of any one of embodiments 1-56, wherein the concentration of HD5 is measured.

Emb. 58

The method of any one of embodiments 1-57, further comprising measuring at least one of the expression of MMP-7 and the concentration of MMP-7 in the sample.

Emb. 59

A method of measuring MMP-7 in a patient suffering from or at risk of inflammatory bowel disease (IBD), said method comprising:
obtaining a sample from the patient; and
measuring at least one of the expression of MMP-7 and the concentration of MMP-7 in the sample.

Emb. 60

A method of treating a patient suffering from or at risk of inflammatory bowel disease (IBD), said method comprising:
performing the method of measuring MMP-7 in the patient according to any one of embodiments 58-59; and
performing an intervention on the patient to treat Crohn's disease.

Emb. 61

The method of any one of embodiments 58-60, comprising: comparing the expression of MMP-7 or the concentration of MMP-7 in the sample to a benchmark value that is typical of a subject not suffering from ulcerative colitis; and diagnosing Crohn's disease if the expression of MMP-7 or the concentration of MMP-7 in the sample does not significantly exceed the benchmark value.

Emb. 62

The method of any one of embodiments 58-61, wherein the expression of MMP-7 or the concentration of MMP-7 in the sample is below a benchmark value that is typical of a subject suffering from ulcerative colitis.

Emb. 63

The method of any one of embodiments 58-61, wherein the expression of MMP-7 is measured to be significantly less in the sample than in a control sample from a subject suffering from ulcerative colitis.

Emb. 64

The method of any one of embodiments 58-63, wherein the expression of MMP-7 is measured in the sample to be at most about $1/10$ of the expression of MMP-7 measured in a control sample from a subject not suffering from ulcerative colitis.

Emb. 65

The method of any one of embodiments 58-64, wherein the expression of MMP-7 is measured by qRT-PCR, wherein the method comprises measuring the expression of MMP-7 in a control sample from a subject suffering from ulcerative colitis, and wherein the expression of MMP-7 in the sample is significantly less than the expression of MMP-7 in the control sample.

Emb. 66

The method of any one of embodiments 58-65, wherein the sample is intestinal tissue, and comprising measuring the concentration of MMP-7 by: immunostaining the sample with an antiMMP-7 immunostaining agent; and measuring the percentage of cells in the sample that stain positive.

Emb. 67

The method of any one of embodiments 58-66, wherein the intervention is not effective to treat ulcerative colitis.

Emb. 68

The method of any one of embodiments 58-67, wherein the intervention is a surgery.

Emb. 69

The method of any one of embodiments 58-68, wherein the intervention is a surgery selected from the group consisting of: ostomy, colostomy, ileostomy, bowel resection, colectomy, proctocolectomy, and strictureplasty.

Emb. 70

The method of any one of embodiments 58-69, wherein the intervention is administration of a drug.

Emb. 71

The method of any one of embodiments 58-70, wherein the intervention is administration of a drug, to the exclusion of a surgery.

Emb. 72

The method of any one of embodiments 58-71, wherein the intervention is administration of a drug selected from the group consisting of: a vitamin supplement, vitamin B12, vitamin D, a mineral supplement, calcium, an anti-inflammatory, a corticosteroid, a 5-aminosalicylate, an immunosuppressant, azathioprine, mercaptopurine, an anti-TNF-alpha antibody, infliximab, adalimumab, certolizumab pegol, methotrexate, an anti-α4-integrin antibody, natalizumab, vedolizumab, an anti-interleukin antibody, ustekinumab, an antibacterial antibiotic, ciprofloxacin, and metronidazole.

Emb. 73

The method of any one of embodiments 58-72, wherein the intervention is administration of a drug selected from the group consisting of: certolizumab pegol, methotrexate, and natalizumab.

Emb. 74

The method of any one of embodiments 58-73, wherein the intervention is placement of the subject on a low fat diet.

Emb. 75

A method of treating a patient suffering from or at risk of inflammatory bowel disease (IBD), said method comprising: performing the method of measuring MMP-7 in the patient according to embodiment 58; and performing an intervention on the patient to treat ulcerative colitis.

Emb. 76

The method of any one of embodiments 58, 59 and 75, comprising: comparing the expression of MMP-7 or the concentration of MMP-7 in the sample to a benchmark value that is typical of a subject not suffering from ulcerative colitis; and diagnosing ulcerative colitis if the expression of MMP-7 or the concentration of MMP-7 in the sample significantly exceeds the benchmark value.

Emb. 77

The method of any one of embodiments 58, 59 and 75-76, wherein the expression of MMP-7 or the concentration of MMP-7 in the sample is above a benchmark value that is typical of a subject not suffering from ulcerative colitis.

Emb. 78

The method of any one of embodiments 58, 59 and 75-76, wherein the expression or concentration of MMP-7 in the sample is measured to be significantly greater than in a control sample from a subject not suffering from ulcerative colitis.

Emb. 79

The method of any one of embodiments 58, 59 and 75-78, wherein the expression of MMP-7 measured in the sample is at least about 5 times the expression of MMP-7 measured in a control sample from a subject not suffering from ulcerative colitis.

Emb. 80

The method of any one of embodiments 58, 59 and 75-79, wherein the expression of MMP-7 measured in the sample is at least about 10 times the expression of MMP-7 measured in a control sample from a subject not suffering from ulcerative colitis.

Emb. 81

The method of any one of embodiments 58, 59 and 75-80, wherein the expression of MMP-7 is measured by qRT-PCR, wherein the method comprises measuring the expression of MMP-7 in a control sample from a subject not suffering from ulcerative colitis, and wherein the expression of MMP-7 in the sample is significantly greater than the expression of MMP-7 in the control sample.

Emb. 82

The method of any one of embodiments 58, 59 and 75-81, wherein the sample is intestinal tissue, and comprising measuring the concentration of MMP-7 by: immunostaining the sample with an anti MMP-7 immunostaining agent; and measuring the percentage of cells in the sample that stain positive.

Emb. 83

The method of any one of embodiments 58, 59 and 75-82, wherein the intervention is not effective to treat Crohn's disease.

Emb. 84

The method of any one of embodiments 58, 59 and 75-83, wherein the intervention is a surgery.

Emb. 85

The method of any one of embodiments 58, 59 and 75-84, wherein the intervention is a surgery combined with the administration of a drug.

Emb. 86

The method of any one of embodiments 58, 59 and 75-85, wherein the intervention is a surgery selected from the group consisting of: a proctocolectomy, and an ileal pouch anal anastomosis.

Emb. 87

The method of any one of embodiments 58, 59 and 75-86, wherein the intervention is administration of a drug selected from the group consisting of: an iron supplement, an anti-inflammatory, a corticosteroid, a 5-aminosalicylate, an immunosuppressant, azathioprine, mercaptopurine, cyclosporine, an anti-TNF-alpha antibody, infliximab, adalimumab, golimumab, methotrexate, an anti-α4-integrin antibody, vedolizumab, an antibacterial antibiotic, ciprofloxacin, and metronidazole.

Emb. 88

The method of any one of embodiments 58, 59 and 75-87, wherein the intervention is administration of a drug selected from the group consisting of: cyclosporine, and golimumab.

Emb. 89

The method of any one of embodiments 58-88, wherein the expression of MMP-7 or the concentration of MMP-7 is measured in the sample ex vivo.

Emb. 90

The method of any one of embodiments 58-89, wherein MMP-7 expression is measured by a technique selected from the group consisting of: whole transcriptome analysis, whole-transcriptome microarray, Northern blot, DNA microarray, PCR, sequencing PCR, RT-PCR, quantitative PCR, restriction fragment length polymorphism, in situ hybridization assay, and a competitive-binding assay.

Emb. 91

The method of any one of embodiments 58-90, wherein MMP-7 concentration is measured by a technique selected from the group consisting of: Western blot, ELISA, two-dimensional gel electrophoresis, mass spectrometry, protein interaction profiling, a competitive binding assay, a non-competitive binding assay, a radioimmunoassay, an enzyme immunoassays, an enzyme linked immunosorbent assay (ELISA), a sandwich immunoassay, a precipitation reaction, a gel diffusion reaction, an immunodiffusion assay, an agglutination assay, a complement-fixation assay, an immunoradiometric assay, a fluorescent immunoassay, a protein A immunoassay, NMR analysis, and an immunoelectrophoresis assay.

Emb. 92

The method of any one of embodiments 58-91, wherein the patient is suffering from IBD.

Emb. 93

The method of any one of embodiments 58-92, wherein the patient displays a symptom selected from the group consisting of: severe diarrhea, abdominal pain, fatigue, and weight loss.

Emb. 94

The method of any one of embodiments 58-93, wherein the patient displays severe diarrhea, abdominal pain, fatigue, and weight loss.

Emb. 95

The method of any one of embodiments 58-94, wherein the sample is intestinal tissue.

Emb. 96

The method of any one of embodiments 58-95, wherein the sample is from the subject's large intestine.

Emb. 97

The method of any one of embodiments 58-96, wherein the sample is colonic tissue.

Emb. 98

The method of any one of embodiments 58-97, wherein the sample is ileal tissue.

Emb. 99

A kit for measuring HD5 and MMP-7 in a sample, the kit comprising: a first assay for measuring at least one of the expression of human HD5 and the concentration of human HD5 in a sample; and a second assay for measuring at least one of the expression of human MMP-7 and the concentration of human MMP-7 in a sample.

Emb. 100

The kit of embodiment 99, wherein said kit is for the diagnosis of inflammatory bowel disease.

Emb. 101

The kit of any one of embodiments 99-100, wherein the first assay comprises an antibody that recognizes human HD5; and wherein the second assay comprises antibody that recognizes human MMP-7.

Emb. 102

The kit of any one of embodiments 99-101, wherein the first assay comprises an oligonucleotide probe that binds to human HD5 cDNA; and wherein the second assay comprises an oligonucleotide probe that binds to human MMP-7 cDNA.

Emb. 103

The kit of any one of embodiments 99-102, wherein the first assay comprises a pair of primers complementary to a region of human HD5 cDNA; and wherein the second assay comprises a pair of primers complementary to a region of human MMP-7 cDNA.

Emb. 104

The kit of any one of embodiments 99-103, wherein: the first assay comprises a means for detecting HD5 protein; and the second assay comprises a means for detecting MMP-7 protein.

Emb. 105

The kit of embodiment 104, wherein: the means for detecting the HD5 protein is a first probe comprising a first ligand group that specifically binds to HD5 protein; and the means for detecting MMP-7 protein is a second probe comprising a second ligand group that specifically binds to MMP-7 protein.

Emb. 106

The kit of embodiment 105, wherein the first ligand group is an immunoglobulin.

Emb. 107

The kit of any one of embodiments 105-106, wherein the second ligand group is an immunoglobulin.

Emb. 108

The kit of any one of embodiments 105-107, wherein the first probe and the second probe are immobilized to a surface.

Emb. 109

The kit of any one of embodiments 99-108, wherein: the assay for measuring the expression of HD5 detects a first target sequence of at least 15 bp that is present in a first cDNA or mRNA of HD5; and the assay for measuring the expression of MMP-7 detects a second target sequence of at least 15 bp that is present in a second cDNA or mRNA of MMP-7.

Emb. 110

The kit of embodiment 109, wherein: the assay for detecting the first target sequence comprises a first probe comprising a first polynucleotide of at least 15 bp that hybridizes under highly stringent conditions with the first target sequence of at least 15 bp that is present in the first cDNA or mRNA of HD5; and the assay for detecting the second target sequence comprises a second probe comprising a second polynucleotide of at least 15 bp that hybridizes under highly stringent conditions with the second target sequence of at least 15 bp that is present in the second cDNA or mRNA of MMP-7.

Emb. 111

The kit of any one of embodiments 109-110, comprising a container of a reverse transcriptase.

Emb. 112

The kit of any one of embodiments 102-111, wherein the first probe comprises a first reporter, and the second probe comprises a second reporter.

Emb. 113

The kit of embodiment 112, wherein the first reporter is selected from the group consisting of: a radionuclide, a stable isotope, a fluorophore, a chromophore, an enzyme, a magnetic particle, and a quantum dot; and the second reporter selected from the group consisting of: a radionuclide, a fluorophore, a chromophore, an enzyme, a magnetic particle, and a quantum dot.

Emb. 114

The kit of any one of embodiments 110-113, wherein the first polynucleotide is single stranded DNA; and wherein the second polynucleotide is single stranded DNA.

Emb. 115

The kit of any one of embodiments 102-114, wherein the first probe and the second probe are components of a DNA array.

Emb. 116

The kit of any one of embodiments 102-115, wherein the first probe and the second probe are components of a DNA microarray.

Emb. 117

The kit of any one of embodiments 110-116, wherein the first polynucleotide is at least 20 bp and the second polynucleotide is at least 20 bp.

Emb. 118

The kit of any one of embodiments 110-117, wherein the first polynucleotide is at least 25 bp and the second polynucleotide is at least 25 bp.

Emb. 119

A method of diagnosing and treating Crohn's disease in a subject suffering from inflammatory bowel disease, the method comprising:
obtaining a sample from the patient;
measuring at least one of the expression of HD5 and the concentration of HD5 in the sample;
comparing the expression of HD5 or the concentration of HD5 in the sample to a benchmark value that is typical of a subject not suffering from Crohn's disease;
diagnosing Crohn's disease if the expression of HD5 or the concentration of HD5 in the sample significantly exceeds the benchmark value; and
treating the subject for Crohn's disease by way of a non-surgical intervention.

Emb. 120

A method of diagnosing Crohn's disease in a subject suffering from inflammatory bowel disease, comprising: measuring the level of HD5 or HD5 expression in a sample from the subject, wherein the measuring is selected from the group consisting of: radioimmunoassays, reverse transcriptase PCR (RT-PCR) assays, immunohistochemistry assays, in situ hybridization assays, competitive-binding assays, Western Blot analyses, ELISA assays and proteomic approaches, cation-ion exchange, NMR analysis, genome-wide transcriptome analysis, mass spectrometry, and combinations thereof; and diagnosing the subject as suffering from Crohn's disease if the level of HD5 is indicative of a subject having Crohn's disease.

Emb. 121

The method of embodiment 120, wherein the subject is diagnosed as suffering from Crohn's disease if the level of HD5 or HD5 expression is from about $1.9 \times 10^7$ HD5 mRNA Transcript per 10 ng RNA to about $7 \times 10^7$ HD5 mRNA Transcript per 10 ng RNA.

Emb. 122

A method of diagnosing ulcerative colitis in a subject suffering from inflammatory bowel disease, comprising: measuring the level of HD5 or HD5 expression in a sample from the subject, wherein the measuring is selected from the group consisting of radioimmunoassays, reverse transcriptase PCR (RT-PCR) assays, immunohistochemistry assays, in situ hybridization assays, competitive-binding assays, Western Blot analyses, ELISA assays and proteomic approaches, cation-ion exchange, NMR analysis, genome-wide transcriptome analysis, mass spectrometry, and combinations thereof; and diagnosing the subject as suffering from ulcerative colitis if the level of HD5 or HD5 expression is indicative of a subject having ulcerative colitis.

Emb. 123

The method of embodiment 122, wherein the subject is diagnosed as suffering from ulcerative colitis if the level of HD5 or HD5 expression is from about $6 \times 10^5$ HD5 mRNA Transcript per 10 ng RNA to about $1.8 \times 10^7$ HD5 mRNA Transcript per 10 ng RNA.

Emb. 124

A method of treating inflammatory bowel disease in a subject, comprising: measuring the level of HD5 or HD5 expression present in a sample obtained from the subject, said measuring step wherein the measuring is selected from the group consisting of radioimmunoassays, reverse transcriptase PCR (RT-PCR) assays, immunohistochemistry assays, in situ hybridization assays, competitive-binding assays, Western Blot analyses, ELISA assays and proteomic approaches, cation-ion exchange, NMR analysis, genome-wide transcriptome analysis, mass spectrometry, and combinations thereof, whereby a level of HD5 or HD5 expression is obtained; and if the level of HD5 or HD5 expression is at a level indicative of a subject not having Crohn's disease, treating the inflammatory bowel disease in the subject with a suitable medical treatment for ulcerative colitis; if the level of HD5 or HD5 expression is at a level indicative of a subject having Crohn's disease, treating the inflammatory bowel disease in the subject with a suitable medical treatment for Crohn's disease.

Emb. 125

The method according to embodiment 122, wherein the suitable medical treatment for ulcerative colitis comprises performing ileal pouch anal anastomosis in the subject.

Emb. 126

The method according to embodiment 122, wherein the suitable medical treatment for Crohn's disease comprises the administration of one or more of 5aminosalicylate, a corticosteroid, and an immunosuppressant to the subject.

Emb. 127

The method according to embodiment 122, wherein the sample is collected from the large intestine, and the subject is human.

Emb. 128

An assay for detecting elevated levels of HD5, comprising an HD5 antibody capable of binding with HD5.

Emb. 129

The assay according to embodiment 128, wherein the assay is provided in a kit.

Emb. 130

The novel and non-obvious embodiments and features disclosed herein.

Emb. 131

A method of measuring a biomarker in a patient suffering from or at risk of inflammatory bowel disease (IBD), said method comprising: obtaining a sample from the patient; and measuring a level of the biomarker in the same, the level of the biomarker selected from the group consisting of: the expression of the biomarker, the activity of the biomarker, and the concentration of the biomarker; wherein said biomarker is selected from Table 1.

Emb. 132

A method of treating a patient suffering from or at risk of inflammatory bowel disease (IBD), said method comprising: performing the method of measuring the level of the biomarker in the patient according to embodiment 131; and performing an intervention on the patient to treat Crohn's disease.

Emb. 133

Any one of the methods of embodiments 131-132, comprising: comparing the level of the biomarker in the sample to a benchmark value that is typical of a subject not suffering from Crohn's disease; and diagnosing Crohn's disease if the expression of the biomarker in the sample significantly differs from the benchmark value.

CONCLUSIONS

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but as mentioned above, it is to be understood that the teachings of the present disclosure are capable of use in various other combinations, modifications and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77, or otherwise to provide organizational queues. These headings shall not limit or characterize the invention(s) set forth herein.

TABLE 1

| Gene Information | Gene Symbol | RefSeq | p-value (CC vs UC) | Fold Increase |
|---|---|---|---|---|
| NM_021010//DEFA5//defensin, alpha 5, Paneth cell-specific//8p23.1//1670 | DEFA5 | NM_021010 | 7.23E−05 | 31.0374 |
| NM_002909//REG1A//regenerating islet-derived 1 alpha//2p12//5967///ENS | REG1A | NM_002909 | 0.00321456 | 21.9439 |
| NM_138938//REG3A//regenerating islet-derived 3 alpha//2p12//5068///NM_ | REG3A | NM 138938 | 0.000310891 | 17.3268 |
| NM_001926//DEFA6//defensin, alpha 6, Paneth cell-specific//8p23.1//1671 | DEFA6 | NM_001926 | 0.0024893 | 16.139 |
| NM_058186//FAM3B//family with sequence similarity 3, member B//21q22.3// | FAM3B | NM_058186 | 0.00116588 | 14.6887 |
| NM_006507//REG1B//regenerating islet-derived 1 beta//2p12//5968///ENST | REG1B | NM_006507 | 0.0120953 | 13.9675 |
| NM_001074//UGT2B7//UDP glucuronosyltransferase 2 family, polypeptide B7//4 | UGT2B7 | NM_001074 | 0.0154146 | 9.92532 |
| NM_001285//CLCA1//chloride channel accessory 1//1p22.3//1179///ENST000 | CLCA1 | NM_001285 | 0.00297816 | 9.07579 |
| NM_003122//SPINK1//serine peptidase inhibitor, Kazal type 1//5q32//6690 | SPINK1 | NM_003122 | 0.007176 | 7.60063 |
| NM_001076//UGT2B15//UDP glucuronosyltransferase 2 family, polypeptide B15// | UGT2B15 | NM_001076 | 0.0169187 | 7.12294 |
| NM_001076//UGT2B15//UDP glucuronosyltransferase 2 family, polypeptide B15// | UGT2B15 | NM_001076 | 0.0169187 | 7.12294 |
| NM_000343//SLC5A1//solute carrier family 5 (sodium/glucose cotransporter), m | SLC5A1 | NM_000343 | 0.00447091 | 7.0494 |
| NM_000134//FABP2//fatty acid binding protein 2, intestinal//4q28-q31//21 | FABP2 | NM_000134 | 0.0300574 | 6.63756 |
| NM_000035//ALDOB//aldolase B, fructose-bisphosphate//9q21.3-q22.2//229/ | ALDOB | NM_000035 | 0.0444145 | 6.30502 |
| NM_002770//PRSS2//protease, serine, 2 (trypsin 2)//7q34//5645///ENST00 | PRSS2 | NM_002770 | 0.0052665 | 6.27999 |
| NM_005379//MYO1A//myosin IA//12q13-q14//4640///ENST00000300119//MYO1 | MYO1A | NM_005379 | 0.00588172 | 5.72861 |
| NM_007329//DMBT1//deleted in malignant brain tumors 1//10q26.13//1755// | DMBT1 | NM_007329 | 0.0365636 | 5.56609 |
| NM_031457//MS4A8B//membrane-spanning 4-domains, subfamily A, member 8B//11 | MS4A8B | NM_031457 | 0.00577952 | 5.34254 |
| NM_001041//SI//sucrase-isomaltase (alpha-glucosidase)//3q25.2-q26.2//647 | SI | NM_001041 | 0.0417578 | 5.23854 |
| NM_000482//APOA4//apolipoprotein A-IV//11q23//337///ENST00000357780// | APOA4 | NM_000482 | 0.0468523 | 5.15957 |
| NM_006418//OLFM4//olfactomedin 4//13q14.3//10562///ENST00000219022// | OLFM4 | NM_006418 | 0.038931 | 5.05883 |
| NM_000482//APOA4//apolipoprotein A-IV//11q23//337 ///ENST00000357780 // | APOA4 | NM_000482 | 0.0472178 | 4.92519 |
| NM_004133//HNF4G//hepatocyte nuclear factor 4, gamma//8q21.11//3174/// | HNF4G | NM_004133 | 0.0113549 | 4.8964 |
| NM_017675//CDHR2//cadherin-related family member 2//5q35.2//54825///NM_ | CDHR2 | NM_017675 | 0.00253568 | 4.82206 |
| NM_005588//MEP1A//meprin A, alpha (PABA peptide hydrolase)//6p12-p11//42 | MEP1A | NM_005588 | 0.0198087 | 4.78504 |
| NM_002354//EPCAM//epithelial cell adhesion molecule//2p21//4072///ENST | EPCAM | NM_002354 | 0.0242383 | 4.77321 |
| NM_001172312//PLS1//plastin 1//3q23//5357////NM_001145319//PLS1//pl | PLS1 | NM_001172312 | 0.0155248 | 4.73894 |
| NM_002354//EPCAM//epithelial cell adhesion molecule//2p21//4072///ENST | EPCAM | NM_002354 | 0.0297878 | 4.72533 |
| NM_001150//ANPEP//alanyl (membrane) aminopeptidase//15q25-q26//290//E | ANPEP | NM_001150 | 0.0203087 | 4.58929 |
| NM_001077//UGT2B17//UDP glucuronosyltransferase 2 family, polypeptide B17// | UGT2B17 | NM_001077 | 0.0267812 | 4.51157 |
| NM_002591//PCK1//phosphoenolpyruvate carboxykinase 1 (soluble)//20q13.31/ | PCK1 | NM_002591 | 0.0333639 | 4.50793 |

TABLE 1-continued

| Gene Information | Gene Symbol | RefSeq | p-value (CC vs UC) | Fold Increase |
|---|---|---|---|---|
| NM_021804//ACE2//angiotensin I converting enzyme (peptidyl-dipeptidase A) 2 | ACE2 | NM_021804 | 0.0271919 | 4.49025 |
| NM_024308//DHRS11//dehydrogenase/reductase (SDR family) member 11//17q12/ | DHRS11 | NM_024308 | 0.0176773 | 4.41914 |
| NM_019010//KRT20//keratin 20//17q21.2//54474///ENST00000167588//KRT2 | KRT20 | NM_019010 | 0.026162 | 4.35459 |
| ENST00000319509//MUC3A//mucin 3A, cell surface associated//7q22//4584// | MUC3A | ENST00000319509 | 0.00353785 | 4.28484 |
| NM_000379//XDH//xanthine dehydrogenase//2p23.1//7498///ENST00000379416 | XDH | NM_000379 | 0.00289109 | 4.17476 |
| NM_007127//VIL1//villin 1//2q35//7429///ENST00000248444//VIL1//vil | VIL1 | NM_007127 | 0.00825691 | 4.16925 |
| NM_025130//HKDC1//hexokinase domain containing 1//10q22.1//80201///ENS | HKDC1 | NM_025130 | 0.00344261 | 4.13874 |
| NR_029578//MIR192//microRNA 192//11q13.1//406967 | MIR192 | NR_029578 | 0.00199884 | 4.12467 |
| NM_004063//CDH17//cadherin 17, LI cadherin (liver-intestine)//8q22.1//10 | CDH17 | NM_004063 | 0.0331015 | 4.12001 |
| NM_024922//CES3//carboxylesterase 3//16q22.1//23491///NM_001185177// | CES3 | NM_024922 | 0.0022354 | 4.11886 |
| NM_033049//MUC13//mucin 13, cell surface associated//3q21.2//56667///E | MUC13 | NM_033049 | 0.0271079 | 4.11287 |
| NM_000888//ITGB6//integrin, beta 6//2q24.2//3694///ENST00000283249// | ITGB6 | NM_000888 | 0.000602949 | 4.09738 |
| NM_004963//GUCY2C//guanylate cyclase 2C (heat stable enterotoxin receptor)/ | GUCY2C | NM_004963 | 0.00645462 | 4.0793 |
| NM_004293//GDA//guanine deaminase//9q21.13//9615///ENST00000358399// | GDA | NM_004293 | 0.0208862 | 4.0739 |
| NM_001307//CLDN7//claudin 7//17p13//1366//NM_001185022//CLDN7//cl | CLDN7 | NM_001307 | 0.0213404 | 4.06183 |
| NR_033807//CYP3A5//cytochrome P450, family 3, subfamily A, polypeptide 5// | CYP3A5 | NR_033807 | 0.0046334 | 4.04376 |
| NM_021924//CDHR5//cadherin-related family member 5//11p15.5//53841///N | CDHR5 | NM_021924 | 0.00480695 | 3.97925 |
| NM_001010922//BCL2L15//BCL2-like 15//1p13.2//440603///ENST00000393316 | BCL2L15 | NM_001010922 | 0.027053 | 3.96946 |
| NM_020770//CGN//cingulin//1q21//57530///ENST00000271636//CGN//cing | CGN | NM_020770 | 0.00129584 | 3.94184 |
| NM_032787//GPR128//G protein-coupled receptor 128//3q12.2//84873///ENS | GPR128 | NM_032787 | 0.00779494 | 3.93937 |
| NM_138933//A1CF//APOBEC1 complementation factor//10q11.23//29974 | CF | NM_138933 | 0.00976589 | 3.79699 |
| NM_152311//CLRN3//clarin 3//10q26.2//119467///ENST00000368671//CLRN3 | CLRN3 | NM_152311 | 0.0132404 | 3.74982 |
| NM_007072//HHLA2//HERV-H LTR-associating 2//3q13.13//11148///ENST00000 | HHLA2 | NM_007072 | 0.0139075 | 3.74668 |
| NM_003399//XPNPEP2//X-prolyl aminopeptidase (aminopeptidase P) 2, membrane-b | XPNPEP2 | NM_003399 | 0.0359348 | 3.73179 |
| NM_021258//IL22RA1//interleukin 22 receptor, alpha 1//1p36.11//58985/// | IL22RA1 | NM_021258 | 0.00520995 | 3.72759 |
| NM_000149//FUT3//fucosyltransferase 3 (galactoside 3(4)-L-fucosyltransferase | FUT3 | NM_000149 | 0.0106419 | 3.70158 |
| NM_002644//PIGR//polymeric immunoglobulin receptor//1q31-q41//5284///E | PIGR | NM_002644 | 0.0363588 | 3.68869 |
| NM_001136503//C19orf77//chromosome 19 open reading frame 77//19p13.3//28 | C19orf77 | NM_001136503 | 0.0114867 | 3.6586 |
| NR_024626//C17orf73//chromosome 17 open reading frame 73//17q21.33//5501 | C17orf73 | NR_024626 | 0.00240775 | 3.64138 |
| NM_020973//GBA3//glucosidase, beta, acid 3 (cytosolic)//4p15.2//57733// | GBA3 | NM_020973 | 0.0362758 | 3.63402 |
| NM_023944//CYP4F12//cytochrome P450, family 4, subfamily F, polypeptide 12/ | CYP4F12 | NM_023944 | 0.00468827 | 3.62246 |
| NM_024320//PRR15L//proline rich 15-like//17q21.32//79170///ENST0000030 | PRR15L | NM_024320 | 0.0331566 | 3.60367 |
| NM_005495//SLC17A4//solute carrier family 17 (sodium phosphate), member 4// | SLC17A4 | NM_005495 | 0.0299201 | 3.59753 |
| NM_001135099//TMPRSS2//transmembrane protease, serine 2//21q22.3//7113/ | TMPRSS2 | NM_001135099 | 0.0351257 | 3.57585 |
| NM_001193434//C10orf81//chromosome 10 open reading frame 81//10q25.3//79 | C10orf81 | NM_001193434 | 0.00228381 | 3.5687 |
| NM_001935//DPP4//dipeptidyl-peptidase 4//2q24.3//1803///ENST0000036053 | DPP4 | NM_001935 | 0.0302652 | 3.49144 |

TABLE 1-continued

| Gene Information | Gene Symbol | RefSeq | p-value (CC vs UC) | Fold Increase |
|---|---|---|---|---|
| NM_001644//APOBEC1//apolipoprotein B mRNA editing enzyme, catalytic polypept | APOBEC1 | NM_001644 | 0.0138008 | 3.48792 |
| NM_004360//CDH1//cadherin 1, type 1, E-cadherin (epithelial)//16q22.1//9 | CDH1 | NM_004360 | 0.010781 | 3.48059 |
| NM_024921//POF1B//premature ovarian failure, 1B//Xq21.2//79983////ENSTO | POF1B | NM_024921 | 0.0313161 | 3.44457 |
| NM_002416//CXCL9//chemokine (C—X—C motif) ligand 9//4q21//4283////ENSTO | CXCL9 | NM_002416 | 0.00248734 | 3.44146 |
| NM_014479//ADAMDEC1//ADAM-like, decysin 1//8p21.2//27299///NM_00114527 | ADAMDEC1 | NM_014479 | 0.00203661 | 3.42469 |
| NM_001112706//SCIN//scinderin//7p21.3//85477///NM_033128//SCIN//sc | SCIN | NM_001112706 | 0.00493508 | 3.3952 |
| NR_024345//NCRNA00262//non-protein coding RNA 262//12q24.31//283460 | NCRNA00262 | NR_024345 | 0.037473 | 3.39502 |
| NM_002273//KRT8//keratin 8//12q13//3856///ENST00000293308//KRT8//k | KRT8 | NM_002273 | 0.0146545 | 3.39222 |
| NM_001038603//MARVELD2//MARVEL domain containing 2//5q13.2//153562///E | MARVELD2 | NM_001038603 | 0.0179974 | 3.37682 |
| NM_001038603//MARVELD2//MARVEL domain containing 2//5q13.2//153562///E | MARVELD2 | NM_001038603 | 0.0179974 | 3.37682 |
| NM_144575//CAPN13//calpain 13//2p22-p21//92291////ENST00000295055//CA | CAPN13 | NM_144575 | 0.013239 | 3.36885 |
| NM_022129//PBLD//phenazine biosynthesis-like protein domain containing//10 | PBLD | NM_022129 | 0.00497915 | 3.3666 |
| NM_000775//CYP2J2//cytochrome P450, family 2, subfamily J, polypeptide 2// | CYP2J2 | NM_000775 | 0.0196093 | 3.36302 |
| NM_001135195//SLC39A5//solute carrier family 39 (metal ion transporter), mem | SLC39A5 | NM_001135195 | 0.00623473 | 3.34227 |
| NM_138788//TMEM45B//transmembrane protein 45B//11q24.3//120224///ENST0 | TMEM45B | NM_138788 | 0.0306305 | 3.33725 |
| NM_176813//AGR3//anterior gradient homolog 3 (Xenopus laevis)//7p21.1//1 | AGR3 | NM_176813 | 0.0400823 | 3.32266 |
| NM_022901//LRRC19//leucine rich repeat containing 19//9p21.2//64922/// | LRRC19 | NM_022901 | 0.0294679 | 3.31296 |
| NM_139053//EPS8L3//EPS8-like 3//1p13.3//79574 ///NM_133181//EPS8L3// | EPS8L3 | NM_139053 | 0.00371579 | 3.29224 |
| NM_017697//ESRP1//epithelial splicing regulatory protein 1//8q22.1//5484 | ESRP1 | NM_017697 | 0.0234665 | 3.27492 |
| NM_002457//MUC2//mucin 2, oligomeric mucus/gel-forming//11p15.5//4583// | MUC2 | NM_002457 | 0.0182535 | 3.26416 |
| NR_001296//TRY6//trypsinogen C//7q34//154754///NM_002770//PRSS2//p | TRY6 | NR_001296 | 0.0203767 | 3.24356 |
| NM_002773//PRSS8//protease, serine, 8//16p11.2 //5652///ENST00000317508 | PRSS8 | NM_002773 | 0.0131026 | 3.2405 |
| NM_025214//CCDC68//coiled-coil domain containing 68//18q21//80323 ///NM_ | CCDC68 | NM_025214 | 0.00627753 | 3.2264 |
| NM_001943//DSG2//desmoglein 2//18q12.1//1829////ENST00000261590//DSG2 | DSG2 | NM_001943 | 0.0357587 | 3.22627 |
| NM_000772//CYP2C18//cytochrome P450, family 2, subfamily C, polypeptide 18/ | CYP2C18 | NM_000772 | 0.0100284 | 3.20876 |
| NM_000767//CYP2B6//cytochrome P450, family 2, subfamily B, polypeptide 6// | CYP2B6 | NM_000767 | 0.00589423 | 3.19484 |
| NM_016234//ACSL5//acyl-CoAsynthetase long-chain family member 5//10q25.1- | ACSL5 | NM_016234 | 0.00353915 | 3.19242 |
| NM_145865//ANKS4B//ankyrin repeat and sterile alpha motif domain containing | ANKS4B | NM_145865 | 0.027168 | 3.16823 |
| NM_032579//RETNLB//resistin like beta//3q13.1//84666///ENST00000295755 | RETNLB | NM_032579 | 0.0226491 | 3.14305 |
| NM_021978//ST14//suppression of tumorigenicity 14 (colon carcinoma)//11q24 | ST14 | NM_021978 | 0.0143682 | 3.14171 |
| NM_000492//CFTR//cystic fibrosis transmembrane conductance regulator (ATP-bi | CFTR | NM_000492 | 0.0330127 | 3.13524 |
| NM_018842//BAIAP2L1//BAI 1-associated protein 2-like 1//7q22.1//55971/// | BAIAP2L1 | NM_018842 | 0.00626097 | 3.13099 |
| NM_001165958//GSDMB//gasdermin B//17q12//55876///NM_001042471//GSDMB | GSDMB | NM_001165958 | 0.0013942 | 3.1309 |
| NM_024422//DSC2//desmocollin 2//18q12.1//1824//NM_004949//DSC2 lid | DSC2 | NM_024422 | 0.0115939 | 3.11862 |
| NM_006017//PROM1//prominin 1//4p15.32//8842//NM_001145847//PROM1// | PROM1 | NM_006017 | 0.0116042 | 3.10273 |
| NM_017878//HRASLS2//HRAS-like suppressor 2//11q12.3//54979//ENST00000 | HRASLS2 | NM_017878 | 0.0267887 | 3.09847 |
| NM_002203//ITGA2//integrin, alpha 2 (CD49B, alpha 2 subunit of VLA-2 recepto | ITGA2 | NM_002203 | 0.00793505 | 3.07141 |
| NM_005123//NR1H4//nuclear receptor subfamily 1, group H, member 4//12q23.1 | NR1H4 | NM_005123 | 0.0456782 | 3.06865 |

TABLE 1-continued

| Gene Information | Gene Symbol | RefSeq | p-value (CC vs UC) | Fold Increase |
|---|---|---|---|---|
| NM_001145862//MTMR11//myotubularin related protein 11//1q12-q21//10903/ | MTMR11 | NM_001145862 | 0.00116554 | 3.03455 |
| NM_018414//ST6GALNAC1//ST6 (alpha-N-acetyl-neuraminyl-2,3-beta-galactosyl-1, | ST6GALNAC1 | NM_018414 | 0.0240185 | 3.0202 |
| NM_001080527//MYO7B//myosin VIIB// 2q21.1 11 4648///ENST00000428314//MY | MYO7B | NM_001080527 | 0.00130692 | 2.99927 |
| NM_002153//HSD17B2//hydroxysteroid (17-beta) dehydrogenase 2//16q24.1-q24. | HSD17B2 | NM_002153 | 0.0213389 | 2.99803 |
| AK095678//LOC151009//hypothetical LOC151009//2q13///151009///AK056084/ | LOC151009 | AK095678 | 0.000466288 | 2.99502 |
| NM_000769//CYP2C19//cytochrome P450, family 2, subfamily C, polypeptide 19/ | CYP2C19 | NM_000769 | 0.0193957 | 2.99186 |
| NM_000790//DDC//dopa decarboxylase (aromatic L-amino acid decarboxylase)/ | DDC | NM_000790 | 0.0257511 | 2.98778 |
| NM_001143948//C6orf105//chromosome 6 open reading frame 105//6p24.1//848 | C6orf105 | NM_001143948 | 0.0220945 | 2.95786 |
| NM_001015001//CKMT1A//creatine kinase, mitochondrial 1A//15q15//548596/ | CKMT1A | NM_001015001 | 0.042629 | 2.95709 |
| NM_001015001//CKMT1A//creatine kinase, mitochondrial 1A//15q15//548596/ | CKMT1A | NM_001015001 | 0.042629 | 2.95709 |
| NM_019893//ASAH2//N-acylsphingosine amidohydrolase (non-lysosomal ceramidase | ASAH2 | NM_019893 | 0.0167497 | 2.95643 |
| NM_001002236//SERPINA1//serpin peptidase inhibitor, clade A (alpha-1 antipro | SERPINA1 | NM_001002236 | 0.0170929 | 2.94245 |
| NM_002031//FRK//fyn-related kinase// 6q21-q22.3//2444///ENST00000368626 | FRK | NM_002031 | 0.0177896 | 2.93608 |
| NM_001190482//PCSK5//proprotein convertase subtilisin/kexin type 5//9q21.3 | PCSK5 | NM_001190482 | 0.00160967 | 2.92603 |
| NM_004415//DSP//desmoplakin//6p24// 1832//NM_001008844//DSP//desmo | DSP | NM_004415 | 0.0116502 | 2.91732 |
| NM_004591//CCL20//chemokine (C—C motif) ligand 20//2q33-q37//6364///NM | CCL20 | NM_004591 | 0.0229351 | 2.91511 |
| NM_000561//GSTM1//glutathione S-transferase mu 1//p13.3//2944///NM_14 | GSTM1 | NM_000561 | 0.032505 | 2.91233 |
| NM_000927//ABCB1//ATP-binding cassette, sub-family B (MDRfTAP), member 1// | ABCB1 | NM_000927 | 0.03279 | 2.89709 |
| NM_000187//HGD//homogentisate 1,2-dioxygenase//3q13.33//3081///ENST000 | HGD | NM_000187 | 0.0180393 | 2.8961 |
| NM_000187//HGD//homogentisate 1,2-dioxygenase//3q13.33//3081///ENST000 | HGD | NM_000187 | 0.0180393 | 2.8961 |
| NM_153676//USH1C//Usher syndrome 1C (autosomal recessive, severe)//11p14.3 | USH1C | NM_153676 | 0.00547469 | 2.88241 |
| NM_005624//CCL25//chemokine (C—C motif) ligand 25//19p13.2//6370///ENS | CCL25 | NM 005624 | 0.0492359 | 2.86049 |
| NM_004174//SLC9A3//solute carrier family 9 (sodium/hydrogen exchanger), memb | SLC9A3 | NM 004174 | 0.0173616 | 2.8567 |
| NM_001306//CLDN3//claudin 3//7q11.23// 1365///ENST00000395145//CLDN3 | CLDN3 | NM_001306 | 0.0490185 | 2.84657 |
| NM_001114309//ELF3//E74-like factor 3 (ets domain transcription factor, epit | ELF3 | NM_001114309 | 0.00265363 | 2.84098 |
| NM_000507//FBP1//fructose-1,6-bisphosphatase1//9q22.3//2203///NM_0011 | FBP1 | NM_000507 | 0.022351 | 2.83767 |
| NM_025257//SLC44A4//solute carrier family 44, member 4//6p21.3//80736// | SLC44A4 | NM_025257 | 0.0415598 | 2.83697 |
| NM_025257//SLC44A4//solute carrier family 44, member 4//6p21.3//80736// | SLC44A4 | NM_025257 | 0.0415598 | 2.83697 |
| NM_025257//SLC44A4//solute carrier family 44, member 4//6p21.3//80736// | SLC44A4 | NM_025257 | 0.0415598 | 2.83697 |
| NM_001017970//TMEM30B// transmembraneprotein 30B//14q23.1// 161291///EN | TMEM30B | NM_001017970 | 0.00717685 | 2.83259 |
| NM_003963//TM4SF5//transmembrane 4 L six family member 5//17p13.3//9032 | TM4SF5 | NM_003963 | 0.0295851 | 2.82875 |
| NM_002242//KCNJ13//potassium inwardly-rectifying channel, subfamily J, membe | KCNJ13 | NM_002242 | 0.0400838 | 2.82471 |
| NM_017655//GIPC2//GIPC PDZ domain containing family, member 2//1p31.1//5 | GIPC2 | NM_017655 | 0.0155498 | 2.81938 |
| NM_001127605//LIPA//lipase A, lysosomal acid, cholesterol esterase//10q23. | LIPA | NM_001127605 | 0.000449938 | 2.81611 |
| NM_001249//ENTPD5//ectonucleoside triphosphate diphosphohydrolase 5//14q24 | ENTPD5 | NM_001249 | 0.0118697 | 2.81265 |
| NM_005358//LMO7//LIM domain 7// 13q22.2//4008//NM_015842//LMO7//LI | LMO7 | NM_005358 | 0.00460576 | 2.80795 |
| NM_018667//SMPD3//sphingomyelin phosphodiesterase 3, neutral membrane (neutr | SMPD3 | NM_018667 | 0.00228114 | 2.80665 |

TABLE 1-continued

| Gene Information | Gene Symbol | RefSeq | p-value (CC vs UC) | Fold Increase |
|---|---|---|---|---|
| NM_004563//PCK2//phosphoenolpyruvate carboxykinase 2 (mitochondrial)//14q1 | PCK2 | NM_004563 | 0.00983672 | 2.79262 |
| NM_003657//BCAS1//breast carcinoma amplified sequence 1//20q13.2//8537/ | BCAS1 | NM_003657 | 0.0213345 | 2.78368 |
| NM_024850//BTNL8//butyrophilin-like 8// 5q35.3//79908///NM_001040462// | BTNL8 | NM_024850 | 0.0446038 | 2.7769 |
| NM_020672//S100A14//S100 calcium binding protein A14//1q21.3//57402/// | S100A14 | NM_020672 | 0.0202797 | 2.77156 |
| NM_033229//TRIM15//tripartite motif-containing 15//6p21.3//89870///ENS | TRIM15 | NM_033229 | 0.0097609 | 2.77095 |
| NM_033229//TRIM15//tripartite motif-containing 15//6p21.3//89870///ENS | TRIM15 | NM_033229 | 0.0097609 | 2.77095 |
| NM_033229//TRIM15//tripartite motif-containing 15//6p21.3//89870///ENS | TRIM15 | NM_033229 | 0.0097609 | 2.77095 |
| NM_001144060//NHSL1//NHS-like 1// 6q23.3//57224//NM_020464//NHSL1// | NHSL1 | NM_001144060 | 0.0124428 | 2.7705 |
| NM_003869//CES2//carboxylesterase 2// 16q22.1//8824//NR_036684//CES2 | CES2 | NM_003869 | 0.0197746 | 2.76326 |
| NM_199187//KRT18//keratin 18//12q13// 3875///NM_000224//KRT18//kera | KRT18 | NM_199187 | 0.0272938 | 2.7567 |
| NM_002842//PTPRH//protein tyrosine phosphatase, receptor type, H//19q13.4 | PTPRH | NM_002842 | 0.00126103 | 2.75623 |
| NM_001105248//TMC5//transmembrane channel-like 5//16p12.3//79838///NM_ | TMC5 | NM_001105248 | 0.015439 | 2.74553 |
| NM_001145809//MYH14//myosin, heavy chain 14, non-muscle//19q13.33//79784 | MYH14 | NM_001145809 | 0.00203315 | 2.74198 |
| NM_001054//SULT1A2//sulfotransferase family, cytosolic, 1A, phenol-preferrin | SULT1A2 | NM_001054 | 0.0273843 | 2.73 |
| NM_024850//BTNL8//butyrophilin-like 8// 5q35.3//79908///NM_001159708// | BTNL8 | NM_024850 | 0.0433332 | 2.7165 |
| NM_006147//IRF6//interferon regulatory factor 6//1q32.3-q41//3664///EN | IRF6 | NM_006147 | 0.00663477 | 2.71435 |
| NM_000457//HNF4A//hepatocyte nuclear factor 4, alpha//20q13.12//3172/// | HNF4A | NM_000457 | 0.00414138 | 2.70616 |
| NM_138809//CMBL// carboxymethylenebutenolidase homolog (Pseudomonas)//5p15. | CMBL | NM_138809 | 0.0336993 | 2.69623 |
| NM_001080467//MYO5B//myosin VB// 18q21//4645//ENST00000285039//MYO5B | MYO5B | NM_001080467 | 0.00639465 | 2.69568 |
| NM_153274//BEST4//bestrophin 4// 1p33-p32.3//266675///ENST00000372207/ | BEST4 | NM_153274 | 0.0313639 | 2.68747 |
| NM_020775//KIAA1324//KIAA1324// 1p13.3//57535///ENST00000234923//KIAA | KIAA1324 | NM_020775 | 0.0214297 | 2.68133 |
| NM_001004320//TMEM195//transmembrane protein 195//7p21.2//392636///ENS | TMEM195 | NM_001004320 | 0.0149666 | 2.67293 |
| NM_001091//ABP1//amiloride binding protein 1 (amine oxidase (copper-containi | ABP1 | NM_001091 | 0.0487109 | 2.66772 |
| NM_016245//HSD17B11//hydroxysteroid (17-beta) dehydrogenase 11// 4q22.1// | HSD17B11 | NM_016245 | 0.0216559 | 2.66473 |
| NM_006144//GZMA//granzyme A (granzyme 1, cytotoxic T-lymphocyte-associated s | GZMA | NM_006144 | 0.00618242 | 2.66284 |
| NM_001039372//HEPACAM2//HEPACAM family member 2//7q21.3//253012///NM_1 | HEPACAM2 | NM_001039372 | 0.0201907 | 2.6524 |
| NM_001197097//PRSS3//protease, serine, 3//9p11.2//5646//NM_007343// | PRSS3 | NM_001197097 | 0.0173103 | 2.63924 |
| NM_012214//MGAT4A//mannosyl (alpha-1,3-)-glycoprotein beta-1,4-N-acetylgluco | MGAT4A | NM_012214 | 0.00113208 | 2.62742 |
| NM_019894//TMPRSS4//transmembrane protease, serine 4//11q23.3//56649/// | TMPRSS4 | NM_019894 | 0.0362683 | 2.60764 |
| NM_003810//TNFSF10//tumor necrosis factor (ligand) superfamily, member 10// | TNFSF10 | NM_003810 | 0.0129809 | 2.60509 |
| NM_022842//CDCP1//CUB domain containing protein 1//3p21.31//64866//NM | CDCP1 | NM_022842 | 0.0167874 | 2.60268 |
| NM_001136493//MFSD2A//major facilitator superfamily domain containing 2A// | MFSD2A | NM_001136493 | 0.00343618 | 2.59815 |
| NM_018265//C1orf106//chromosome 1 open reading frame 106//1q32.1//55765 | C1orf106 | NM_018265 | 0.00613223 | 2.59677 |
| NM_000063//C2//complement component 2//6p21.3//717///NM_001145903//C | C2 | NM_000063 | 0.0117239 | 2.59406 |
| NM_000063//C2//complement component 2//6p21.3//717 ///NM_001145903//C | C2 | NM_000063 | 0.0117239 | 2.59406 |
| NM_000625//NOS2//nitric oxide synthase 2, inducible//17q11.2-q12//4843/ | NOS2 | NM_000625 | 0.0089305 | 2.59304 |
| NM_001677//ATP1B1//ATPase, Na+/K+ transporting, beta 1 polypeptide//1q24/ | ATP1B1 | NM_001677 | 0.0131783 | 2.58871 |

TABLE 1-continued

| Gene Information | Gene Symbol | RefSeq | p-value (CC vs UC) | Fold Increase |
|---|---|---|---|---|
| NM_004751//GCNT3//glucosaminyl (N-acetyl) transferase 3, mucin type//15q21 | GCNT3 | NM_004751 | 0.0432197 | 2.58761 |
| NM_002021//FMO1//flavin containing monooxygenase 1//1q24.3//2326///ENS | FMO1 | NM_002021 | 0.0408097 | 2.57646 |
| NM_033292//CASP1//caspase 1, apoptosis-related cysteine peptidase (interleuk | CASP1 | NM_033292 | 0.00634065 | 2.57013 |
| NM_147161//ACOT11//acyl-CoA thioesterase 11//1p32.3//26027/// ENST00000 | ACOT11 | NM_147161 | 0.0462671 | 2.53682 |
| NM_001039112//FER1L6//fer-1-like 6 (C. elegans)//8q24.1//654463///ENST | FER1L6 | NM_001039112 | 0.0413201 | 2.53444 |
| NM_212543//B4GALT4//UDP-Gal:betaGlcNAc beta 1,4-galactosyltransferase, poly | B4GALT4 | NM_212543 | 0.00083206 | 2.53146 |
| NM_182762//MACC1//metastasis associated in colon cancer 1//7p21.1//34638 | MACC1 | NM_182762 | 0.0113734 | 2.52994 |
| NM_001461//FMO5//flavin containing monooxygenase 5//1q21.1//2330 ///NM_ | FMO5 | NM_001461 | 0.0227505 | 2.52925 |
| NM_031219//HDHD3//haloacid dehalogenase-like hydrolase domain containing 3/ | HDHD3 | NM_031219 | 0.00048055 | 2.52696 |
| NM_001010872//FAM83B//family with sequence similarity 83, member B//6p12.1 | FAM83B | NM_001010872 | 0.00806204 | 2.52496 |
| NM_024533//CHST5//carbohydrate (N-acetylglucosamine 6-O) sulfotransferase 5 | CHST5 | NM_024533 | 0.026327 | 2.51739 |
| NM_000063//C2//complement component 2//6p21.3/1717///NM_001145903//C | C2 | NM_000063 | 0.0114041 | 2.51419 |
| NM_004624//VIPR1//vasoactive intestinal peptide receptor 1//3p22//7433/ | VIPR1 | NM_004624 | 0.00331244 | 2.50863 |
| NM_004572//PKP2//plakophilin 2//12p11// 5318///NM_001005242//PKP2// | PKP2 | NM_004572 | 0.042448 | 2.49612 |
| NM_032521//PARD6B//par-6 partitioning defective 6 homolog beta (C. elegans) | PARD6B | NM_032521 | 0.00395798 | 2.49598 |
| NM_024915//GRHL2//grainyhead-like 2 (Drosophila)//8q22.3//79977///ENST | GRHL2 | NM_024915 | 0.00624177 | 2.49455 |
| NM_003982//SLC7A7//solute carrier family 7 (cationic amino acid transporter, | SLC7A7 | NM_003982 | 0.00813405 | 2.49274 |
| NM_198584//CA13//carbonic anhydrase XIII//8q21.2//377677///ENST0000032 | CA13 | NM 198584 | 0.00510852 | 2.48988 |
| ENST00000319509//MUC3A//mucin 3A, cell surface associated//7q22//4584// | MUC3A | ENST00000319509 | 0.0135883 | 2.4817 |
| NM_021102//SPINT2//serine peptidase inhibitor, Kunitz type, 2//19q13.1// | SPINT2 | NM_021102 | 0.0219176 | 2.48131 |
| NM_080489//SDCBP2//syndecan binding protein (syntenin) 2//20p13//27111/ | SDCBP2 | NM_080489 | 0.000789754 | 2.47862 |
| NM_001144967//NEDD4L//neural precursor cell expressed, developmentally down- | NEDD4L | NM_001144967 | 0.0227827 | 2.47791 |
| NM_001982//ERBB3//v-erb-b2 erythroblastic leukemia viral oncogene homolog 3 | ERBB3 | NM_001982 | 0.0175723 | 2.47531 |
| NM_000240//MAOA//monoamine oxidase A//Xp11.3//4128///ENST00000338702/ | MAOA | NM_000240 | 0.0446884 | 2.47082 |
| NM_182960//PRELID2//PRELI domain containing 2//5q32//153768///NM_13849 | PRELID2 | NM_182960 | 0.00837834 | 2.47032 |
| NM_017720//STAP2//signal transducing adaptor family member 2//19p13.3//5 | STAP2 | NM_017720 | 0.016285 | 2.46781 |
| NM_138700//TRIM40//tripartite motif-containing 40//6p22.1//135644///EN | TRIM40 | NM_138700 | 0.0336507 | 2.45989 |
| NM_000050//ASS1//argininosuccinate synthase 1//9q34.1//445///NM_054012 | ASS1 | NM_000050 | 0.0132614 | 2.43678 |
| NM_005021//ENPP3//ectonucleotide pyrophosphatase/phosphodiesterase3//6q22 | ENPP3 | NM_005021 | 0.0149678 | 2.43651 |
| NM_001130080//IFI27//interferon, alpha-inducible protein 27//14q32//3429 | IFI27 | NM_001130080 | 0.0140236 | 2.43613 |
| NM_001979//EPHX2//epoxide hydrolase 2, cytoplasmic//8p21//2053//BC011 | EPHX2 | NM_001979 | 0.00690804 | 2.43531 |
| NM_017700//ARHGEF38//Rho guanine nucleotide exchange factor (GEF) 38//4q24 | ARHGEF38 | NM_017700 | 0.00476968 | 2.42966 |
| NM_019080//NDFIP2//Nedd4 family interacting protein 2//13q31.1//54602// | NDFIP2 | NM_019080 | 0.00576011 | 2.42832 |
| NM_001135181//SLC5A9//solute carrier family 5 (sodium/glucose cotransporter) | SLC5A9 | NM_001135181 | 0.0296431 | 2.42215 |
| NM_032717//AGPAT9//1-acylglycerol-3-phosphate O-acyltransferase 9//4q21.23 | AGPAT9 | NM_032717 | 0.0147877 | 2.41843 |

TABLE 1-continued

| Gene Information | Gene Symbol | RefSeq | p-value (CC vs UC) | Fold Increase |
|---|---|---|---|---|
| NM_001145303//TMC4//transmembrane channel-like 4//19q13.42//147798///N | TMC4 | NM_001145303 | 0.00110774 | 2.41442 |
| NM_138700//TRIM40//tripartite motif-containing 40//6p22.1//135644///EN | TRIM40 | NM_138700 | 0.0250665 | 2.41358 |
| NM_138700//TRIM40//tripartite motif-containing 40//6p22.1//135644///EN | TRIM40 | NM_138700 | 0.0250665 | 2.41358 |
| NM_203463//LASS6//LAG1 homolog, ceramide synthase 6//2q24.3//253782/// | LASS6 | NM_203463 | 0.00156196 | 2.41203 |
| NM_001730//KLF5//Kruppel-like factor 5 (intestinal)//13q22.1//688///EN | KLF5 | NM_001730 | 0.0129015 | 2.40278 |
| NM_001265//CDX2//caudal type homeobox 2//13q12.3//1045/// ENST000003810 | CDX2 | NM_001265 | 0.0471437 | 2.402 |
| NM_000239//LYZ//lysozyme//12q15// 4069///ENST00000261267//LYZ//lyso | LYZ | NM_000239 | 0.0118582 | 2.39899 |
| NM_022772//EPS8L2//EPS8-like 2// 11p15.5//64787///ENST00000318562//EP | EPS8L2 | NM_022772 | 0.00191717 | 2.39231 |
| NM_025153//ATP10B//ATPase, class V, type 10B//5q34//23120//ENST000003 | ATP10B | NM_025153 | 0.0273664 | 2.38677 |
| NM_178445//CCRL1//chemokine (C—C motif) receptor-like 1//3q22//51554/// | CCRL1 | NM_178445 | 0.0328488 | 2.38032 |
| NM_001031803//LLGL2//lethal giant larvae homolog 2 (Drosophila)//17q25.1/ | LLGL2 | NM_001031803 | 0.00351395 | 2.36948 |
| NM_175058//PLEKHA7//pleckstrin homology domain containing, family A member 7 | PLEKHA7 | NM_175058 | 0.00170237 | 2.36502 |
| NM_006714//SMPDL3A//sphingomyelin phosphodiesterase, acid-like 3A//6q22.31 | SMPDL3A | NM_006714 | 0.0236138 | 2.36218 |
| NR_024158//LOC25845//hypothetical LOC25845//5p15.33//25845///ENST00000 | LOC25845 | NR_024158 | 0.0297858 | 2.35341 |
| NM_016339//RAPGEFL1//Rap guanine nucleotide exchange factor (GEF)-like 1// | RAPGEFL1 | NM_016339 | 0.026897 | 2.3526 |
| NM_015888//HOOK1//hook homolog 1 (Drosophila)//1p32.1//51361///ENST000 | HOOK1 | NM_015888 | 0.0336071 | 2.34842 |
| NM_138737//HEPH//hephaestin//Xq11-q12//9843///NM_001130860//HEPH// | HEPH | NM_138737 | 0.0118198 | 2.34595 |
| NM_012079//DGAT1//diacylglycerol O-acyltransferase 1//8q24.3//8694///E | DGAT1 | NM_012079 | 0.023252 | 2.34522 |
| NM_012079//DGAT1//diacylglycerol O-acyltransferase 1//8q24.3//8694///E | DGAT1 | NM_012079 | 0.023252 | 2.34522 |
| NM_001017535//VDR//vitamin D (1,25-dihydroxyvitamin D3) receptor//12q13.1 | VDR | NM_001017535 | 0.0115491 | 2.34153 |
| NM_001029874//REP15//RAB15 effector protein//12p11.22//387849///ENST00 | REP15 | NM_001029874 | 0.0477963 | 2.33656 |
| NM_198495//CTAGE4//CTAGE family, member4//7q35//100128553/// NM_001145 | CTAGE4 | NM_198495 | 0.00065154 | 2.33596 |
| NM_006548//IGF2BP2//insulin-like growth factor 2 mRNA binding protein 2//3 | IGF2BP2 | NM_006548 | 8.80E-05 | 2.33476 |
| NM_002985//CCL5//chemokine (C—C motif) ligand 5//17q11.2-q12//6352///E | CCL5 | NM_002985 | 0.0247261 | 2.33002 |
| NM_001005328//OR2A7//olfactory receptor, family 2, subfamily A, member 7// | OR2A7 | NM_001005328 | 0.00337105 | 2.32021 |
| NM_018284//GBP3//guanylate binding protein 3//1p22.2//2635///ENST00000 | GBP3 | NM_018284 | 0.013933 | 2.31798 |
| NM_002829//PTPN3//protein tyrosine phosphatase, non-receptor type 3//9q31 | PTPN3 | NM_002829 | 0.0212048 | 2.31511 |
| NM_021073//BMP5//bone morphogenetic protein 5//6p12.1//653///ENST00000 | BMP5 | NM_021073 | 0.0201876 | 2.31001 |
| NM_178176//MOGAT3//monoacylglycerol O-acyltransferase 3//7q22.1//346606 | MOGAT3 | NM_178176 | 0.00641018 | 2.30988 |
| NM_000666//ACY1//aminoacylase 1// 3p21.1//95///L07548//ACY1//aminoa | ACY1 | NM_000666 | 0.0261486 | 2.30581 |
| NM_001098634//RBM47//RNA binding motif protein 47//4p14//54502//NM_01 | RBM47 | NM_001098634 | 0.00857247 | 2.30203 |
| NM_080658//ACY3//aspartoacylase (aminocyclase) 3//11q13.2//91703///ENS | ACY3 | NM_080658 | 0.0498753 | 2.301 |
| NR_003587//MYO15B//myosin XNB pseudogene//17q25.1//80022//BC027875// | MYO15B | NR_003587 | 0.00759021 | 2.29754 |
| NM_005435//ARHGEF5//Rho guanine nucleotide exchange factor (GEF) 5//7q33-q | ARHGEF5 | NM_005435 | 0.00766916 | 2.29684 |
| NM_005435//ARHGEF5//Rho guanine nucleotide exchange factor (GEF) 5//7q33-q | ARHGEF5 | NM_005435 | 0.00846455 | 2.29311 |
| NM_001017967//MARVELD3//MARVEL domain containing 3//16q22.2//91862///N | MARVELD3 | NM_001017967 | 0.0124186 | 2.2921 |
| NM_003389//CORO2A//coronin, actin binding protein, 2A//9q22.3//7464/// | CORO2A | NM_003389 | 0.0203606 | 2.28709 |

TABLE 1-continued

| Gene Information | Gene Symbol | RefSeq | p-value (CC vs UC) | Fold Increase |
|---|---|---|---|---|
| NM_031469//SH3BGRL2//SH3 domain binding glutamic acid-rich protein like 2// | SH3BGRL2 | NM_031469 | 0.0214373 | 2.27245 |
| NM_030766//BCL2L14//BCL2-like 14 (apoptosis facilitator)//12p13-p12//793 | BCL2L14 | NM_030766 | 0.0037691 | 2.26634 |
| NR_002713//NPY6R//neuropeptide Y receptor Y6 (pseudogene)//5q31//4888// | NPY6R | NR_002713 | 0.0429642 | 2.26407 |
| NM_001114086//CLIC5//chloride intracellular channel 5//6p12.3//53405/// | CLIC5 | NM_001114086 | 0.0269601 | 2.25433 |
| NM_003645//SLC27A2//solute carrier family 27 (fatty acid transporter), membe | SLC27A2 | NM_003645 | 0.040906 | 2.2539 |
| NM_001136050//DHRS1// dehydrogenase/reductase (SDR family) member 1//14q12 | DHRS1 | NM_001136050 | 0.000608529 | 2.23931 |
| NM_002164//IDO1//indoleamine 2,3-dioxygenase 1//8p12-p11//3620///ENSTO | IDO1 | NM_002164 | 0.00532092 | 2.2314 |
| NM_001171192//GDPD2//glycerophosphodiester phosphodiesterase domain containi | GDPD2 | NM_001171192 | 0.0455387 | 2.23073 |
| NM_016445//PLEK2//pleckstrin 2// 14q23.3//26499///ENST00000216446//PL | PLEK2 | NM_016445 | 0.0184048 | 2.22972 |
| NR_033122//PDZD3//PDZ domain containing 3//11q23.3//79849///NM_0011684 | PDZD3 | NR_033122 | 0.0104609 | 2.2269 |
| NM_000932//PLCB3//phospholipase C, beta 3 (phosphatidylinositol-specific)// | PLCB3 | NM_000932 | 0.01393 | 2.22018 |
| NM_018235//CNDP2//CNDP dipeptidase 2 (metallopeptidase M20 family)//18q22. | CNDP2 | NM_018235 | 0.000958173 | 2.20566 |
| NM_032562//PLA2G12B//phospholipase A2, group XIIB//10q22.1//84647//EN | PLA2G12B | NM_032562 | 0.0420214 | 2.20423 |
| NM_021080//DAB1//disabled homolog 1 (Drosophila)//1p32-p31//1600///ENS | DAB1 | NM_021080 | 0.04076 | 2.20106 |
| NM_001710//CFB//complement factor B// 6p21.3//629///ENST00000425368// | CFB | NM_001710 | 0.00181667 | 2.19954 |
| NM_183240//TMEM37//transmembrane protein 37//2q14.2//140738///ENST0000 | TMEM37 | NM_183240 | 0.0487149 | 2.19842 |
| AK127847//FLJ45950//FLJ45950 protein// 11q24.3//399975 | FLJ45950 | AK127847 | 0.00195329 | 2.198 |
| NM_001710//CFB//complement factor B// 6p21.3//629///ENST00000417261// | CFB | NM_001710 | 0.00220919 | 2.19758 |
| NM_144590//ANKRD22//ankyrin repeat domain 22//10q23.31//118932///ENSTO | ANKRD22 | NM_144590 | 0.0445105 | 2.19752 |
| NM_002067//GNA11//guanine nucleotide binding protein (G protein), alpha 11 ( | GNA11 | NM_002067 | 0.014093 | 2.19185 |
| NM_006579//EBF//emopamil binding protein (sterol isomerase)//Xp11.23-p11.2 | EBF | NM_006579 | 0.0115147 | 2.18786 |
| NM_014873//LPGAT1// lysophosphatidylglycerol acyltransferase 1// 1q32//992 | LPGAT1 | NM_014873 | 0.000550666 | 2.18469 |
| NM_030943//AMN//amnionless homolog (mouse)//14q32.3//81693///ENST00000 | AMN | NM_030943 | 0.00168811 | 2.18289 |
| NM_016548//GOLM1//golgi membrane protein 1//9q21.33//51280///NM_177937 | GOLM1 | NM_016548 | 0.0424472 | 2.18243 |
| NM_032148//SLC41A2//solute carrier family 41, member 2//12q23.3//84102/ | SLC41A2 | NM_032148 | 0.0301277 | 2.17752 |
| NM_000949//PRLR//prolactin receptor// 5p13.2//5618///ENST00000382002// | PRLR | NM_000949 | 0.0313649 | 2.17608 |
| NM_181642//SPINT1//serine peptidase inhibitor, Kunitz type 1//15q15.1//6 | SPINT1 | NM_181642 | 0.0361797 | 2.17498 |
| NM_001113567//C17orf76//chromosome 17 open reading frame 76//17p11.2//38 | C17orf76 | NM_001113567 | 0.0248369 | 2.17219 |
| NM_000355//TCN2//transcobalamin//// 22q12.2//6948///NM_001184726//TC | TCN2 | NM_000355 | 0.0233279 | 2.17134 |
| NM_015198//COBL//cordon-bleu homolog (mouse)//7p12.1//23242//ENST0000 | COBL | NM_015198 | 0.0208672 | 2.1656 |
| NM_024616//C3orf52//chromosome 3 open reading frame 52//3q13.2//79669// | C3orf52 | NM_024616 | 0.00881101 | 2.16302 |
| NM_020469//ABO//ABO blood group (transferase A, alpha 1-3-N-acetylgalactosam | ABO | NM_020469 | 0.00222828 | 2.16292 |
| NM_030908//OR2A4//olfactory receptor, family 2, subfamily A, member 4//6q2 | OR2A4 | NM_030908 | 0.00568966 | 2.15894 |
| NM_003980//MAP7//microtubule-associated protein 7//6q23.3//9053///NM_0 | MAP7 | NM_003980 | 0.0037529 | 2.15742 |
| NM_017417//GALNT8//UDP-N-acetyl-alpha-D-galactosamine:polypeptide N-acetylga | GALNT8 | NM_017417 | 0.013696 | 2.15417 |
| NM_005410//SEPP1//selenoprotein P, plasma, 1//5q31//6414///NM_00108548 | SEPP1 | NM_005410 | 0.0133071 | 2.15347 |
| NM_152573//RASEF//RAS and EF-hand domain containing//9q21.32//158158/// | RASEF | NM_152573 | 0.0366785 | 2.15133 |

TABLE 1-continued

| Gene Information | Gene Symbol | RefSeq | p-value (CC vs UC) | Fold Increase |
|---|---|---|---|---|
| NM_006633//IQGAP2//IQ motif containing GTPase activating protein 2//5q13.3 | IQGAP2 | NM 006633 | 0.00969849 | 2.1509 |
| NM_152550//SH3RF2//SH3 domain containing ring finger 2//5q32//153769/// | SH3RF2 | NM_152550 | 0.00614396 | 2.15072 |
| NM_018686//CMAS//cytidine monophosphate N-acetylneuraminic acid synthetase/ | CMAS | NM_018686 | 0.0124234 | 2.14998 |
| NM_025045//BAIAP2L2//BAI 1-associated protein 2-like 2//22q13.1//80115// | BAIAP2L2 | NM_025045 | 0.0129162 | 2.14195 |
| NM_001859//SLC31A1//solute carrier family 31 (copper transporters), member 1 | SLC31A1 | NM_001859 | 0.00838827 | 2.13821 |
| NM_016614//TDP2//tyrosyl-DNA phosphodiesterase 2//6p22.3-p22.1//51567// | TDP2 | NM_016614 | 0.0246156 | 2.13573 |
| NM_003848//SUCLG2//succinate-CoA ligase, GDP-forming, beta subunit//3p14.1 | SUCLG2 | NM_003848 | 0.00569037 | 2.13077 |
| NM_017904//TTC22//tetratricopeptide repeat domain 22//1p32.3//55001/// | TTC22 | NM_017904 | 0.0153126 | 2.12827 |
| NM_003060//SLC22A5//solute carrier family 22 (organic cation/carnitine trans | SLC22A5 | NM_003060 | 0.02024 | 2.12394 |
| NM_002662//PLD1//phospholipase D1, phosphatidylcholine-specific//3q26//5 | PLD1 | NM_002662 | 0.0135876 | 2.12113 |
| NM_018964//SLC37A1//solute carrier family 37 (glycerol-3-phosphate transport | SLC37A1 | NM_018964 | 0.0229039 | 2.12062 |
| NM_001251//CD68//CD68 molecule// 17p13//968///NM_001040059//CD68//C | CD68 | NM_001251 | 0.00105743 | 2.11575 |
| NM_174941//CD163L1//CD163 molecule-like 1//12p13.3//283316///ENST00000 | CD163L1 | NM_174941 | 0.00407203 | 2.11396 |
| NM_016029//DHRS7// dehydrogenase/reductase (SDR family) member 7//14q23.1/ | DHRS7 | NM_016029 | 0.0124063 | 2.11159 |
| NM_024101//MLPH//melanophilin// 2q37.3//79083////NM_001042467//MLPH// | MLPH | NM_024101 | 0.00197625 | 2.10533 |
| NM_004670//PAPSS2//3'-phosphoadenosine 5'-phosphosulfate synthase 2//10q24 | PAPSS2 | NM_004670 | 0.0403309 | 2.10272 |
| AK172782//GPAM//glycerol-3-phosphate acyltransferase, mitochondrial//10q25 | GPAM | AK172782 | 0.0314353 | 2.09633 |
| NM_001142685//ARHGAP32//Rho GTPase activating protein 32//11q24.3//9743 | ARHGAP32 | NM_001142685 | 0.00415504 | 2.09203 |
| NM_198495//CTAGE4//CTAGE family, member 4//7q35//100128553/// NM_001145 | CTAGE4 | NM_198495 | 0.00141321 | 2.0906 |
| ENST00000439698//P4HA2//prolyl 4-hydroxylase, alpha polypeptide////5q31/ | P4HA2 | ENST00000439698 | 0.0142839 | 2.08741 |
| NM_015020//PHLPP2//PH domain and leucine rich repeat protein phosphatase 2/ | PHLPP2 | NM_015020 | 0.013905 | 2.08634 |
| NM_004252//SLC9A3R1//solute carrier family 9 (sodium/hydrogen exchanger), me | SLC9A3R1 | NM_004252 | 0.00776993 | 2.0857 |
| NM_012243//SLC35A3//solute carrier family 35 (UDP-N-acetylglucosamine (UDP-G | SLC35A3 | NM_012243 | 0.0307101 | 2.07986 |
| NM_020184//CNNM4//cyclin M4//2q11// 26504///ENST00000377075//CNNM4// | CNNM4 | NM_020184 | 0.02685 | 2.07897 |
| NM_001490//GCNT1//glucosaminyl (N-acetyl) transferase 1, core 2//9q13//2 | GCNT1 | NM_001490 | 0.00172819 | 2.07671 |
| NM_003667//LGR5//leucine-rich repeat-containing G protein-coupled receptor 5 | LGR5 | NM_003667 | 0.0237574 | 2.07254 |
| NM_001966//EHHADH//enoyl-CoA, hydratase/3-hydroxyacyl CoA dehydrogenase//3 | EHHADH | NM_001966 | 0.0130422 | 2.07114 |
| NM_017726//PPP1R14D//protein phosphatase 1, regulatory (inhibitor) subunit 1 | PPP1R14D | NM_017726 | 0.0497008 | 2.07017 |
| NM_006994//BTN3A3//butyrophilin, subfamily 3, member A3//6p21.3//10384/ | BTN3A3 | NM_006994 | 0.00121808 | 2.06925 |
| NM_001039724//NOSTRIN//nitric oxide synthase trafficker//2q31.1//115677 | NOSTRIN | NM_001039724 | 0.00986343 | 2.06731 |
| NR_026912//ABHD11//abhydrolase domain containing 11//7q11.23//83451/// | ABHD11 | NR_026912 | 0.000593971 | 2.05896 |
| NM_001145206//KIAA1671//KIAA1671// 22q11.23//85379///ENST00000358431// | KIAA1671 | NM_001145206 | 0.00446756 | 2.05612 |
| NM_153345//TMEM139//transmembrane protein 139//7q34//135932//ENST0000 | TMEM139 | NM_153345 | 0.00505302 | 2.05293 |
| NM_001164694//IYD//iodotyrosine deiodinase//6q25.1//389434///NM_203395 | IYD | NM_001164694 | 0.022189 | 2.05208 |
| NM_016472//C14orf129//chromosome 14 open reading frame 129//14q32.2//515 | C14orf129 | NM_016472 | 0.048055 | 2.04519 |
| NM_001017402//LAMB3//laminin, beta 3// 1q32//3914////NM_001127641//LAM | LAMB3 | NM_001017402 | 0.0267716 | 2.04174 |

TABLE 1-continued

| Gene Information | Gene Symbol | RefSeq | p-value (CC vs UC) | Fold Increase |
|---|---|---|---|---|
| NM_004999//MYO6//myosin VI//6q13// 4646///ENST00000369977//MYO6//my | MYO6 | NM_004999 | 0.00369349 | 2.04095 |
| NR_027244//LOC151009//hypothetical LOC151009//2q13//151009//NR_027244 | LOC151009 | NR_027244 | 0.0115721 | 2.04078 |
| AB065085//TOM1L1//target of myb1 (chicken)-like 1//17q23.2//10040 | TOM1L1 | AB065085 | 0.04656 | 2.03713 |
| NM_017750//RETSAT//retinol saturase (all-trans-retinol 13,14-reductase)//2 | RETSAT | NM_017750 | 0.0184264 | 2.03345 |
| NM_004721//MAP3K13//mitogen-activated protein kinase kinase kinase 13//3q2 | MAP3K13 | NM_004721 | 0.00937615 | 2.03148 |
| NM_018677//ACSS2//acyl-CoA synthetase short-chain family member 2//20q11.2 | ACSS2 | NM_018677 | 0.0306269 | 2.02661 |
| NM_014317//PDSS1//prenyl (decaprenyl) diphosphate synthase, subunit 1//10p | PDSS1 | NM_014317 | 0.0365076 | 2.02171 |
| NM_014498//GOLIM4//golgi integral membrane protein 4//3q26.2//27333/// | GOLIM4 | NM_014498 | 0.00240934 | 2.02056 |
| NM_033429//CALML4//calmodulin-like 4 //15q23 /191860///NM_001031733 /C | CALML4 | NM_033429 | 0.0419784 | 2.01981 |
| NR_036751//HSP90AA6P//heat shock protein 90 kDa alpha (cytosolic), class A me | HSP90AA6P | NR_036751 | 0.0220954 | 2.01604 |
| NM_012120//CD2AP//CD2-associated protein//6p12//23607///ENST0000035931 | CD2AP | NM_012120 | 0.00502091 | 2.0122 |
| NM_005536//IMPA1//inositol(myo)-1(or 4)-monophosphatase 1//8q21.13-q21.3/ | IMPA1 | NM_005536 | 0.0194688 | 2.01203 |
| NM_001153//ANXA4//annexin A4//2p13// 307///ENST00000394295//ANXA4/ | ANXA4 | NM_001153 | 0.0255723 | 2.01151 |
| NM_000147//FUCA1//fucosidase, alpha-L- 1, tissue//1p34//2517///ENST000 | FUCA1 | NM_000147 | 0.00469253 | 2.0105 |
| NM_003774//GALNT4//UDP-N-acetyl-alpha-D-galactosamine:polypeptide N-acetylga | GALNT4 | NM_003774 | 0.00622316 | 2.00871 |
| NM_001122890//GGT6//gamma-glutamyltransferase 6//17p13.2//124975///NM_ | GGT6 | NM_001122890 | 0.0328357 | 2.00627 |
| NM_001164277//SLC37A4//solute carrier family 37 (glucose-6-phosphate transpo | SLC37A4 | NM_001164277 | 0.0068184 | 2.00477 |
| NM_001565//CXCL10//chemokine (C—X—C motif) ligand 10//4q21//3627///ENS | CXCL10 | NM_001565 | 0.0468134 | 2.00368 |
| NM_005030//PLK1//polo-like kinase 1// 16p12.2//5347///ENST00000300093/ | PLK1 | NM_005030 | 0.0109795 | 2.00251 |
| NM_001012631//IL32//interleukin 32// 16p13.3//9235//NM_004221//IL32 | IL32 | NM_001012631 | 0.0214868 | 2.00238 |
| NM_005309//GPT//glutamic-pyruvate transaminase (alanine aminotransferase)// | GPT | NM_005309 | 0.0098254 | 2.00201 |
| NM_005159//ACTC1//actin, alpha, cardiac muscle 1//15q11-q14//70//ENST | ACTC1 | NM_005159 | 0.00451989 | −2.00712 |
| NM_130385//MRVI1//murine retrovirus integration site 1 homolog//11p15//1 | MRVI1 | NM_130385 | 0.0186352 | −2.00908 |
| NR_003329//SNORD116-14//small nucleolar RNA, C/D box 116-14//15q11.2//10 | SNORD116-14 | NR_003329 | 0.00710694 | −2.01066 |
| NM_030751//ZEB1//zinc finger E-box binding homeobox 1//10p11.2//6935/// | ZEB1 | NM_030751 | 0.0190641 | −2.01665 |
| NM_001321//CSRP2//cysteine and glycine-rich protein 2/I 12q21.1//1466/// | CSRP2 | NM_001321 | 0.0130189 | −2.01975 |
| NM_199460//CACNA1C//calcium channel, voltage-dependent, L type, alpha 1C sub | CACNA1C | NM_199460 | 0.0164629 | −2.03364 |
| NM_007078//LDB3//LIM domain binding 3// 10q22.3-q23.2//11155//NM_00117 | LDB3 | NM_007078 | 0.013344 | −2.03636 |
| ENST00000436525//C15of151//dynamin 1 pseudogene//15q26.3//196968 | C15orf51 | ENST00000436525 | 0.0479813 | −2.04311 |
| ENST00000436525//C15or151//dynamin 1 pseudogene//15q26.3//196968 | C15orf51 | ENST00000436525 | 0.0479813 | −2.04311 |
| NM_001042454//TGFB1I1//transforming growth factor beta 1 induced transcript | TGFB1I1 | NM_001042454 | 0.0141045 | −2.0503 |
| NM_201266//NRP2//neuropilin 2//2q33.3// 8828///NM_003872//NRP2//neu | NRP2 | NM_201266 | 0.0231808 | −2.05329 |
| NM_014286//NCS1//neuronal calcium sensor 1//9q34//23413//NM_001128826 | NCS1 | NM_014286 | 0.0400809 | −2.05571 |
| NR_002960//SNORA20//small nucleolar RNA, H/ACA box 20//6q25.3//677806 | SNORA20 | NR_002960 | 0.0102255 | −2.05618 |
| NR_023343//RNU4ATAC//RNA, U4atac small nuclear (U12-dependent splicing)//2 | RNU4ATAC | NR_023343 | 0.0114016 | −2.05953 |
| NM_003829//MPDZ//multiple PDZ domain protein//9p23//8777////ENST0000038 | MPDZ | NM_003829 | 0.0230169 | −2.06542 |
| NM_182734//PLCB1//phospholipase C, beta 1 (phosphoinositide-specific)//20p | PLCB1 | NM_182734 | 0.0285626 | −2.0675 |
| NM_212482//FN1//fibronectin 1//2q34// 2335///NM_002026//FN1//fibron | FN1 | NM_212482 | 0.0289963 | −2.06817 |

TABLE 1-continued

| Gene Information | Gene Symbol | RefSeq | p-value (CC vs UC) | Fold Increase |
|---|---|---|---|---|
| NM_001166292//PTCH2//patched 2// 1p34.1//8643///ENST00000438067//PTCH | PTCH2 | NM_001166292 | 0.0155977 | −2.06949 |
| NM_001128310//SPARCL1//SPARC-like 1 (hevin)//4q22.1//8404///NM_004684 | SPARCL1 | NM_001128310 | 0.0275433 | −2.0695 |
| NR_003332//SNORD116-17//small nucleolar RNA, C/D box 116-17//15q11.2//10 | SNORD116-17 | NR_003332 | 0.00123218 | −2.07085 |
| NR_003332//SNORD116-17//small nucleolar RNA, C/D box 116-17//15q11.2//10 | SNORD116-17 | NR_003332 | 0.00123218 | −2.07085 |
| NM_001390//DTNA//dystrobrevin, alpha// 18q12//1837///NM_032975//DTNA | DTNA | NM_001390 | 0.0140008 | −2.07227 |
| NM_172316//MEIS2//Meis homeobox 2// 15q14//4212///NM_170677//MEIS2// | MEIS2 | NM_172316 | 0.012629 | −2.07482 |
| NM_032801//JAM3//junctional adhesion molecule 3//11q25//83700///ENST00 | JAM3 | NM_032801 | 0.00375191 | −2.08055 |
| NM_001496//GFRA3//GDNF family receptor alpha 3//5q31.1-q31.3//2676///E | GFRA3 | NM_001496 | 0.0143176 | −2.08436 |
| NM_003116//SPAG4//sperm associated antigen 4//20q11.21//6676///ENST000 | SPAG4 | NM_003116 | 0.0370178 | −2.09743 |
| NR_002754//RNU5E//RNA, U5E small nuclear//1p36.22//26829///M77839//R | RNU5E | NR_002754 | 0.0153145 | −2.10499 |
| NM_000109//DMD//dystrophin//Xp21.2// 1756///NM_004010//DMD//dystrop | DMD | NM_000109 | 0.0305823 | −2.10535 |
| NM_005725//TSPAN2//tetraspanin 2// 1p13.2//10100///ENST00000369516//T | TSPAN2 | NM_005725 | 0.00484522 | −2.10726 |
| ENST00000436525//C15orf51//dynamin 1 pseudogene//15q26.3//196968 | C15orf51 | ENST00000436525 | 0.0401346 | −2.11861 |
| NM_001190839//MGP//matrix Gla protein// 12p12.3//4256///NM_000900//MG | MGP | NM_001190839 | 0.0229696 | −2.13146 |
| NM_031442//TMEM47//transmembrane protein 47//Xp11.4//83604///ENST00000 | TMEM47 | NM_031442 | 0.0162367 | −2.16059 |
| NM_002776//KLK10//kallikrein-related peptidase 10//19q13//5655///NM_14 | KLK10 | NM_002776 | 0.0131782 | −2.16442 |
| NM_134269//SMTN//smoothelin// 22q12.2//6525///NM_134270//SMTN//smoo | SMTN | NM_134269 | 0.0278447 | −2.16615 |
| NM_002742//PRKD1//protein kinase D1// 14q11//5587///ENST00000331968// | PRKD1 | NM_002742 | 0.0208525 | −2.17797 |
| NM_001001396//ATP2B4//ATPase, Ca++ transporting, plasma membrane 4//1q32.1 | ATP2B4 | NM_001001396 | 0.0372252 | −2.18014 |
| NM_005451//PDLIM7//PDZ and LIM domain 7 (enigma)//5q35.3//9260///NM_20 | PDLIM7 | NM_005451 | 0.00654348 | −2.18595 |
| NR_002952//SNORA9//small nucleolar RNA, H/ACA box 9//7p13//677798////AK | SNORA9 | NR_002952 | 0.0244704 | −2.19918 |
| NM_003069//SMARCA1//SWI/SNF related, matrix associated, actin dependent regu | SMARCA1 | NM_003069 | 0.00571381 | −2.2109 |
| NR_003330//SNORD116-15//small nucleolar RNA, C/D box 116-15//15q11.2//10 | SNORD116-15 | NR_003330 | 6.72E−05 | −2.21218 |
| NM_002398//MEIS1//Meis homeobox 1// 2p14//4211///ENST00000272369//MEI | MEIS1 | NM_002398 | 0.0208728 | −2.21341 |
| ENST00000436525//C15orf51//dynamin 1 pseudogene//15q26.3//196968 | C15orf51 | ENST00000436525 | 0.0297132 | −2.22015 |
| ENST00000436525//C15orf51//dynamin 1 pseudogene//15q26.3//196968 | C15orf51 | ENST00000436525 | 0.0297132 | −2.22015 |
| NM_003734//AOC3//amine oxidase, copper containing 3 (vascular adhesion prote | AOC3 | NM_003734 | 0.0151647 | −2.22019 |
| AF391113//C21orf70//chromosome 21 open reading frame 70//21q22.3//85395 | C21orf70 | AF391113 | 0.00109586 | −2.22308 |
| NM_001937//DPT//dermatopontin//1q12-q23//1805///ENST00000367817//DPT | DPT | NM_001937 | 0.0379186 | −2.22359 |
| NM_012232//PTRF//polymerase I and transcript release factor//17q21.2//28 | PTRF | NM_012232 | 0.0194925 | −2.23107 |
| NM_024605//ARHGAP10//Rho GTPase activating protein 10//4q31.23//79658// | ARHGAP10 | NM_024605 | 0.00832518 | −2.23204 |
| NM_022117//TSPYL2//TSPY-like 2// Xp11.2//64061///ENST00000375442//TSP | TSPYL2 | NM_022117 | 0.0134024 | −2.23502 |
| NM_005100//AKAP12//A kinase (PRKA) anchor protein 12//6q24-q25//9590// | AKAP12 | NM_005100 | 0.0357306 | −2.24089 |
| AY423733//DDR2//discoidin domain receptor tyrosine kinase 2//1q23.3//492 | DDR2 | AY423733 | 0.0358613 | −2.2447 |
| NM_153703//PODN//podocan//1p32.3// 127435///ENST00000312553//PODN// | PODN | NM_153703 | 0.0277365 | −2.26923 |
| NM_004370//COL12A1//collagen, type X//, alpha 1//6q12-q13//1303//NM_0 | COL12A1 | NM_004370 | 0.0499701 | −2.27002 |
| NM_004137//KCNMB1//potassium large conductance calcium-activated channel, su | KCNMB1 | NM_004137 | 0.0277682 | −2.27584 |
| NM_014575//SCHIP1//schwannomin interacting protein 1//3q25.32-q25.33//29 | SCHIP1 | NM_014575 | 0.00470657 | −2.28272 |

TABLE 1-continued

| Gene Information | Gene Symbol | RefSeq | p-value (CC vs UC) | Fold Increase |
|---|---|---|---|---|
| NM_001753//CAV1//caveolin 1, caveolae protein, 22 kDa//7q31.1//857///NM | CAV1 | NM_001753 | 0.0368534 | −2.29054 |
| NM_002338//LSAMP//limbic system-associated membrane protein//3q13.2-q21// | LSAMP | NM_002338 | 0.0456749 | −2.30408 |
| NM_058229//FBXO32//F-box protein 32// 8q24.13//114907///NM_148177//FB | FBXO32 | NM_058229 | 0.0422526 | −2.30763 |
| NM_006765//TUSC3//tumor suppressor candidate 3//8p22//7991//NM_178234 | TUSC3 | NM_006765 | 0.00173576 | −2.32217 |
| NM_015687//FILIP1//filamin A interacting protein 1//6q14.1//27145///EN | FILIP1 | NM_015687 | 0.0158717 | −2.32321 |
| NM_006080//SEMA3A//sema domain, immunoglobulin domain (Ig), short basic doma | SEMA3A | NM_006080 | 0.0142131 | −2.32699 |
| NM_000922//PDE3B//phosphodiesterase 3B, cGMP-inhibited//11p15.1//5140// | PDE3B | NM_000922 | 0.00420057 | −2.33135 |
| NM_000722//CACNA2D1//calcium channel, voltage-dependent, alpha 2/delta subun | CACNA2D1 | NM_000722 | 0.0107345 | −2.33411 |
| NM_001197294//DPYSL3// dihydropyrimidinase-like 3//5q32//1809/// NM_0013 | DPYSL3 | NM_001197294 | 0.0231385 | −2.33517 |
| NM_172311//STON1-GTF2A1L//STON1-GTF2A1L readthrough//2p16.3//286749/// | TON1-GTF2A1 | NM_172311 | 0.0264382 | −2.33729 |
| NM_000857//GUCY1B3//guanylate cyclase 1, soluble, beta 3//4q31.3-q33//29 | GUCY1B3 | NM_000857 | 0.0141507 | −2.34285 |
| NR_033662//CSF3//colony stimulating factor 3 (granulocyte)//17q11.2-q12// | CSF3 | NR_033662 | 0.036854 | −2.35397 |
| NM_001706//BCL6//B-cell CLL/lymphoma 6//3q27//604///NM_001130845//BC | BCL6 | NM_001706 | 0.0395014 | −2.37213 |
| NM_014112//TRPS1//trichorhinophalangeal syndrome ///8q24.12//7227//EN | TRPS1 | NM_014112 | 0.021813 | −2.37338 |
| NM_003275//TMOD1//tropomodulin 1// 9q22.3//7111///NM_001166116//TMOD1 | TMOD1 | NM_003275 | 0.00926909 | −2.39163 |
| NM_004040//RHOB//ras homolog gene family, member B//2p24//388///ENST00 | RHOB | NM_004040 | 0.00209611 | −2.39166 |
| NM_007281//SCRG1//stimulator of chondrogenesis 1//4q34.1//11341///ENST | SCRG1 | NM_007281 | 0.0449505 | −2.42771 |
| NM_053025//MYLK//myosin light chain kinase//3q21//4638 ///NM_053026// | MYLK | NM_053025 | 0.0334323 | −2.44896 |
| NM_133646//ZAK//sterile alpha motif and leucine zipper containing kinase AZK | ZAK | NM_133646 | 0.0101002 | −2.45225 |
| NM_001123364//C6orf186//chromosome 6 open reading frame 186//6q21//72846 | C6orf186 | NM_001123364 | 0.0338175 | −2.45305 |
| NM_005909//MAP1B//microtubule-associated protein 1B//5q13//4131/// ENST | MAP1B | NM_005909 | 0.00199713 | −2.45363 |
| NM_001136191//KANK2//KN motif and ankyrin repeat domains 2//19p13.2//259 | KANK2 | NM_001136191 | 0.00418 | −2.45823 |
| NR_002836//PGM5P2//phosphoglucomutase 5 pseudogene 2//9q12//595135///N | PGM5P2 | NR_002836 | 0.0106051 | −2.46207 |
| NM_006988//ADAMTS1//ADAM metallopeptidase with thrombospondin type 1 motif, | ADAMTS1 | NM_006988 | 0.0212926 | −2.47602 |
| NM_001897//CSPG4//chondroitin sulfate proteoglycan 4//15q24.2//1464/// | CSPG4 | NM_001897 | 0.000233664 | −2.47738 |
| NM_012134//LMOD1//leiomodin 1 (smooth muscle)//1q32//25802///ENST00000 | LMOD1 | NM_012134 | 0.0254164 | −2.48821 |
| NM_000856//GUCY1A3//guanylate cyclase 1, soluble, alpha 3//4q31.3-q33|4q31 | GUCY1A3 | NM_000856 | 0.0154068 | −2.49669 |
| NR_002196//H19//H19, imprinted maternally expressed transcript (non-protein | H19 | NR_002196 | 0.0422207 | −2.49895 |
| NM_002667//PLN//phospholamban// 6q22.1//5350///ENST00000357525//PLN/ | PLN | NM_002667 | 0.0458219 | −2.50528 |
| NM_004078//CSRP1//cysteine and glycine-rich protein 1//1q32//1465///NM | CSRP1 | NM_004078 | 0.0389579 | −2.51599 |
| NM_001141945//ACTA2//actin, alpha 2, smooth muscle, aorta//10q23.3//59/ | ACTA2 | NM_001141945 | 0.00367966 | −2.51621 |
| NM_002986//CCL11//chemokine (C—C motif) ligand 11//17q21.1-q21.2//6356/ | CCL11 | NM_002986 | 0.0132628 | −2.5178 |
| NM_033138//CALD1//caldesmon 1// 7q33//800//NM_033157//CALD1//calde | CALD1 | NM_033138 | 0.0229067 | −2.51869 |
| NM_001164836//FXYD6//FXYD domain containing ion transport regulator 6//11q | FXYD6 | NM_001164836 | 0.0202065 | −2.53004 |
| NM_003725//HSD17B6//hydroxysteroid (17-beta) dehydrogenase 6 homolog (mouse) | HSD17B6 | NM_003725 | 0.0196889 | −2.54527 |
| NM_001146312//MYOCD//myocardin// 17p11.2//93649///NM_153604//MYOCD// | MYOCD | NM_001146312 | 0.0298805 | −2.59465 |
| NM_015225//PRUNE2//prune homolog 2 (Drosophila)//9q21.2//158471///AB53 | PRUNE2 | NM_015225 | 0.0217217 | −2.59492 |

TABLE 1-continued

| Gene Information | Gene Symbol | RefSeq | p-value (CC vs UC) | Fold Increase |
|---|---|---|---|---|
| NM_001168278//INVVTR1//WW domain containing transcription regulator 1//3q23- | INVVTR1 | NM_001168278 | 0.014475 | −2.60243 |
| NM_001008711//RBPMS//RNA binding protein with multiple splicing//8p12//1 | RBPMS | NM_001008711 | 0.00600769 | −2.60406 |
| NM_001014796//DDR2//discoidin domain receptor tyrosine kinase 2//1q23.3// | DDR2 | NM_001014796 | 0.00523497 | −2.61121 |
| NM_018640//LMO3//LIM domain only 3 (rhombotin-like 2)//12p12.3//55885// | LMO3 | NM_018640 | 0.042971 | −2.63105 |
| NR_002836//PGM5P2// phosphoglucomutase 5 pseudogene 2// 9q12//595135///N | PGM5P2 | NR_002836 | 0.00678244 | −2.64929 |
| NM_021914//CFL2//cofilin 2 (muscle)// 14q12//1073//NM_138638//CFL2/ | CFL2 | NM_021914 | 0.0261349 | −2.65343 |
| NM_016277//RAB23//RAB23, member RAS oncogene family//6p11//51715//NM_ | RAB23 | NM_016277 | 0.035448 | −2.66122 |
| NM_145234//CHRDL1//chordin-like 1// Xq23//91851///NM_001143981//CHRDL | CHRDL1 | NM_145234 | 0.00265317 | −2.67563 |
| NM_001134439//PHLDB2//pleckstrin homology-like domain, family B, member 2// | PHLDB2 | NM_001134439 | 0.0258326 | −2.67775 |
| NM_006832//FERMT2//fermitin family member 2//14q22.1//10979//NM_00113 | FERMT2 | NM_006832 | 0.0205617 | −2.7145 |
| NM_001128205//SULF1//sulfatase 1// 8q13.1//23213//NM_015170//SULF1/ | SULF1 | NM_001128205 | 0.0335496 | −2.73234 |
| NM_194272//RBPMS2//RNA binding protein with multiple splicing 2//15q22.31 | RBPMS2 | NM_194272 | 0.012053 | −2.74286 |
| NM_014476//PDLIM3//PDZ and LIM domain 3//4q35//27295//NM_001114107// | PDLIM3 | NM_014476 | 0.0110612 | −2.7574 |
| NM_015886//PI15//peptidase inhibitor 15// 8q21.11//51050//ENST00000260 | PI15 | NM_015886 | 0.0312943 | −2.78937 |
| NM_003289//TPM2//tropomyosin 2 (beta)// 9p13//7169//NM_213674//TPM2 | TPM2 | NM_003289 | 0.0272347 | −2.80338 |
| NM_001458//FLNC//filamin C, gamma// 7q32-q35//2318//NM_001127487//FL | FLNC | NM_001458 | 0.0113027 | −2.80588 |
| NM_006097//MYL9//myosin, light chain 9, regulatory//20q11.23//10398/// | MYL9 | NM_006097 | 0.0412118 | −2.81849 |
| NM_199460//CACNA1C//calcium channel, voltage-dependent, L type, alpha 1C sub | CACNA1C | NM_199460 | 0.00694625 | −2.83404 |
| NM_001232//CASQ2//calsequestrin 2 (cardiac muscle)//1p13.3-p11//845/// | CASQ2 | NM_001232 | 0.0349505 | −2.84886 |
| NM_001193460//MSRB3//methionine sulfoxide reductase B3//12q14.3//253827 | MSRB3 | NM_001193460 | 0.0108076 | −2.84899 |
| NM_001456//FLNA//filamin A, alpha// Xq28//2316//NM_001110556//FLNA/ | FLNA | NM_001456 | 0.0164878 | −2.86026 |
| NM_006366//CAP2//CAP, adenylate cyclase-associated protein, 2 (yeast)//6p2 | CAP2 | NM_006366 | 0.00596997 | −2.89059 |
| NM_001031701//NT5DC3//5′-nucleotidase domain containing 3//12q22-q23.1// | NT5DC3 | NM_001031701 | 0.0464686 | −2.90347 |
| NM_003999//OSMR//oncostatin M receptor//5p13.1//9180///NM_001168355// | OSMR | NM_003999 | 0.0324297 | −2.92605 |
| NM_001885//CRYAB//crystallin, alpha B// 11q22.3-q23.1//1410///ENST00000 | CRYAB | NM_001885 | 0.0163674 | −2.96044 |
| NM_000517//HBA2//hemoglobin, alpha 2// 16p13.3//3040//BC101846//HBA1 | HBA2 | NM_000517 | 0.0195505 | −3.10109 |
| NM_000558//HBA1//hemoglobin, alpha 1// 16p13.3//3039//BC101846//HBA1 | HBA1 | NM_000558 | 0.0195505 | −3.10109 |
| NM_004282//BAG2//BCL2-associated athanogene 2//6p12.1-p11.2//9532//EN | BAG2 | NM_004282 | 0.0108668 | −3.11097 |
| NM_022135//POPDC2//popeye domain containing 2//3q13.33//64091///ENST00 | POPDC2 | NM_022135 | 0.0219995 | −3.1427 |
| NM_001001522//TAGLN//transgelin// 11q23.2//6876//NM_003186//TAGLN// | TAGLN | NM_001001522 | 0.0148609 | −3.35842 |
| NM_212482//FN1//fibronectin 1//2q34// 233//NM_002026//FN1//fibron | FN1 | NM_212482 | 0.00987492 | −3.43741 |
| NM_133477//SYNPO2//synaptopodin 2// 4q26//171024//NM_001128933//SYNP | SYNPO2 | NM_133477 | 0.0241716 | −3.56252 |
| NM_000450//SELE//selectin E//1q22-q25//6401//ENST00000333360//SELE | SELE | NM_000450 | 0.0460446 | −3.56423 |
| NR_029686//MIR145//microRNA 145// 5q32//406937//NR_027180//LOC728264 | MIR145 | NR_029686 | 0.0119026 | −3.58867 |
| NM_022648//TNS1//tensin 1//2q35-q36// 7145//ENST00000171887//TNS1// | TNS1 | NM_022648 | 0.00555851 | −3.61273 |
| NM_001615//ACTG2//actin, gamma 2, smooth muscle, enteric//2p13.1//72/// | ACTG2 | NM_001615 | 0.0379131 | −3.62826 |
| NM_022844//MYH11//myosin, heavy chain 11, smooth muscle//16p13.11//4629 | MYH11 | NM_022844 | 0.0240032 | −3.66415 |

TABLE 1-continued

| Gene Information | Gene Symbol | RefSeq | p-value (CC vs UC) | Fold Increase |
|---|---|---|---|---|
| NM_002205//ITGA5//integrin, alpha 5 (fibronectin receptor, alpha polypeptide | ITGA5 | NM_002205 | 0.0207749 | −3.82521 |
| NM_001299//CNN1//calponin 1, basic, smooth muscle//19p13.2-p13.1//1264/ | CNN1 | NM_001299 | 0.0413103 | −3.84711 |
| NM_001034954//SORBS1//sorbin and SH3 domain containing 1//10q23.33//1058 | SORBS1 | NM_001034954 | 0.00399907 | −3.89048 |
| NM_001927//DES//desmin//2q35//1674/// ENST00000373960//DES//desmin | DES | NM_001927 | 0.0268126 | −3.90558 |
| NM_144617//HSPB6//heat shock protein, alpha-crystallin-related, B6//19q13. | HSPB6 | NM_144617 | 0.0145209 | −3.90993 |
| NM_015424//CHRDL2//chordin-like 2// 11q14//25884///ENST00000263671//C | CHRDL2 | NM_015424 | 0.0247555 | −4.23746 |
| NM_000518//HBB//hemoglobin, beta// 11p15.5//3043//ENST00000335295//H | HBB | NM_000518 | 0.0255665 | −4.3277 |
| NM_002160//TNC//tenascin C//9q33// 3371////ENST00000350763//TNC//ten | TNC | NM_002160 | 0.0126641 | −4.4403 |
| NM_006198//PCP4//Purkinje cell protein 4//21q22.2//5121///ENST00000328 | PCP4 | NM_006198 | 0.0340302 | −4.51736 |

What is claimed is:

1. A method of diagnosing and treating at least one of moderate ulcerative colitis, severe ulcerative colitis, or Crohn's disease in a patient suffering from or at risk of inflammatory bowel disease, said method comprising:
    obtaining a sample from inflamed tissue of the patient;
    measuring at least one of an expression of HD5 or a concentration of HD5 in the sample;
    comparing the expression of HD5 or the concentration of HD5 in the sample to a benchmark value that is typical of a subject not suffering from Crohn's disease; and either
        diagnosing moderate ulcerative colitis or severe ulcerative colitis if the expression of HD5 or the concentration of HD5 in the sample does not significantly exceed the benchmark value and performing a surgical intervention on the patient to treat the moderate ulcerative colitis or the severe ulcerative colitis; or
        diagnosing Crohn's disease if the expression of HD5 or the concentration of HD5 in the sample significantly exceeds the benchmark value and performing a non-surgical intervention on the patient to treat Crohn's disease, wherein the non-surgical intervention includes at least one of administration of a drug for treating Crohn's disease to the patient or placement of the patient on a low fat diet.

2. The method of claim 1, wherein the expression of HD5 is measured in the sample is no more than about 1/31 of expression of HD5 measured in a control sample from a subject not suffering from Crohn's disease.

3. The method of claim 1, wherein the expression of HD5 is measured to be less than $10^6$ HD5 mRNA transcripts per 10 ng RNA.

4. The method of claim 1, wherein the sample is intestinal tissue, and wherein the method further comprises measuring the concentration of HD5 by:

immunostaining the sample with an anti-HD5 immunostaining agent; and measuring the percentage of cells in the sample that stain positive, wherein the percentage of cells in the sample that stain positive is less than 10%.

5. The method of claim 1, wherein the surgical intervention is not effective to treat Crohn's disease.

6. The method of claim 1, wherein the surgical intervention is selected from the group consisting of: a proctocolectomy and an ileal pouch anal anastomosis.

7. The method of claim 1, wherein the measured expression of HD5 is no more than about 1/118 of expression of HD5 measured in a control sample from a subject not suffering from Crohn's disease.

8. The method of claim 1, wherein the expression of HD5 is measured to be at least about 31 times greater in the sample than in a control sample from a subject not suffering from Crohn's disease.

9. The method of claim 1, wherein the expression of HD5 is measured to be at least about 118 times greater in the sample than in a control sample from a subject not suffering from Crohn's disease.

10. The method of claim 1, wherein the expression of HD5 is measured to be greater than about $10^6$ HD5 mRNA transcripts per 10 ng RNA.

11. The method of claim 1, wherein the sample is intestinal tissue, and wherein the method further comprises measuring the concentration of HD5 by:

immunostaining the sample with an anti-HD5 immunostaining agent; and measuring the percentage of cells in the sample that stain positive, wherein the percentage of cells in the sample that stain positive is at least 20%.

12. The method of claim 1, wherein the non-surgical intervention is not effective to treat ulcerative colitis.

13. The method of claim 1, wherein after diagnosing the patient with Crohn's disease, the patient is administered a drug for treating Crohn's disease and placed on a low fat.

14. The method of claim 1, wherein the drug is selected from the group consisting of: a vitamin supplement, an anti-inflammatory, a corticosteroid, a 5-aminosalicylate, an immunosuppressant, azathioprine, mercaptopurine, an anti-TNF-alpha antibody, infliximab, adalimumab, certolizumab pegol, methotrexate, an anti-α4-integrin antibody, natalizumab, vedolizumab, an anti-interleukin antibody, ustekinumab, an antibacterial antibiotic, ciprofloxacin, and metronidazole.

15. The method of claim 1, wherein the drug is selected from the group consisting of: vitamin B12, vitamin D, calcium, certolizumab pegol, methotrexate, and natalizumab.

16. The method of claim 1, wherein the patient displays one or more of severe diarrhea, abdominal pain, fatigue, or weight loss.

17. The method of claim 1, wherein the at least one of an expression of HD5 or a concentration of HD5 in the sample is measured by cation-ion exchange, NMR analysis, genome-wide transcriptome analysis, or mass spectrometry.

* * * * *

SEQUENCE LISTING

<160> NUMBER OF SEQ ID NOS: 4

<210> SEQ ID NO 1
<211> LENGTH: 94
<212> TYPE: PRT
<213> ORGANISM: Homo sapiens

<400> SEQUENCE: 1

Met Arg Thr Ile Ala Ile Leu Ala Ala Ile Leu Leu Val Ala Leu Gln
1               5                   10                  15

Ala Gln Ala Glu Ser Leu Gln Glu Arg Ala Asp Glu Ala Thr Thr Gln
            20                  25                  30

Lys Gln Ser Gly Glu Asp Asn Gln Asp Leu Ala Ile Ser Phe Ala Gly
        35                  40                  45

Asn Gly Leu Ser Ala Leu Arg Thr Ser Gly Ser Gln Ala Arg Ala Thr
    50                  55                  60

Cys Tyr Cys Arg Thr Gly Arg Cys Ala Thr Arg Glu Ser Leu Ser Gly
65                  70                  75                  80

Val Cys Glu Ile Ser Gly Arg Leu Tyr Arg Leu Cys Cys Arg
                85                  90

<210> SEQ ID NO 2
<211> LENGTH: 94
<212> TYPE: PRT
<213> ORGANISM: Homo sapiens

<400> SEQUENCE: 2

Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Val Ser Leu Ala
        35                  40                  45

Trp Asp Glu Ser Leu Ala Pro Lys His Pro Gly Ser Arg Lys Asn Met
    50                  55                  60

Asp Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys

```
                        85                     90

<210> SEQ ID NO 3
<211> LENGTH: 94
<212> TYPE: PRT
<213> ORGANISM: Homo sapiens

<400> SEQUENCE: 3

Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Val Ser Leu Ala
        35                  40                  45

Trp Asp Glu Ser Leu Ala Pro Lys His Pro Gly Ser Arg Lys Asn Met
    50                  55                  60

Ala Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90

<210> SEQ ID NO 4
<211> LENGTH: 99
<212> TYPE: PRT
<213> ORGANISM: Homo sapiens

<400> SEQUENCE: 4

Met Arg Thr Leu Thr Ile Leu Thr Ala Val Leu Leu Val Ala Leu Gln
1               5                   10                  15

Ala Lys Ala Glu Pro Leu Gln Ala Glu Asp Asp Pro Leu Gln Ala Lys
            20                  25                  30

Ala Tyr Glu Ala Asp Ala Gln Glu Gln Arg Gly Ala Asn Asp Gln Asp
        35                  40                  45

Phe Ala Val Ser Phe Ala Glu Asp Ala Ser Ser Ser Leu Arg Ala Leu
    50                  55                  60

Gly Ser Thr Arg Ala Phe Thr Cys His Cys Arg Arg Ser Cys Tyr Ser
65                  70                  75                  80

Thr Glu Tyr Ser Tyr Gly Thr Cys Thr Val Met Gly Ile Asn His Arg
                85                  90                  95

Phe Cys Cys
```